(12) United States Patent
Toner et al.

(10) Patent No.: US 8,394,398 B2
(45) Date of Patent: *Mar. 12, 2013

(54) METHODS OF ADMINISTERING RAPAMYCIN ANALOGS WITH ANTI-INFLAMMATORIES USING MEDICAL DEVICES

(75) Inventors: John L. Toner, Libertyville, IL (US);
Sandra E. Burke, Libertyville, IL (US);
Keith R. Cromack, Gurnee, IL (US);
Matthew Mack, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 803 days.

This patent is subject to a terminal disclaimer.

(21) Appl. No.: 11/548,827

(22) Filed: Oct. 12, 2006

(65) Prior Publication Data

US 2007/0224240 A1 Sep. 27, 2007

Related U.S. Application Data

(60) Continuation-in-part of application No. 10/796,243, filed on Mar. 9, 2004, now Pat. No. 7,445,792, and a continuation-in-part of application No. 10/977,288, filed on Oct. 29, 2004, now Pat. No. 7,399,480, which is a continuation-in-part of application No.

(Continued)

(51) Int. Cl.
| | |
|---|---|
| A01N 43/42 | (2006.01) |
| A61F 2/06 | (2006.01) |
| A61F 13/00 | (2006.01) |
| A61K 31/44 | (2006.01) |

(52) U.S. Cl. ....... 424/422; 514/291; 623/1.15; 623/1.42

(58) Field of Classification Search .................. None
See application file for complete search history.

(56) References Cited

U.S. PATENT DOCUMENTS

| | | | |
|---|---|---|---|
| 3,929,992 | A | 12/1975 | Sehgal |
| 3,993,749 | A | 11/1976 | Sehgal |

(Continued)

FOREIGN PATENT DOCUMENTS

| | | |
|---|---|---|
| EP | 0184162 A2 | 6/1986 |
| EP | 0467606 A1 | 1/1992 |

(Continued)

OTHER PUBLICATIONS

Boland et al. International Journal of Cardiovascular Interventions 2000 3:215-225.*

(Continued)

*Primary Examiner* — Robert A Wax
*Assistant Examiner* — Caralynne Helm
(74) *Attorney, Agent, or Firm* — Squire Sanders (US) LLP

(57) ABSTRACT

A medical device comprising a supporting structure capable of including or supporting a pharmaceutically acceptable carrier or excipient, which carrier or excipient may include one or more therapeutic agents or substances, with the carrier including a coating on the surface thereof, and the coating including the therapeutic substances, such as, for example, drugs. Supporting structures for the medical devices that are suitable for use in this invention include, but are not limited to, coronary stents, peripheral stents, catheters, arteriovenous grafts, by-pass grafts, and drug delivery balloons used in the vasculature. Drugs that are suitable for use in this invention include, but are notlimited to,

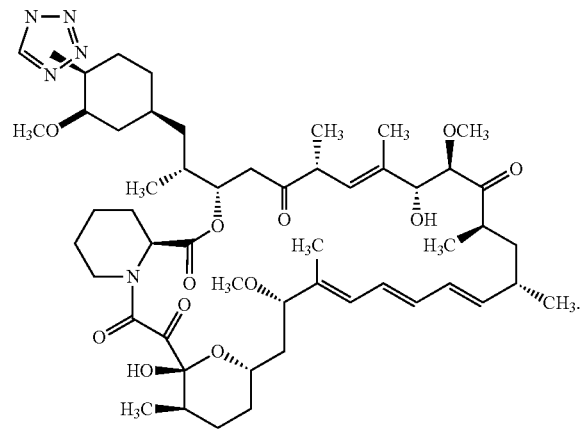

This drug can be used in combination with another drug including those selected from anti-proliferative agents, anti-platelet agents, anti-inflammatory agents, anti-thrombotic agents, cytotoxic drugs, agents that inhibit cytokine or chemokine binding, cell de-differentiation inhibitors, anti-lipaedemic agents, matrix metalloproteinase inhibitors, cytostatic drugs, or combinations of these drugs.

23 Claims, 15 Drawing Sheets

Related U.S. Application Data

10/235,572, filed on Sep. 6, 2002, now abandoned, which is a continuation-in-part of application No. 09/950,307, filed on Sep. 10, 2001, now Pat. No. 6,890,546, which is a continuation-in-part of application No. 09/433,001, filed on Nov. 2, 1999, now Pat. No. 6,329,386, which is a division of application No. 09/159,945, filed on Sep. 24, 1998, now Pat. No. 6,015,815, application No. 11/548,827, which is a continuation-in-part of application No. 11/084,172, filed on Mar. 18, 2005.

(60) Provisional application No. 60/453,555, filed on Mar. 10, 2003, provisional application No. 60/060,105, filed on Sep. 26, 1997, provisional application No. 60/554,730, filed on Mar. 19, 2004, provisional application No. 60/727,080, filed on Oct. 14, 2005, provisional application No. 60/726,878, filed on Oct. 14, 2005, provisional application No. 60/732,577, filed on Oct. 17, 2005, provisional application No. 60/727,196, filed on Oct. 14, 2005.

(56) References Cited

U.S. PATENT DOCUMENTS

| | | | |
|---|---|---|---|
| 4,316,885 A | 2/1982 | Rakhit | |
| 4,401,653 A | 8/1983 | Eng | |
| 4,650,803 A | 3/1987 | Stella | |
| 4,885,171 A | 12/1989 | Surendra | |
| 4,916,193 A | 4/1990 | Tang | |
| 4,994,071 A | 2/1991 | MacGregor | |
| 5,023,262 A | 6/1991 | Caufield | |
| 5,092,877 A | 3/1992 | Pinchuk | |
| 5,120,725 A | 6/1992 | Kao | |
| 5,120,727 A | 6/1992 | Kao | |
| 5,120,842 A | 6/1992 | Failli | |
| 5,163,952 A | 11/1992 | Froix | |
| 5,177,203 A | 1/1993 | Failli | |
| 5,304,121 A | 4/1994 | Sahatjian | |
| 5,447,724 A | 9/1995 | Helmus | |
| 5,457,111 A | 10/1995 | Luly | |
| 5,464,650 A | 11/1995 | Berg | |
| 5,516,781 A | 5/1996 | Morris | |
| 5,527,337 A | 6/1996 | Stack | |
| 5,563,146 A | 10/1996 | Morris | |
| 5,605,696 A | 2/1997 | Eury | |
| 5,624,411 A | 4/1997 | Tuch | |
| 5,646,160 A | 7/1997 | Morris | |
| 5,665,728 A | 9/1997 | Morris | |
| 5,705,583 A | 1/1998 | Bowers | |
| 5,843,172 A * | 12/1998 | Yan | 623/1.42 |
| 6,015,815 A * | 1/2000 | Mollison | 514/291 |
| 6,090,901 A | 7/2000 | Bowers | |
| 6,273,913 B1 | 8/2001 | Wright | |
| 6,284,305 B1 | 9/2001 | Ding | |
| 6,299,604 B1 * | 10/2001 | Ragheb et al. | 604/265 |
| 6,358,556 B1 | 3/2002 | Ding | |
| 6,413,272 B1 | 7/2002 | Igaki | |
| 6,419,692 B1 | 7/2002 | Yang | |
| 6,585,764 B2 | 7/2003 | Wright | |
| 2003/0129215 A1 | 7/2003 | Mollison | |
| 2003/0216699 A1 | 11/2003 | Falotico | |
| 2005/0004661 A1 | 1/2005 | Lewis | |
| 2006/0198867 A1 | 9/2006 | Toner et al. | |

FOREIGN PATENT DOCUMENTS

| | | |
|---|---|---|
| WO | 92/05179 | 4/1992 |
| WO | 01/87372 A1 | 11/2001 |
| WO | WO 01/87372 * | 11/2001 |
| WO | 02/055122 A1 | 7/2002 |
| WO | WO 2007/032777 | 3/2007 |
| WO | WO 2008/021124 | 2/2008 |

OTHER PUBLICATIONS

Wei et al. Journal of Cardiothoracic and Vascular Anesthesia 2001 4:455-459.*

Salem et al. International Archives of Allergy and Immunology 2000 121:235-245.*

Stella A Case for Prodrugs in Prodrugs: Challenges and Rewards Part I Eds. Stella et al. New York: Springer, 2007. 1-33.*

Reil et al. Journal of Surgical Research 1999 85:109-114.*

Roberge et al. Ocular Immunology and Inflammation1995 3:195-202.*

International Search Report for PCT/US2007/021846, mailed Mar. 9, 2009, 13 pgs.

Aggarwal, A., D.J. Schneider, B.E. Sobel, and H.L. Dauerman. 2003. Comparison of inflammatory markers in patients with diabetes mellitus versus those without before and after coronary arterial stenting. Am J Cardiol. 92:924-9.

Baker, H., A. Sidorowicz, S.N. Sehgal, and C. Vezina. 1978. Rapamycin (AY-22,989), a new antifungal antibiotic. III. In vitro and in vivo evaluation. J Antibiot (Tokyo). 31:539-45.

Bierer, B.E., S.L. Schreiber, and S.J. Burakoff. 1991. The effect of the immunosuppressant FK-506 on alternate pathways of T cell activation. Eur J Immunol. 21:439-45.

Biondi-Zoccai, G.G., A. Abbate, G. Liuzzo, and L.M. Biasucci. 2003. Atherothrombosis, inflammation, and diabetes. J Am Coll Cardiol. 41:1071-7.

Brown, E.J., M.W. Albers, T.B. Shin, K. Ichikawa, C.T. Keith, W.S. Lane, and S.L. Schreiber. 1994. A mammalian protein targeted by G1-arresting rapamycin-receptor complex. Nature. 369:756-8.

Bunchman, T.E., and C.A. Brookshire. 1991. Smooth muscle cell proliferation by conditioned media from cyclosporine-treated endothelial cells: a role of endothelin. Transplant Proc. 23:967-8.

Carter, A.J., M. Aggarwal, G.A. Kopia, F. Tio, P.S. Tsao, R. Kolata, A.C. Yeung, G. Llanos, J. Dooley, and R. Falotico. 2004. Long-term effects of polymer-based, slow-release, sirolimus-eluting stents in a porcine coronary model. Cardiovasc Res. 63:617-24.

Dandona, P., A. and A. Aljada. 2002. A rational approach to pathogenesis and treatment of type 2 diabetes mellitus, insulin resistance, inflammation, and atherosclerosis. Am J Cardiol. 90:27G-33G.

Dumont, F.J., M.R. Melino, M.J. Staruch, S.L. Koprak, P.A. Fischer, and N.H. Sigal. 1990. The immunosuppressive macrolides FK-506 and rapamycin act as reciprocal antagonists in murine T cells. J Immunol. 144:1418-24.

Fretz, H., M. Albers, A. Gala, R. Standaert, W. Lane, S. Burakoff, B. Bierer, and S. Schreiber. 1991. Rapamycin and FK506 binding proteins (immunophilins). J. Am. Chem. Soc. 113:1409-1411.

Grech, E.D., and D.R. Ramsdale. 2003. Acute coronary syndrome: unstable angina and non-ST segment elevation myocardial infarction. British Med. J. 326:1259-61.

Harding, M.W., A. Galat, D.E. Uehling, and S.L. Schreiber. 1989. A receptor for the immunosuppressant FK506 is a cis-trans peptidyl-prolyl isomerase. Nature. 341:758-60.

Hayward, C., D.Yohannes, and S. Danishefsky. 1993. Total synthesis of rapamycin via a novel titanium-mediated aldol macrocyclization reaction. J. Am. Chem. Soc. 115:9345-9346.

Helmus, M. 1990. Medical Device Design—A Systems Approach: Central Venous Catheters. In 22nd International Society for the Advancement of Material and Process Engineering Technical Conference.

Ji, Q., M. Reimer, and T. El-Shourbagy. 2004. 96-well liquid—liquid extraction liquid chromatography-tandem mass spectrometry method for the quantitative determination of ABT-578 in human blood samples. Journal of Chromatography B. 805:67-75.

Kino, T., N. Inamura, F. Sakai, K. Nakahara, T. Goto, M. Okuhara, M. Kohsaka, H. Aoki, and T. Ochiai. 1987. Effect of FK-506 on human mixed lymphocyte reaction in vitro. Transplant Proc. 19:36-9.

Kornowski, R., M.K. Hong, F.O. Tio, O. Bramwell, H. Wu, and M.B. Leon. 1998. In-stent restenosis: contributions of inflammatory responses and arterial injury to neointimal hyperplasia. J Am Coll Cardiol. 31:224-30.

Martel, R.R., J. Klicius, and S. Galet. 1977. Inhibition of the immune response by rapamycin, a new antifungal antibiotic. Can J Physiol Pharmacol. 55:48-51.

Morris, R. 1992. Rapamycins: antifungal, antitumor, antiproliferative, and immunosuppressive macrolides. Transplant. Rev. 6:39-87.

Morris, R., and B. Meiser. 1989. Identification of a new pharmacologic action for an old compound. Med. Sci. Res. 17:609.

Nicolaou, K., T. Chakraborty, A. Piscopio, N. Minowa, and P. Bertinato. 1993. Total synthesis of rapamycin. J. Am. Chem. Soc. 115:4419-4420.

Paiva, N.L., A.L. Demain, and M.F. Roberts. 1991. Incorporation of acetate, propionate, and methionine into rapamycin by Streptomyces hygroscopicus. J Nat Prod. 54:167-77.

Roffi, M., and E.J. Topol. 2004. Percutaneous coronary intervention in diabetic patients with non-ST-segment elevation acute coronary syndromes. Eur Heart J. 25:190-8.

Romo, D., S. Meyer, D. Johsnon, and S. Schrieber. 1993. Total synthesis of (-)-rapamycin using an Evans-Tishchenko fragment coupling. J. Am. Chem. Soc. 115:7906-7907.

Sabatini, D.M., H. Erdjument-Bromage, M. Lui, P. Tempst, and S.H. Snyder. 1994. RAFT1: a mammalian protein that binds to FKBP12 in a rapamycin-dependent fashion and is homologous to yeast TORs. Cell. 78:35-43.

Schwartz, R. 1992. Restenosis and the proportional neointimal response to coronary artery injury: results in a porcine model. J Am Coll Cardiol. 19:267-274.

Sehgal, S.N., H. Baker, C.P. Eng, K. Singh, and C. Vezina. 1983. Demethoxyrapamycin (AY-24,668), a new antifungal antibiotic. J Antibiot (Tokyo). 36:351-4.

Sehgal, S.N., H. Baker, and C. Vezina. 1975. Rapamycin (AY-22,989), a new antifungal antibiotic. II. Fermentation, isolation and characterization. J Antibiot (Tokyo). 28:727-32.

Shichiri, M., Y. Hirata, T. Nakajima, K. Ando, T. Imai, M. Yanagisawa, T. Masaki, and F. Marumo. 1991. Endothelin-1 is an autocrine/paracrine growth factor for human cancer cell lines. J Clin Invest. 87:1867-71.

Siekierka, J.J., S.H. Hung, M. Poe, C.S. Lin, and N.H. Sigal. 1989. A cytosolic binding protein for the immunosuppressant FK506 has peptidyl-prolyl isomerase activity but is distinct from cyclophilin. Nature. 341:755-7.

Suzuki, T., G. Kopia, S. Hayashi, L.R. Bailey, G. Llanos, R. Wilensky, B.D. Klugherz, G. Papandreou, P. Narayan, M.B. Leon, A.C. Yeung, F. Tio, P.S. Tsao, R. Falotico, and A.J. Carter. 2001. Stent-based delivery of sirolimus reduces neointimal formation in a porcine coronary model. Circulation. 104:1188-93.

Vezina, C., A. Kudelski, and S.N. Sehgal. 1975. Rapamycin (AY-22,989), a new antifungal antibiotic. I. Taxonomy of the producing streptomycete and isolation of the active principle. J Antibiot (Tokyo). 28:721-6.

Yamagishi, S., C.C. Hsu, K. Kobayashi, and H. Yamamoto. 1993. Endothelin 1 mediates endothelial cell-dependent proliferation of vascular pericytes. Biochem Biophys Res Commun. 191:840-6.

Yudkin, J.S., M. Kumari, S.E. Humphries, and V. Mohamed-Ali. 2000. Inflammation, obesity, stress and coronary heart disease: is interleukin-6 the link? Atherosclerosis. 148:209-14.

\* cited by examiner

Mean ATB-578 Blood Concentration - Time Profiles, Log-Linear Scale

Mean ± SD $C_{max}$ and $AUC_{0-24}$ on Day 14 versus Dose

Mean ABT-578 Blood Concentration - Time Profiles for the 200, 400, and 800 μg OD Dose Groups on Day 1, Day 14 and Days 1 through 14

Zotarolimus Release from Stents Loaded with Either Zotarolimus (10 μg/mm) Alone or Zotarolimus (10 μg/mm) and Dexamethasone (10 μg/mm)

Neointimal areas for combination stents vs. single drug-eluting stents and control – 28-day swine study Neointimal thicknesses for combination stents vs. single drug-eluting stents and contol – 28-day swine study % area stenoses for combination stents vs. single drug-eluting stents and control – 28-day swine study Comparison of neointimal area measurements for combination stents Representative Vessel Segments

*Micrographs represent average neointimal areas for each group

METHODS OF ADMINISTERING RAPAMYCIN ANALOGS WITH ANTI-INFLAMMATORIES USING MEDICAL DEVICES

CROSS-REFERENCE TO RELATED APPLICATIONS

This application is a continuation-in-part of U.S. patent application Ser. No. 10/796,243 filed Mar. 9, 2004 now U.S. Pat. No. 7,445,792, which claims the benefit of U.S. Prov. Pat. App. Ser. No. 60/453,555 filed Mar. 10, 2003. This application is also a continuation-in-part of U.S. patent application Ser. No. 10/977,288 filed Oct. 29, 2004 now U.S. Pat. No. 7,399,480, which is a continuation-in-part of U.S. patent application Ser. No. 10/235,572, filed Sep. 6, 2002 now abandoned, which is a continuation-in-part of U.S. patent application Ser. No. 09/950,307, filed Sep. 10, 2001, now U.S. Pat. No. 6,890,546, which is a continuation-in-part of U.S. patent application Ser. No. 09/433,001, filed Nov. 2, 1999, now U.S. Pat. No. 6,329,386, which is a divisional of U.S. patent application Ser. No. 09/159,945, filed Sep. 24, 1998, now U.S. Pat. No. 6,015,815, which patent claims the benefit of U.S. Prov. Pat. App. Ser. No. 60/060,105, filed Sep. 26, 1997. This application is also a continuation-in-part of U.S. patent application Ser. No. 11/084,172, filed Mar. 18, 2005, which claims the benefit of U.S. Prov. Pat. App. Ser. No. 60/554,730 filed Mar. 19, 2004. This application also claims the benefit of U.S. Prov. Pat. Apps. Ser. Nos. 60/727,080 filed Oct. 14, 2005, 60/726,878 filed Oct. 14, 2005, 60/732,577 filed Oct. 17, 2005 and 60/727,196 filed Oct. 14, 2005. The entirety of all the above is incorporated by reference as if fully set forth herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable.

TECHNICAL FIELD

The invention relates to novel chemical compounds having immunomodulatory activity and/or anti-restenotic activity and synthetic intermediates useful for the preparation of the novel compounds, and in particular to macrolide immunomodulators. More particularly, the invention relates to semi-synthetic analogs of rapamycin, means for their preparation, pharmaceutical compositions containing such compounds, and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Recently, several classes of macrocyclic compounds having potent immunomodulatory activity have been discovered. Okuhara et al., in European Patent Application No. 184,162, published Jun. 11, 1986, disclose a number of macrocyclic compounds isolated from the genus Streptomcyes, including the immunosuppressant FK-506, a 23-membered macrocyclic lactone, which was isolated from a strain of S. tsukbaensis.

Other related natural products, such as FR-900520 and FR-900523, which differ from FK-506 in their alkyl substituent at C-21, have been isolated from S. bygroscopicus yakushimnaensis. Another analog, FR-900525, produced by S. tsukbaensis, differs from FK-506 in the replacement of a pipecolic acid moiety with a proline group. Unsatisfactory side-effects associated with cyclosporine and FK-506 such as nephrotoxicity, have led to a continued search for immunosuppressant compounds having improved efficacy and safety, including an immunosuppressive agent which is effective topically, but ineffective systemically (U.S. Pat. No. 5,457,111).

Rapamycin is a macrocyclic triene antibiotic produced by Streptomcyes hygroscopicus, which was found to have antifungal activity, particularly against Candida albicans, both in vitro and in vivo (C. Vezina et al., J. Antibiot. 1975, 28, 721; S, N. Sehgal et al., J. Antibiot 1975, 28, 727; H. A. Baker et al., J. Antibiot. 1978, 31, 539; U.S. Pat. No. 3,929,992; and U.S. Pat. No. 3,993,749).

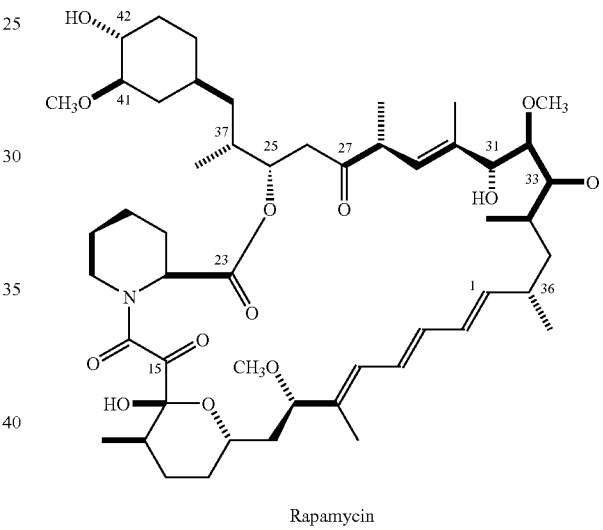

Rapamycin

Rapamycin alone U.S. Pat. No. 4,885,171) or in combination with picibanil (U.S. Pat. No. 4,401,653) has been shown to have antitumor activity. In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies (R. Martel et al., Can. J. Physiol. Pharmacol., 1977, 55, 48).

The immunosuppressive effects of rapamycin have also been disclosed in FASEB, 1989, 3, 3411 as has its ability to prolong survival time of organ grafts in histoincompatible rodents (R. Morris, Med. Sci. Res., 1989, 17, 609). The ability of rapamycin to inhibit T-cell activation was disclosed by M. Strauch (FASEB, 1989, 3, 3411). These and other biological effects of rapamycin have been previously reviewed in Transplantation Reviews, 1992, 6, 39-87.

Rapamycin has been shown to reduce neointimal proliferation in animal models, and to reduce the rate of restenosis in humans. Evidence has been published showing that rapamycin also exhibits an anti-inflammatory effect, a characteristic which supported its selection as an agent for the treatment of rheumatoid arthritis. Because both cell proliferation and inflammation are thought to be causative factors in the formation of restenotic lesions after balloon angioplasty and stent placement, rapamycin and analogs thereof have been proposed for the prevention of restenosis.

Mono-ester and di-ester derivatives of rapamycin (esterification at positions 31 and 42) have been shown to be useful as antifungal agents (U.S. Pat. No. 4,316,885) and as water soluble prodrugs of rapamycin (U.S. Pat. No. 4,650,803).

Fermentation and purification of rapamycin and 30-demethoxy rapamycin have been described in the literature (C. Vezina et al. *J. Antibiot.* (Tokyo), 1975, 28 (10), 721; S. N. Sehgal et al., *J. Antibiot.* (Tokyo), 1975, 28(10), 727; 1983, 36(4), 351; N. L. Paiva et al., *J. Natural Products*, 1991, 54(1), 167-177).

Numerous chemical modifications of rapamycin have been attempted. These include the preparation of mono- and di-ester derivatives of rapamycin (WO 92/05179), 27-oximes of rapamycin EP0 467606); 42-oxo analog of rapamycin (U.S. Pat. No. 5,023,262); bicyclic rapamycins (U.S. Pat. No. 5,120,725); rapamycin dimers U.S. Pat. No. 5,120,727); silyl ethers of rapamycin (U.S. Pat. No. 5,120,842); and arylsulfonates and sulfamates U.S. Pat. No. 5,177,203). Rapamycin was recently synthesized in its naturally occurring enantiomeric form (K. C. Nicolaou et al., *J. Am. Chem. Soc.,* 1993, 115, 4419-4420; D. Romo et al., *J. Am. Chem. Soc.,* 1993, 115, 7906-7907; C. Hayward, *J. Am. Chem. Soc.,* 1993, 115, 9345-9346.

It has been known that rapamycin, like FK-506, binds to FKBP-12 (Siekierka, J. J.; Hung, S. H. Y.; Poe, M.; Lin, C. S.; Sigal, N. H. *Nature,* 1989, 341, 755-757; Harding, M. W.; Galat, A.; Uehling, D. E.; Schreiber, S. L. *Nature* 1989, 341, 758-760; Dumont, F. J.; Melino, M. R.; Staruch, M. J.; Koprak, S. L.; Fischer, P. A.; Sigal, N. H. *J. Immunol.* 1990, 144, 1418-1424; Bierer, B. E.; Schreiber, S. L.; Burakoff, S. J. *Eur. J. Immunol.* 1991, 21, 439-445; Fretz, H.; Albers, M. W.; Galat, A.; Standaert, R. F.; Lane, W. S.; Burakoff, S. J.; Bierer, B. E.; Schreiber, S. L. *J. Am. Chem. Soc.* 1991, 113, 1409-1411). It has also been shown that the rapamycin/FKBP-12 complex binds to yet another protein, m-TOR, which is distinct from calcineurin, the protein that the FK-506/FKBP-12 complex inhibits Brown, E. J.; Albers, M. W.; Shin, T. B.; Ichikawa, K.; Keith, C. T.; Lane, W. S.; Schreiber, S. L. *Nature* 1994, 369, 756-758; Sabatini, D. M.; Erdjument-Bromage, H.; Lui, M.; Tempest, P.; Snyder, S. H. *Cell,* 1994, 78, 35-43).

Other drugs have been used to counter unwanted cell proliferation. Exemplary of these is paclitaxel. A complex alkaloid extracted from the Pacific Yew, *Taxus brevifolia,* paclitaxel stabilizes components of the cell skeleton (tubulin, the building blocks of microtubules) that are critical in cell division, thus preventing cell proliferation filler and Ojima, 2001).

Percutaneous transluminal coronary angioplasty PTCA) was developed by Andreas Gruntzig in the 1970's. The first canine coronary dilation was performed on Sep. 24, 1975; studies showing the use of PTCA were presented at the annual meetings of the American Heart Association the following year. Shortly thereafter, the first human patient was studied in Zurich, Switzerland, followed by the first American human patients in San Francisco and New York. While this procedure changed the practice of interventional cardiology with respect to treatment of patients with obstructive coronary artery disease, the procedure did not provide long-term solutions. Patients received only temporary abatement of the chest pain associated with vascular occlusion; repeat procedures were often necessary. It was determined that the existence of restenotic lesions severely limited the usefulness of the new procedure. In the late 1980's, stents were introduced to maintain vessel patency after angioplasty. Stenting is involved in 90% of the angioplasties performed today. Before the introduction of stents, the rate of restenosis ranged from 30-50% of the patients who were treated with balloon angioplasty. Introduction of stenting resulted in further improvements in outcomes, with restenosis rates of 1530%. Following stenting, the restenosis lesion is caused primarily by neointimal hyperplasia, which is distinctly different from atherosclerotic disease both in time-course and in histopathologic appearance. Restenosis is a healing process of damaged coronary arterial walls, with neointimal tissue impinging significantly on the vessel lumen. Vascular brachytherapy appears to be efficacious against in-stent restenosis lesions. Radiation, however, has limitations of practicality and expense, and lingering questions about safety and durability.

The major effort undertaken by the interventional device community to fabricate and evaluate drug eluting stents has met the original goal by reducing restenosis by at least 50%. However there still remains a need for improved local drug delivery devices, e.g., a drug-impregnated polymer-coated stent, that provide safe and efficacious tools for preventing and treating restenosis. For example, the two commercially available single-drug eluting stents reduce restenosis and improve patient outcomes, but do not eliminate restenosis or are free of adverse safety issues. Patients, and especially at-risk patients, including diabetics, those with small vessels and those with acute coronary syndromes, could benefit from local drug delivery devices, including stents with improved capabilities.

Drug delivery devices including combinations of drugs are known. However, the art does not appear to teach particularly effective drug combinations administered locally, e.g., eluted from a stent. For example, and as discussed more below, Falotico teaches an EVA-PBMA polymer-coated stent including a rapamycin/dexamethasone combination was "far less effective" in reducing neointimal area, percent-area stenosis, and inflammation scores than stents delivering either rapamycin alone or dexamethasone alone.

BRIEF DESCRIPTION OF THE DRAWINGS

FIGS. 24a-e show micrographs of cross-sections of representative blood vessels from a swine study, representing average neointimal areas for each group. FIG. 24a, TriMaxx™, stent; 24b, ZoMaxx™, stent; 24c, Cypher® stent; 24d, Taxus® stent; 24e, zotarolimus:paclitaxel, 10 μg/mm:1 μg/mm stent.

SUMMARY OF THE INVENTION

Figure 1:
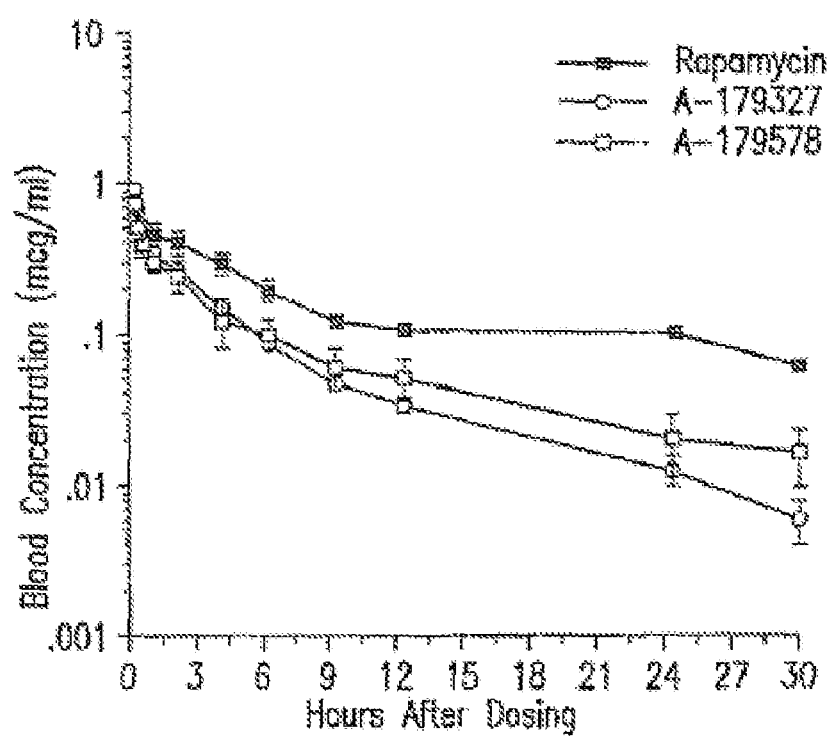
FIG. 1 shows blood concentrations±SEM (n=3) of tetrazole-containing rapamycin analogs dosed in monkey.

In one aspect of the embodiments of the invention are disclosed compounds represented by the structural formula:

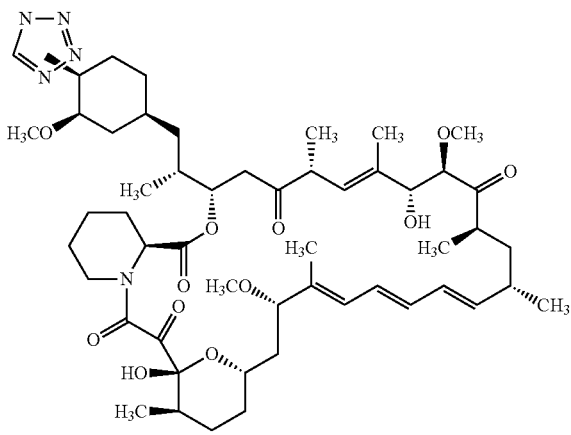

or a pharmaceutically acceptable salt or prodrug thereof.

In another aspect of the invention, the invention relates to a system for providing controlled release delivery of drugs for treatment or inhibition of neointimal hyperplasia in a blood vessel lumen, including a composition having a therapeutic amount of a first drug and a therapeutic amount of a second drug, wherein the first drug includes at least one olimus drug and their its salts, esters, prodrugs and derivatives thereof; and wherein the first drug is therapeutically effective and, in the presence of the therapeutic amount of the second drug, complements activity of the second drug and wherein the second drug is therapeutically effective and, in the presence of the therapeutic amount of the first drug, complements activity of the first drug.

Yet in another aspect, the invention relates to a pharmaceutical composition for reducing neointimal hyperplasia administered locally, including at least one olimus drug and at least one glucocorticosteriod, wherein the olimus drug(s) and the glucocorticosteriod(s) are in a ratio of between about 10:1 to about 1:10.

In an aspect, embodiments of the invention are directed to a drug delivery system that has a supporting structure including at least one pharmaceutically acceptable carrier or excipient, and a therapeutic composition having zotarolimus and dexamethasone or derivatives, prodrugs, or salts thereof, wherein the formation of neointimal hyperplasia is reduced when the system is implanted in a lumen of a blood vessel of a subject when compared to a control system. The drug delivery system can include a stent, and can include a third—or more—drugs or other therapeutic substances, including biologicals. Other therapeutic substances include, but not limited to, anti-proliferative agents, anti-platelet agents, steroidal and non-steroidal anti-inflammatory agents, anti-thrombotic agents, and thrombolytic agents. The subject can be mammalians including, but not limited to, humans and swine.

Another object of embodiments of the invention is to provide synthetic processes for the preparation of such compounds from starting materials obtained by fermentation, as well as chemical intermediates useful in such synthetic processes.

A further object of embodiments of the invention is to provide pharmaceutical compositions containing, as an active ingredient, at least one of the above compounds.

Yet another object of embodiments of the invention is to provide a method of treating a variety of disease states, including restenosis, post-transplant tissue rejection, immune and autoimmune dysfunction, fungal growth, and cancer.

In another aspect of embodiments of the invention provides a medical device comprising a supporting structure having a coating on at least one portion of the surface thereof, the coating including a therapeutic substance, such as, for example, a drug. Supporting structures for the medical devices that are suitable for use in this invention include, but are not limited to, coronary stents, peripheral stents, catheters, arterio-venous grafts, by-pass grafts, and drug delivery balloons used in the vasculature including angioplasty balloons. Drugs that are suitable for use in this invention include, but are not limited to,

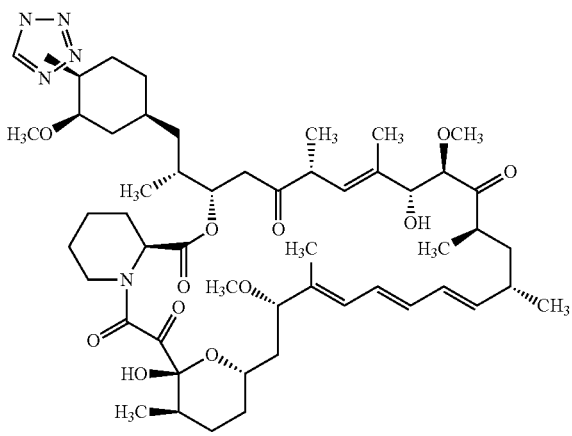

or a pharmaceutically acceptable salt or prodrug thereof, which includes

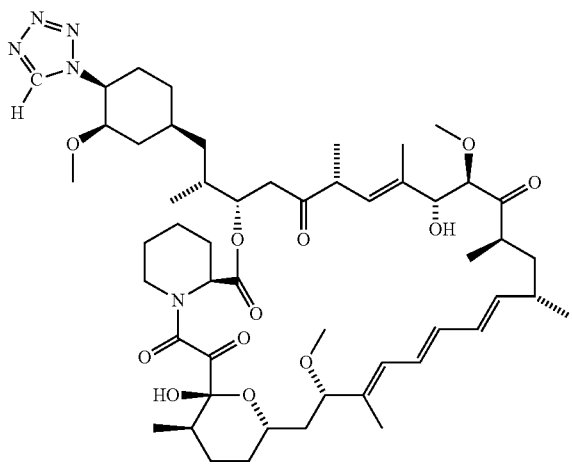 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@H](n3cnnn3)[C@H](OC)C2)CC(=O)[C@H](C)/C=C(\C)[C@@H](O)[C@@H](OC)C(=O)[C@H](C)C[C@H](C)/C=C/C=C/C=C/1C]

or a pharmaceutically acceptable salt or prodrug thereof, (hereinafter alternatively referred to as zotarolimus, as well as A-179578), and

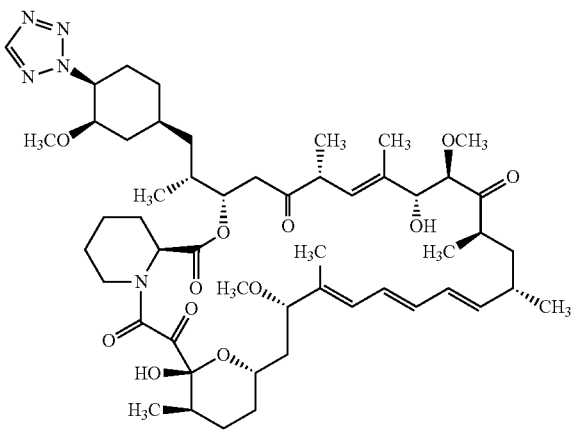 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@H](n3ncnn3)[C@H](OC)C2)CC(=O)[C@H](C)/C=C(\C)[C@@H](O)[C@@H](OC)C(=O)[C@H](C)C[C@H](C)/C=C/C=C/C=C/1C]

or a pharmaceutically acceptable salt or prodrug thereof;

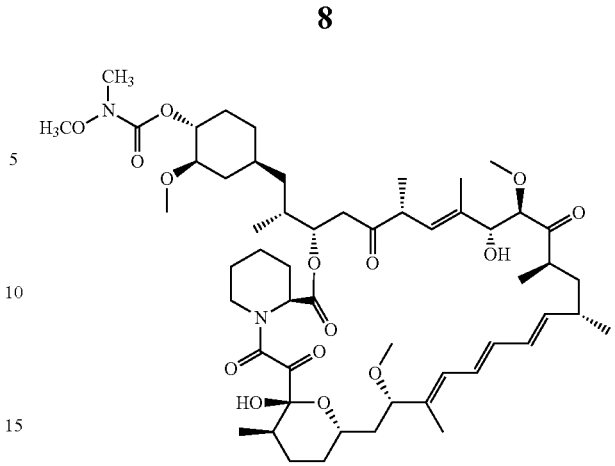

or a pharmaceutically acceptable salt or prodrug thereof, (hereinafter alternatively referred to as A-94507).

In yet another aspect, the embodiments of the invention relates to the safe and effective local delivery of drug combinations including zotarolimus and dexamethasone. The drug combinations offer improvements in safety and efficacy versus single drug eluting stents, including those found in current clinical practice (Taxus® and Cypher®).

In another aspect, the embodiments of the invention provide methods and devices to safely and effectively further reduce neointimal area, neointimal thickness and percent area stenosis associated with local delivery devices delivering drug combinations. In particular, zotarolimus/dexamethasone combinations have not been observed to adversely affect the activity of either of the drugs. Conversely, the combinations have demonstrated improvements in safety and efficacy versus single drug eluting stents, such as Taxus® and Cypher®.

Coatings that are suitable for use in embodiments of the invention include, but are not limited to, polymeric coatings that comprise any polymeric material in which the therapeutic agents may be effectively dispersed. The coating can be hydrophilic, hydrophobic, biodegradable, or nonbiodegradable. This medical device releases drugs at an appropriate rate to effectively reduce restenosis in vasculature. The direct coronary delivery of a drug including zotarolimus is expected to reduce the rate of restenosis to a level of about less than 15%.

DETAILED DESCRIPTION OF EMBODIMENTS OF THE INVENTION

Definition of Terms

The term "associated with," as used herein, refers to compounds which can be in many forms including, but not limited to, mixed, unmixed, microspheres, mixed with the coatings, mixed with the support structure. One skilled in the art would appreciated the variations of interactions between drugs, coatings/drugs, and drugs/coatings/support structures.

The term "complementary" as used herein, refers to the behavior exhibited by at least two drugs in combination where their respective pharmaceutical activities benefit from the combination by; in some instances having additive activity; in some instances having separate, but beneficial activities aiding in the overall desired pharmacological effect in mammals; and where the combination drugs do not actively reduce each other's biological activity.

The term "prodrug," as used herein, refers to compounds which are rapidly transformed in vivo to the parent compound of the above formula, for example, by hydrolysis in blood. A thorough discussion is provided by T. Higuchi and V. Stella, "Pro-drugs as Novel Delivery systems," Vol. 14 of the A. C. S. Symposium Series, and in Edward B. Roche, ed., "Bioreversible Carriers in Drug Design," American Pharmaceutical Association and Pergamon Press, 1987, both of which are incorporated herein by reference.

The term "pharmaceutically acceptable prodrugs", as used herein, refers to those prodrugs of the compounds in embodiments of the invention which are, within the scope of sound medical judgment, suitable for use in contact with the tissues of humans and lower mammals without undue toxicity, irritation, and allergic response, are commensurate with a reasonable benefit/risk ratio, and are effective for their intended use. Other embodiments include pharmaceutically acceptable prodrugs that are derivatized at the C-31 hydroxyl group.

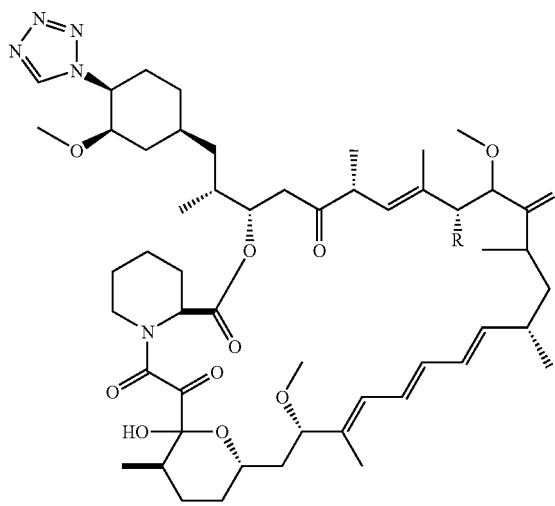

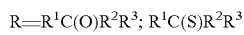

Where $R^1 = O, S$ $R^2$ = nothing, O, N, S, various alkyl, alkenyl, alkynyl, heterocycles, aryl $R^3$ = nothing, various alkyl, alkenyl, alkynyl, heterocycles, aryl Alkyl, alkenyl, alkynyl, heterocycles, aryl groups can be substituted or unsubstituted The term "prodrug esters," as used herein, refers to any of several ester-forming groups that are hydrolyzed under physiological conditions. Examples of prodrug ester groups include acetyl, proprionyl, pivaloyl, pivaloyloxymethyl, acetoxymethyl, phthalidyl, methoxymethyl, indanyl, and the like, as well as ester groups derived from the coupling of naturally or unnaturally-occurring amino acids to the C-31 hydroxyl group of compounds of embodiments of the invention.

The term "supporting structure" means a framework that is capable of including or supporting a pharmaceutically acceptable carrier or excipient, which carrier or excipient may include one or more therapeutic agents or substances, e.g., one or more drugs and/or other compounds. The supporting structure is typically formed of metal or a polymeric material. Suitable supporting structures formed of polymeric materials, including biodegradable polymers, capable of including the therapeutic agents or substances include, without limitation, those disclosed in U.S. Pat. Nos. 6,413,272 and 5,527,337, which are incorporated herein by reference.

"Subject" means a vertebrate including, but not limited to mammals, including a monkey, dog, cat, rabbit, cow, pig, goat, sheep, horse, rat, mouse, guinea pig, and human.

"Therapeutic substance" means any substance that when administered to a subject appropriately at appropriate doses, has a beneficial effect on the subject.

Embodiments

In one embodiment of the invention is a compound of formula

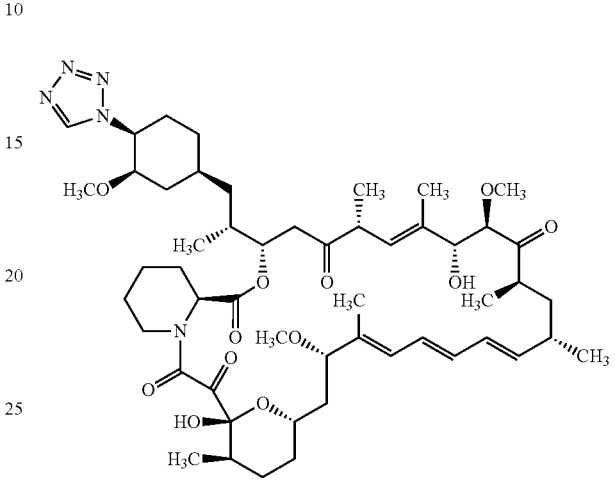

In another embodiment of the invention is a compound of formula

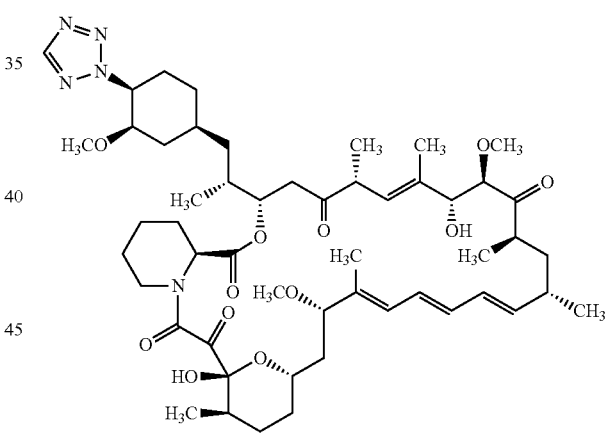

Methods of Treatment

The compounds of the invention, including but not limited to those specified in the examples, possess immunomodulatory activity in mammals (including humans). As immunosuppressants, the compounds of embodiments of the invention are useful for the treatment and prevention of immune-mediated diseases including the resistance by transplantation of organs or tissue including heart, kidney, liver, medulla ossium, skin, cornea, lung, pancreas, intestinum tenue, limb, muscle, nerves, duodenum, small-bowel, pancreatic-islet-cell, and the like; graft-versus-host diseases brought about by medulla ossium transplantation; autoimmune diseases including rheumatoid arthritis, systemic lupus erythematosus, Hashimoto's thyroiditis, multiple sclerosis, myasthenia gravis, Type I diabetes, uveitis, allergic encephalomyelitis, glomerulonephritis, and the like. Further uses include the treatment and prophylaxis of inflammatory and hyperproliferative skin diseases and cutaneous manifestations of immunologically-mediated illnesses, including psoriasis, atopic dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne and alopecia greata; various eye diseases (autoimmune and otherwise) including keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition reversible obstructive airway disease, including asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like are targeted by compounds of this invention. Inflammation of mucosa and blood vessels including gastric ulcers, vascular damage caused by ischemic diseases and thrombosis. Moreover, hyperproliferative vascular diseases including intimal smooth muscle cell hyperplasia, restenosis and vascular occlusion, particularly following biologically- or mechanically-mediated vascular injury, could be treated or prevented by the compounds of the invention.

The compounds or drugs described herein can be applied to stents that have been coated with a polymeric compound. Incorporation of the compound or drug into the polymeric coating of the stent can be carried out by dipping the polymer-coated stent into a solution including the compound or drug for a sufficient period of time (such as, for example, five minutes) and then drying the coated stent, such as, for example, by means of air drying for a sufficient period of time (such as, for example, 30 minutes). Other methods of applying therapeutic substances, including spraying, can be used. The polymer-coated stent including the compound or drug can then be delivered to the coronary vessel by deployment from a balloon catheter or via a self expanding stent. In addition to stents, other devices that can be used to introduce the drugs of this invention to the vasculature include, but are not limited to grafts, catheters, and balloons. In addition, other compounds or drugs that can be used in lieu of the drugs of this invention include, but are not limited to, A-94507 and SDZ RAD (a.k.a. Everolimus).

The compounds described herein for use in polymer-coated stents can be used in combination with other pharmacological agents. The pharmacological agents that would, in combination with the compounds of this invention, be most effective in preventing restenosis can be classified into the categories of anti-proliferative agents, anti-platelet agents, anti-inflammatory agents, anti-thrombotic agents, and thrombolytic agents. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v \beta 3$, antibodies that block binding to gpIIaIIIb or $\alpha v \beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, triamcinolone, mometasone, fluticasone, clobetasol, and non-steroidal anti-inflammatories, such as, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies. Other embodiments including the second drug being a glucocorticosteriod including methylprednisolone, prednisolone, prednisone, triamcinolone, dexamethasone, mometasone, beclomethasone, ciclesonide, bedesonide, triamcinolone, clobetasol, flunisolide, loteprednol, budesonide, fluticasone, and their its salts, esters, prodrugs, and derivatives or any combination thereof. In other embodiments, the second drug is a steroid hormone including an estradiol and salts, esters, prodrugs, and derivatives or any combination thereof.

Other agents that can be used in combination with the compounds of this invention include anti-lipaedemic agents, such as, for example, fenofibrate, atorvastatin, fluvastatin, lovastatin, mevastatin, pitavastatin, pravastatin, rosuvastatin and simvastatin. Additional agents include matrix metalloproteinase inhibitors, such as, for example, batimistat, as well as antagonists of the endothelin-A receptor, such as, for example, darusentan, and antagonists of the $\alpha v \beta 3$ integrin receptor.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparins, heparan sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of antithrombotic agents that can be delivered are factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other drugs that can be used in combination with the compounds of this invention are cytotoxic drugs, such as, for example, apoptosis inducers, such as TGF, and topoisomerase inhibitors, including 10-hydroxycamptothecin, irinotecan, and doxorubicin. Other classes of drugs that can be used in combination with the compounds of this invention are drugs that inhibit cell de-differentiation and cytostatic drugs.

Other agents that can be used in combination with the compounds of this invention include anti-lipaedemic agents, such as, for example, fenofibrate, matrix metalloproteinase inhibitors, such as, for example, batimistat, antagonists of the endothelin-A receptor, such as, for example, darusentan, and antagonists of the αvβ3 integrin receptor.

Embodiments of the invention further include a third therapeutic drug or substance. When a second drug and/or third therapeutic drug is utilized it includes, but are not limited to, anti-proliferative agents, anti-platelet agents, anti-inflammatory agents, anti-lipidemic agents, anti-thrombotic agents, thrombolytic agents, their salts, prodrugs, and derivatives or any combination thereof. When a second drug and/or third therapeutic drug is a glucocorticosteriod it includes, but is not limited to, methylprednisolone, prednisolone, prednisone, triamcinolone, dexamethasone, mometasone, beclomethasone, ciclesonide, bedesonide, triamcinolone, clobetasol, flunisolide, loteprednol, budesonide, fluticasone, their salts, prodrugs, and derivatives or any combination thereof. When a second drug and/or third therapeutic drug is a steroid hormone it includes, nut is not limited to, an estradiol and their salts, prodrugs, and derivatives or any combination thereof. In embodiments, when a second drug and/or third therapeutic drug it can be small molecules and biologics that reduce inflammatory cytokine activity. When a second drug and/or third therapeutic drug utilizes an anti-TNFα therapies it includes, but is not limited to, adalimumab, anti-MCP-1 therapies, CCR2 receptor antagonists, anti-IL-18 therapies, anti-IL-1 therapies, and their salts, prodrugs, and derivatives, or any combination thereof. When a said second drug and/or third therapeutic drug utilizes an anti-proliferative agent it includes, but is not limited to, alkylating agents including cyclophosphamide, chlorambucil, busulfan, carmustine and lomustine, anti-metabolites including methotrexate, fluorouracil, cytarabine, mercaptopurine and pentostatin, vinca alkaloids including vinblastine and vincristine, antibiotics including doxorubicin, bleomycin and mitomycin, antiproliferatives including cisplatin, procarbazine, etoposide and teniposide, their salts, prodrugs, and derivatives, or any combination thereof. When a second drug and/or third therapeutic drug utilizes an anti-platelet agent it includes, but is not limited to, glycoprotein IIB/IIIA inhibitors including abciximab, eptifibatide and tirofiban, adenosine reuptake inhibitors including dipyridamole, ADP inhibitors including clopidogrel and ticlopidine, cyclooxygenase inhibitors including acetylsalicylic acid, and phosphodiesterase inhibitors including cilostazol, their salts, prodrugs, and derivatives, or any combination thereof. When a second drug and/or third therapeutic drug utilizes an anti-inflammatory agent it includes, but is not limited to, steroids including dexamethasone, hydrocortisone, fluticasone, clobetasol, mometasone and estradiol, and non-steroidal anti-inflammatory agents including acetaminophen, ibuprofen, naproxen, sulindac, piroxicam, mefanamic acid, those that inhibit binding of cytokines or chemokines to receptors to inhibit pro-inflammatory signals, including antibodies to IL-1, IL-2, IL-8, IL-15, IL-18 and TNF, their salts, prodrugs, and derivatives, or any combination thereof. When a second drug and/or third therapeutic drug utilizes an anti-thrombotic agent it includes, but is not limited to, heparins including unfractionated heparins and low-molecular weight heparins including clivarin, dalteparin, enoxaparin, nadroparin and tinzaparin, direct thrombin inhibitors including argatroban, hirudin, hirulog, hirugen, their salts, prodrugs, and derivatives, or any combination thereof. When a second drug and/or third therapeutic drug utilizes an anti-lipidemic agent it includes, HMG CoA reductase inhibitors including mevastatin, lovastatin, simvastatin, pravastatin, fluvastatin, fibric acid derivatives including fenofibrate, clofibrate, gemfibrozil, lipid-lowering agents including nicotinic acid, probucol, their salts, prodrugs, and derivatives or any combination thereof. When a second drug and/or third therapeutic drug utilizes thrombolytic agents it includes, but is not limited to, streptokinase, urokinase, pro-urokinase, tissue plasminogen activators including alteplase, reteplase, tenectaplase, their salts, prodrugs, and derivatives, or any combination thereof.

Polymers

When used in the invention, the coating can comprise any polymeric material in which the therapeutic agents, i.e., the drugs, are substantially soluble or effectively dispersed. The purpose of the coating is to serve as a controlled release vehicle for the therapeutic agent or as a reservoir for a therapeutic agent to be delivered at the site of a lesion. The coating can be polymeric and can further be hydrophilic, hydrophobic, biodegradable, or non-biodegradable. The material for the polymeric coating can be selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. Coatings prepared from polymeric dispersions including polyurethane dispersions (BAYHYDROL, etc.) and acrylic acid latex dispersions can also be used with the therapeutic agents of the invention.

Biodegradable polymers that can be used in this invention include polymers including poly(L-lactic acid), poly(DL-lactic acid), polycaprolactone, poly hydroxy butyrate), polyglycolide, poly(diaxanone), poly hydroxy valerate), polyorthoester; copolymers including poly(lactide-co-glycolide), polyhydroxy(butyrate-co-valerate), polyglycolide-co-trimethylene carbonate; polyanhydrides; polyphosphoester; polyphosphoester-urethane; polyamino acids; polycyanoacrylates; biomolecules including fibrin, fibrinogen, cellulose, starch, collagen and hyaluronic acid; and mixtures of the foregoing. Biostable materials that are suitable for use in this invention include polymers including polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (including styrene acrylonitrile copolymers, ethylene methyl methacrylate copolymers, ethylene vinyl acetate), polyethers, rayons, cellulosics (including cellulose acetate, cellulose nitrate, cellulose propionate, etc.), parylene and derivatives thereof; and mixtures and copolymers of the foregoing.

In some embodiments, the polymers include, but are not limited to, poly(acrylates) such as poly(ethyl methacrylate), poly(n-propyl methacrylate), poly(isopropyl methacrylate), poly(isobutyl methacrylate), poly(sec-butyl methacrylate), poly(n-butyl methacrylate), poly(2-ethylhexyl methacrylate), poly(n-hexyl methacrylate), poly(cyclohexyl methacrylate), poly(n-hexyl methacrylate), poly(isobornyl methacrylate), and poly(trimethylcyclohexyl methacrylate), poly(methyl acrylate), poly(ethyl arylate), poly(n-propyl acrylate), poly(isopropyl acrylate), poly(n-butyl acrylate), poly(isobutyl acrylate), poly(sec-butyl acrylate), poly(pentyl acrylate), poly(n-hexyl acrylate), poly(cyclohexyl acrylate) and any derivatives, analogs, homologues, congeners, salts, copolymers and combinations thereof.

In some embodiments, the polymers include, but are not limited to, poly(ester urethanes), poly(ether urethanes), poly(urea urethanes), poly(urethanes); silicones; fluorosilicones, poly(esters); poly(ethylene); polypropylene); poly(olefins); copolymers of poly(isobutylene); triblock copolymers of styrene and isobutylene; triblock copolymers of styrene and ethylene/butylenes; triblock copolymers of styrene and butadiene; copolymers of ethylene-alphaolefin; vinyl halide polymers and copolymers such as poly(vinyl chloride) and poly(vinyl fluoride); poly(vinylidene halides) such as, for example, poly(vinylidene chloride) and poly(vinylidene fluoride); poly(vinylidene fluoride-co-hexafluoropropylene), poly(tetrafluoroethylene); poly(tetrafluoroethylene-co-chlorotrifluoroethylene); poly(vinyl ethers) such as, for example, poly(vinyl methyl ether); poly(acrylonitrile); poly(vinyl ketones); poly(vinyl aromatics) such as poly(styrene); poly(vinyl esters) such as poly(vinyl acetate); copolymers of vinyl monomers and olefins such as copolymers of methacrylic acid; copolymers of acrylic acid; copolymers of N-vinyl pyrrolidone; poly(vinyl alcohols); poly(ethylene-co-vinyl alcohol) (EVAL), poly(cyanoacrylates); poly(maleic anhydride) and copolymers of maleic anhydride; copolymers of acrylonitrile-styrene, ABS resins, and copolymers of ethylene-vinyl acetate; and any derivatives, analogs, homologues, congeners, salts, copolymers and combinations thereof.

In some embodiments, the polymers include, but are not limited to, poly(amides) such as Nylon 66 and poly(caprolactam); alkyd resins; poly(carbonates); poly(sulfone); poly(oxymethylenes); poly(imides); poly(ester amides); poly(ethers) including poly(alkylene glycols) such as, for example, poly(ethylene glycol) and polypropylene glycol); epoxy resins; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

Another polymer that can be used in this invention is poly $MPC_w:LAM_x:HPMA_y:TSMA_z$) where w, x, y, and z represent the molar ratios of monomers used in the feed for preparing the polymer and MPC represents the unit 2-methacryoyloxyethylphosphorylcholine, LMA represents the unit lauryl methacrylate, HPMA represents the unit 2-hydroxypropyl methacrylate, and TSMA represents the unit 3-trimethoxysilylpropyl methacrylate. The drug-impregnated stent can be used to maintain patency of a coronary artery previously occluded by thrombus and/or atherosclerotic plaque. The delivery of an anti-proliferative agent reduces the rate of in-stent restenosis. Polymers which can be used in this invention include zwitterionic polymers including phosphorylcholine units.

Other treatable conditions include but are not limited to ischemic bowel diseases, inflammatory bowel diseases, necrotizing enterocolitis, intestinal inflammations/allergies including Coeliac diseases, proctitis, eosinophilic gastroenteritis, mastocytosis, Crohn's disease and ulcerative colitis; nervous diseases including multiple myositis, Guillain-Barre syndrome, Meniere's disease, polyneuritis, multiple neuritis, mononeuritis and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis, pernicious anemia, megaloblastic anemia and aneryrthroplasia; bone diseases including osteoporosis; respiratory diseases including sarcoidosis, fibroid lung and idiopathic interstitial pneumonia; skin disease including dermatomyositis, leukoderma vulgaris, ichthyosis vulgaris, photoallergic sensitivity and cutaneous T cell lymphoma; circulatory diseases including arteriosclerosis, atherosclerosis, aortitis syndrome, polyarteritis nodosa and myocardosis; collagen diseases including scleroderma, Wegener's granuloma and Sjogren's syndrome; adiposis; eosinophilic fasciitis; periodontal disease including lesions of gingiva, periodontium, alveolar bone and substantia ossea dentis; nephrotic syndrome including glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury including ischemia-reperfusion injury of organs (including heart, liver, kidney and digestive tract) which occurs upon preservation, transplantation or ischemic disease (for example, thrombosis and cardiac infarction); intestinal diseases including endotoxin-shock, pseudomembranous colitis and colitis caused by drug or radiation; renal diseases including ischemic acute renal insufficiency and chronic renal insufficiency; pulmonary diseases including toxinosis caused by lung-oxygen or drug (for example, paracort and bleomycins), lung cancer and pulmonary emphysema; ocular diseases including cataracts, siderosis, retinitis, pigmentosa, senile macular degeneration, vitreal scarring and corneal alkali burn; dermatitis including erythema multiforme, linear IgA ballous dermatitis and cement dermatitis; and others including gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-$C_4$ release; Behcet's disease including intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease including immunogenic diseases (for example, chronic autoimmune liver diseases including autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (including alcoholic cirrhosis) and hepatic failure including fulminant hepatic failure, late-onset hepatic failure and "acute-on-chronic" liver failure (acute liver failure on chronic liver diseases), and moreover are useful for various diseases because of their potentially useful activity in augmentation of the primary chemotherapeutic, antiviral, anti-inflammatory, and cardiotonic effects of drugs the patient may already be taking.

The ability of the compounds of the invention to treat proliferative diseases can be demonstrated according to previously described methods in Bunchman E T and C A Brookshire, Transplantation Proceed. 23 967-968 (1991); Yamagishi, et al., Biochem. Biophys. Res. Comm. 191 840-846 (1993); and Shichiri, et al., J. Clin. Invest. 87 1867-1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, sclero derma, pro static hyperplasia, cardiac hyperplasia, restenosis following arterial injury or other pathologic stenosis of blood vessels. In addition, these compounds antagonize cellular responses to several growth factors, and therefore possess antiangiogenic properties, making them useful agents to control or reverse the growth of certain tumors, as well as fibrotic diseases of the lung, liver, and kidney.

Aqueous liquid compositions of embodiments of the invention are particularly useful for the treatment and prevention of various diseases of the eye including autoimmune diseases (including, for example, conical cornea, keratitis, dysophia epithelialis corneae, leukoma, Mooren's ulcer, sclevitis and Graves' opthalmopathy) and rejection of corneal transplantation.

When used in the above or other treatments, a therapeutically effective amount of one of the compounds of the embodiments of the invention may be employed in pure form or, where such forms exist, in pharmaceutically acceptable salt, ester or prodrug form. Alternatively, the compound may be administered as a pharmaceutical composition including the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the embodiments of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

For example, it is well within the skill of the art to start doses of the compound at levels lower than required to achieve the desired therapeutic effect and to gradually increase the dosage until the desired effect is achieved.

The total daily dose of the compounds in embodiments of this invention administered to a human or lower animal may range from about 0.01 to about 10 mg/kg/day. For purposes of oral administration, doses may be in the range of from about 0.001 to about 3 mg/kg/day. For the purposes of local delivery from a stent, the daily dose that a patient will receive depends on the length of the stent. For example, a 15 mm coronary stent may include a drug in an amount ranging from about 1 to about 600 micrograms and may deliver that drug over a time period ranging from several hours to several weeks. If desired, the effective daily dose may be divided into multiple doses for purposes of administration; consequently, single dose compositions may include such amounts or submultiples thereof to make up the daily dose. One skilled in the art could use the invention for topical administration and doses would depend on the site of application.

Within the scope of the invention, there is much flexibility in providing suitable drug-loaded polymer layers. For example, within therapeutic window parameters (generally levels between therapeutically effective and toxicity) associated with the drugs of interest, ratios of the drugs used in combination can be varied relative to each other. For example, an embodiment has a 90:10 total drug:polymer ratio where the ratio of drugs in the combination can be 1:1. Thus, a stent delivering a zotarolimus/dexamethasone combination according to the invention can include 10 mcg/mm zotarolimus and 10 mcg/mm dexamethasone in a PC polymer layer with a 5 mcg/mm PC topcoat. Total drug:polymer ratio can be lower, however, e.g., 40:60 or less. Upper limits on the total amount of drug will depend on several factors, including miscibility of the selected drugs in the selected polymer, the stability of the drug/polymer mixture, e.g., compatibility with sterilization, and the physical properties of the mixture, e.g., flowability/processability, elasticity, brittleness, viscosity (does not web or bridge between stent struts), coating thickness that adds substantially to the stent profile or causes delamination or cracking or is difficult to crimp. Embodiments of the invention include stent struts spaced about 60-80 microns apart, suggesting an upper limit in thickness of the drug/polymer/polymer overcoat is about 30 microns; however, any stent size, strut size and spatial spacing, and/or stent construction can be utilized for drug delivery as described therein. In embodiments, the therapeutic amount of an olimus drug includes zotarolimus or everolimus and is at least 1 µg/mm stent. In other embodiments, the second drug is a glucocorticosteriod. When the second drug is utilized in embodiments, this second drug is dexamethasone and the therapeutic amount is at least 0.5 µg/mm stentstent.

Overcoat thickness (if an overcoat is used) desirably should not unduly impede release kinetics of the drugs. The overcoat can also be loaded with one or more drugs, which can be the same or different than those in the underlying drug-loaded polymer layer.

Generally speaking, drugs useful in combinations for the invention will not adversely affect the desired activity of the other drug in the combination. The drugs proposed for use in the combination may be have complementary activities or mechanisms of action. Thus, one drug in the proposed combination should not inhibit the desired activity, e.g., antiproliferative activity, of the other drug. Nor should either drug cause or enhance the degradation of the other drug. However, a drug that might otherwise appear to be unsuitable because, for example, it degrades during sterilization, can in fact be useful because of an interaction by another drug. Thus, dexamethasone, which alone has been observed to degrade during EtO sterilization, can be used successfully in combination with zotarolimus, due to the hydrophobicity of zotarolimus. Moreover, zotarolimus has been observed to reduce the elution rate of dexamethasone, as described in Applicants' co-pending U.S. patent application Ser. No. 10/796,423.

The pharmaceutical compositions of embodiments of the invention comprise a compound and a pharmaceutically acceptable carrier or excipient, which may be administered orally, rectally, parenterally, intracisternally, intravaginally, intraperitoneally, topically (as by powders, ointments, drops or transdermal patch), bucally, as an oral or nasal spray, or locally as in a stent placed within the vasculature as in a balloon catheter, or delivery to the pericardial space or into or onto the myocardium. The phrase "pharmaceutically acceptable carrier" means a non-toxic solid, semi-solid or liquid filler, diluent, encapsulating material or formulation auxiliary of any type. The term "parenteral," as used herein, refers to all modes of administration other than oral, which include, but not limited to, intravenous, intraarterial, intramuscular, intraperitoneal, intrasternal, subcutaneous and intraarticular injection, infusion, transdermal, and placement, such as, for example, in the vasculature.

Pharmaceutical compositions of this invention for parenteral injection comprise pharmaceutically acceptable sterile aqueous or nonaqueous solutions, dispersions, suspensions, nanoparticle suspensions, or emulsions as well as sterile powders for reconstitution into sterile injectable solutions or dispersions just prior to use. Examples of suitable aqueous and nonaqueous carriers, diluents, solvents or vehicles include water, ethanol, polyols (including glycerol, propylene glycol, polyethylene glycol, and the like), carboxymethylcellulose and suitable mixtures thereof, vegetable oils (including olive oil), and injectable organic esters including ethyl oleate. Proper fluidity can be maintained, for example, by the use of coating materials including lecithin, by the maintenance of the required particle size in the case of dispersions, and by the use of surfactants.

These compositions may also include adjuvants such as, for example, preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents including sugars, sodium chloride, and the like. Prolonged absorption of the injectable pharmaceutical form may be brought about by the inclusion of agents that delay absorption including aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers including polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier including sodium citrate or dicalcium phosphate and/or a) fillers or extenders including starches, lactose, sucrose, glucose, mannitol, and silicic acid, b) binders such as, for example, carboxymethylcellulose, alginates, gelatin, polyvinylpyrrolidone, sucrose, and acacia, c) humectants including glycerol, d) disintegrating agents including agar-agar, calcium carbonate, potato or tapioca starch, alginic acid, certain silicates, and sodium carbonate, e) solution retarding agents including paraffin, f absorption accelerators including quaternary ammonium compounds, g) wetting agents such as, for example, cetyl alcohol and glycerol monostearate, h) absorbents including kaolin and bentonite clay, and i) lubricants including talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft, semi-solid and hard-filled gelatin capsules or liquid-filled capsules using such excipients as lactose or milk sugar as well as high molecular weight polyethylene glycols and the like.

The solid dosage forms for oral administration, not limited to, tablets, dragees, capsules, pills, and granules can be prepared with coatings and shells including enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Those embedding compositions including a drug can be placed on medical devices, including stents, grafts, catheters, and balloons.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may include inert diluents commonly used in the art such as, for example, water or other solvents, solubilizing agents and emulsifiers including ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants including wetting agents, emulsifying and suspending agents, sweetening, flavoring, and perfuming agents.

Suspensions, in addition to the active compounds, may include suspending agents such as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin including surfaces of the eye. Compositions for topical use on the skin also include ointments, creams, lotions, and gels. A further form of topical administration is to the eye, as for the treatment of immune-mediated conditions of the eye including autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for mucosal administration, especially those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars including lactose. Desirably, at least 95% by weight of the particles of the active ingredient have an effective particle size in the range of 0.01 to 10 micrometers. In rectal or vaginal transmucosal administration formulations include suppositories or retention enemas which can be prepared by mixing the compounds of this invention with suitable non-irritating excipients or carriers including cocoa butter, polyethylene glycol or a suppository wax which are solid at room temperature but liquid at body temperature and therefore melt in the rectum or vaginal cavity and release the active compound.

Alternatively, the composition may be pressurized and include a compressed gas, including nitrogen or a liquefied gas propellant. The liquefied propellant medium and indeed the total composition is such that the active ingredient does not dissolve therein to any substantial extent. The pressurized composition may also include a surface active agent. The surface active agent may be a liquid or solid non-ionic surface active agent or may be a solid anionic surface active agent. In other embodiments, the use of the solid anionic surface active agent is in the form of a sodium salt.

Compounds of embodiments of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. Composition embodiments in liposome form can include, in addition to a compound of the invention, stabilizers, preservatives, excipients, and the like. Lipids in embodiments are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Compounds of embodiments of the invention may also be coadministered with one or more systemic immunosuppressant agents. The immunosuppressant agents within the scope of this invention include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cyclosporin A (also marketed as different formulation of Cyclosporin A under the trademark SANDIMMUNE®), PROGRAF® tacrolimus (also known as FK-506), sirolimus and RAPAMUNE®, everolimus, leflunomide (also known as HWA-486), glucocorticoids, including prednisolone and its derivatives, antibody therapies including orthoclone (OKT3) and Zenapax®, leukemia therapies, and antithymyocyte globulins, including thymoglobulins.

Preparation of Compounds of this Invention

The compounds and processes of embodiments of the invention will be better understood in connection with the following synthetic schemes which illustrate the methods by which the compounds of the invention may be prepared.

The compounds of this invention may be prepared by a variety of synthetic routes. A representative procedure is shown in Scheme 1.

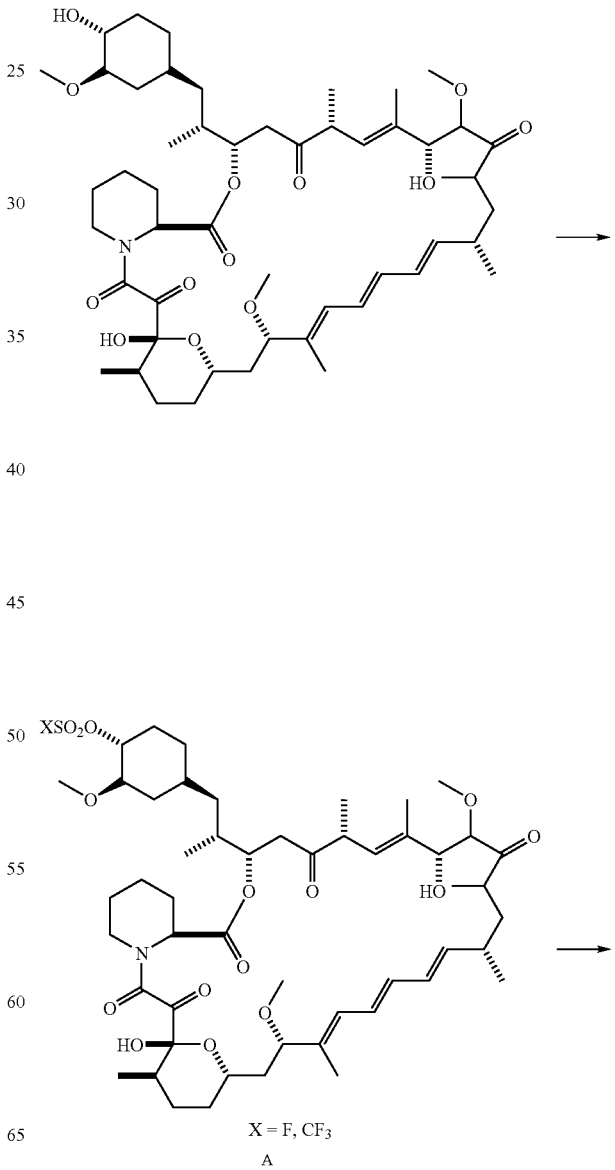

-continued

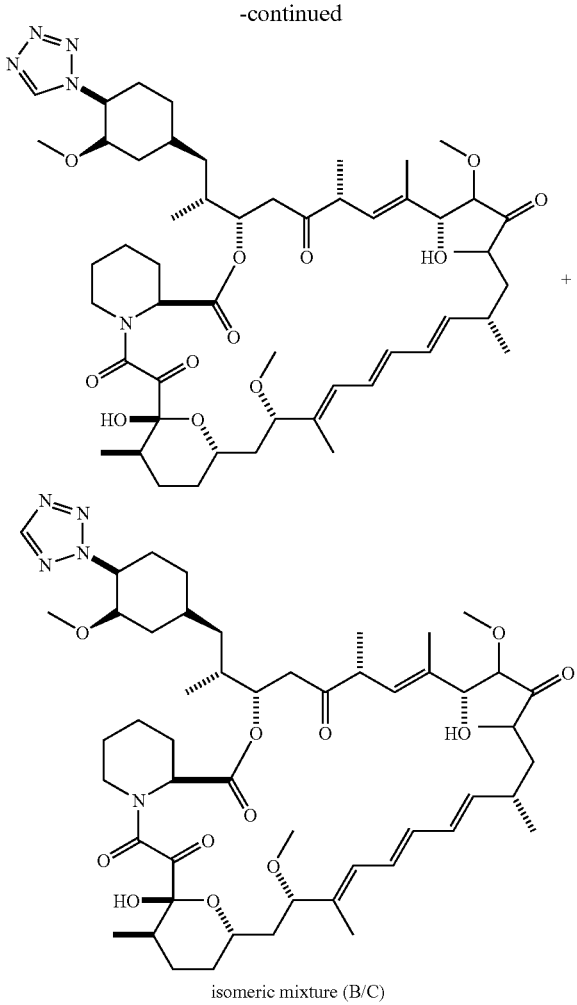

isomeric mixture (B/C)

As shown in Scheme 1, conversion of the C-42 hydroxyl of rapamycin to a trifluoromethanesulfonate or fluorosulfonate leaving group provided A. Displacement of the leaving group with tetrazole in the presence of a hindered, non-nucleophilic base, including 2,6-lutidine, diisopropylethyl amine provided isomers B and C, which were separated and purified by flash column chromatography.

Synthetic Methods

The foregoing may be better understood by reference to the following examples which illustrate the methods by which the compounds of the invention may be prepared and are not intended to limit the scope of the invention as defined in the appended claims.

Example 1

42-(2-tetrazolyl)-rapamycin (Less Polar Isomer)

Example 1A

A solution of rapamycin (100 mg, 0.11 mmol) in dichloromethane (0.6 mL) at −78° C. under a nitrogen atmosphere was treated sequentially with 2,6-lutidine (53 uL, 0.46 mmol, 4.3 eq.) and trifluoromethanesulfonic anhydride (37 uL, 0.22 mmol), and stirred thereafter for 15 minutes, warmed to room temperature and eluted through a pad of silica gel (6 mL) with diethyl ether. Fractions including the triflate were pooled and concentrated to provide the designated compound as an amber foam.

Example 1B 42-(2-tetrazolyl)-rapamycin (Less Polar Isomer)

A solution of Example 1A in isopropyl acetate (0.3 mL) was treated sequentially with diisopropylethylamine (87 mL, 0.5 mmol) and 1H-tetrazole (35 mg, 0.5 mmol), and thereafter stirred for 18 hours. This mixture was partitioned between water (10 mL) and ether (10 mL). The organics were washed with brine (10 mL) and dried $Na_2SO_4$). Concentration of the organics provided a sticky yellow solid which was purified by chromatography on silica gel (3.5 g, 70-230 mesh) eluting with hexane (10 mL), hexane:ether (4:1(10 mL), 3:1(10 mL), 2:1(10 mL), 1:4(10 mL)), ether (30 mL), hexane:acetone (1:1 (30 mL)). One of the isomers was collected in the ether fractions.

MS (ESI) m/e 966 M)⁻

Example 2

42-(1-tetrazolyl)-rapamycin (More Polar Isomer)

Collection of the slower moving band from the chromatography column using the hexane:acetone (1:1) mobile phase in Example 1B provided the designated compound.

MS (ESI) m/e 966 (M)⁻.

Pharmacoat Kinetics of Rap Analogs

The immunosuppressant activity of the compounds of embodiments of the invention were compared to rapamycin and two rapamycin analogs: 40-epi-N-[2'-pyridone]-rapamycin and 40-epi-N-[4'-pyridone]-rapamycin, both disclosed in U.S. Pat. No. 5,527,907. The activity was determined using the human mixed lymphocyte reaction (MLR) assay described by Kino, T. et al. in *Transplantation Proceedings*, XIX(5):36-39, Suppl. 6 (1987). The results of the assay demonstrate that the compounds of the invention are effective immunomodulators at nanomolar concentrations, as shown in Table 1.

TABLE 1

| Example | Human MLR $IC_{50}$ ± S.E.M.(nM) |
|---|---|
| Rapamycin | 0.91 ± 0.36 |
| 2-pyridone | 12.39 ± 5.3 |
| 4-pyridone | 0.43 ± 0.20 |
| Example 1 | 1.70 ± 0.48 |
| Example 2 | 0.66 ± 0.19 |

The pharmacokinetic behaviors of Example 1 and Example 2 were characterized following a single 2.5 mg/kg intravenous dose in cynomolgus monkey (n=3 per group). Each compound was prepared as 2.5 mg/mL solution in a 20% ethanol:30% propylene glycol:2% cremophor EL-48% dextrose 5% in water vehicle. The 1 mL/kg intravenous dose was administered as a slow bolus (~1-2 minutes) in a saphenous vein of the monkeys. Blood samples were obtained from a femoral artery or vein of each animal prior to dosing and 0.1 (IV only), 0.25, 0.5, 1, 1.5, 2, 4, 6, 9, 12, 24, and 30 hours after dosing. The EDTA preserved samples were thoroughly mixed and extracted for subsequent analysis.

An aliquot of blood (1.0 mL) was hemolyzed with 20% methanol in water (0.5 ml) including an internal standard. The hemolyzed samples were extracted with a mixture of ethyl acetate and hexane (1:1 (v/v), 6.0 mL). The organic layer was evaporated to dryness with a stream of nitrogen at room temperature. Samples were reconstituted in methanol:water (1:1, 150 µL). The title compounds (50 µL injection) were separated from contaminants using reverse phase HPLC with UV detection. Samples were kept cool (4° C.) through the run. All samples from each study were analyzed as a single batch on the HPLC.

Area under the curve (AUC) measurements of Example 1, Example 2 and the internal standard were determined using the Sciex MacQuan™ software. Calibration curves were derived from peak area ratio (parent drug/internal standard) of the spiked blood standards using least squares linear regression of the ratio versus the theoretical concentration. The methods were linear for both compounds over the range of the standard curve (correlation>0.99) with an estimated quantitation limit of 0.1 ng/mL. The maximum blood concentration ($C_{MAX}$) and the time to reach the maximum blood concentration ($T_{MAX}$) were read directly from the observed blood concentration-time data. The blood concentration data were submitted to multi-exponential curve fitting using CSTRIP to obtain estimates of pharmacokinetic parameters. The estimated parameters were further defined using NON-LIN84. The area under the blood concentration-time curve from 0 to t hours (last measurable blood concentration time point) after dosing ($AUC_{0-t}$) was calculated using the linear trapezoidal rule for the blood-time profiles. The residual area extrapolated to infinity, determined as the final measured blood concentration ($C_t$) divided by the terminal elimination rate constant ($\beta$), and added to $AUC_{0-t}$ to produce the total area under the curve ($AUC_{0-t}$).

As shown in FIG. 1 and Table 2, both Example 1 and Example 2 had a surprisingly substantially shorter terminal elimination half-life ($t_{1/2}$) when compared to rapamycin. Thus, only the compounds of the invention provide both sufficient efficacy (Table 1) and a shorter terminal half-life (Table 2).

TABLE 2

| Compound | AUC ng · hr/mL | $t_{1/2}$ (hours) |
|---|---|---|
| Rapamycin | 6.87 | 16.7 |
| 2-pyridone | 2.55 | 2.8 |
| 4-pyridone | 5.59 | 13.3 |
| Example 1 | 2.35 | 5.0 |
| Example 2 | 2.38 | 6.9 |

Example 3

The purpose of this example was to determine the effects of a rapamycin analog on neointimal formation in porcine coronary arteries including stents. This example illustrates that the rapamycin analog zotarolimus, when compounded and delivered from the Biocompatibles BiodiviYsio PC Coronary stent favorably affects neointimal hyperplasia and lumen size in porcine coronary arteries. This finding suggests that delivery of zotarolimus from a medical device may be of substantial clinical benefit if properly applied in humans by limiting neointimal hyperplasia.

The agent zotarolimus is a rapamycin analog, described and claimed in U.S. Pat. No. 6,015,815. The study set forth in this example was constructed to assess the ability of the rapamycin analog zotarolimus to reduce neointimal hyperplasia in a porcine coronary stent model. Efficacy of zotarolimus in this model would suggest its clinical potential for the limitation and treatment of coronary and vascular restenosis in stents following percutaneous revascularization. The domestic swine was used because this model appears to yield results comparable to other investigations seeking to limit neointimal hyperplasia in human subjects.

The example tested zotarolimus eluted from coronary stents placed in juvenile farm pigs, and compared these results with control stents. The control stents are polymer-coated without drugs. This is important, for the polymer itself must not stimulate neointimal hyperplasia to a substantial degree. As the eluted drug disappears, an inflammatory response to the polymer could conceivably result in a late "catch-up phenomenon" where the restenosis process is not stopped, but instead slowed. This phenomenon would result in restenosis at late dates in human subjects.

Stents were implanted in two blood vessels in each pig. Pigs used in this model were generally 2-4 months old and weighed 30-40 Kg. Two coronary stents were thus implanted in each pig by visually assessing a normal stent:artery ratio of 1.1-1.2.

Beginning on the day of the procedure, pigs were given oral aspirin (325 mg daily) and continued for the remainder of their course. General anesthesia was achieved by means of intramuscular injection followed by intravenous ketamine (30 mg/kg) and xylazine (3 mg/kg). Additional medication at the time of induction included atropine (1 mg) and flocillin (1 g) administered intramuscularly. During the stenting procedure, an intraarterial bolus of 10,000 units of heparin was administered.

Arterial access was obtained by cutdown on the right external carotid and placement of an 8F sheath. After the procedure, the animals were maintained on a normal diet without cholesterol or other special supplementation.

Figure 2:
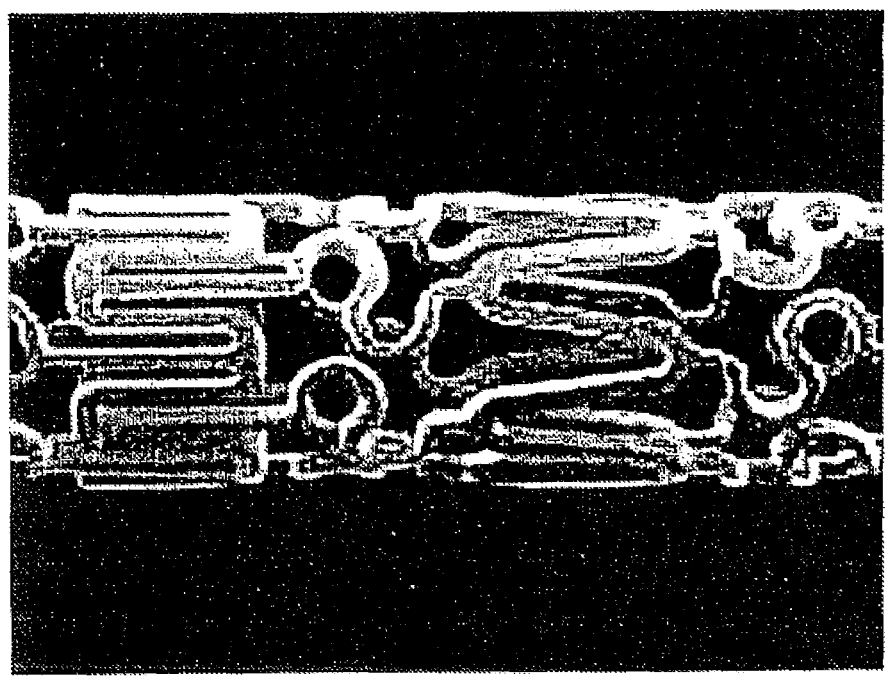
FIG. 2 is a side view in elevation showing a stent suitable for use in this invention.

The BiodivYsio stent was used with nominal vessel target size of 3.0 mm. See FIG. 2. Two coronary arteries per pig were assigned at random to deployment of the stents. The stent was either a drug eluting stent polymer plus drug stent) or a stent coated with a polymer only polymer only stent). The stents were delivered by means of standard guide catheters and wires. The stent balloons were inflated to appropriate sizes for less than 30 seconds.

Each pig had one polymer only stent and one polymer plus drug stent placed in separate coronary arteries, so that each pig would have one stent for drug and one for control.

A sample size of 20 pigs total was chosen to detect a projected difference in neointimal thickness of 0.12 mm with a standard deviation of 0.15 mm, at a power of 0.95 and beta 0.05.

Animals were euthanized at 28 days for histopathologic examination and quantification. Following removal of the heart from the perfusion pump system, the left atrial appendage was removed for access to the proximal coronary arteries. Coronary arterial segments with injuries were dissected free of the epicardium. Segments containing lesions was isolated, thereby allowing sufficient tissue to including uninvolved blood vessel at either end. The foregoing segments, each roughly 2.5 cm in length, were embedded and processed by means of standard plastic embedding techniques. The tissues were subsequently processed and stained with hematoxylin-eosin and elastic-van Gieson techniques.

Low and high power light microscopy were used to make length measurements in the plane of microscopic view by means of a calibrated reticle and a digital microscopy system connected to a computer employing calibrated analysis software.

The severity of vessel injury and the neointimal response were measured by calibrated digital microscopy. The importance of the integrity of the internal elastic lamina is well-known to those skilled in the art. A histopathologic injury score in stented blood vessels has been validated as being closely related to neointimal thickness. This score is related to depth of injury and is as follows:

| Score | Description of Injury |
|---|---|
| 0 | Internal elastic lamina intact; endothelium typically denuded, media compressed but not lacerated. |
| 1 | Internal elastic lamina lacerated; media typically compressed but not lacerated. |
| 2 | Internal elastic lacerated; media visibly lacerated; external elastic lamina intact but compressed. |
| 3 | External elastic lamina lacerated; typically large lacerations of media extending through the external elastic lamina; coil wires sometimes residing in adventitia. |

This quantitative measurement of injury was assessed for all stent struts of each stent section. The calibrated digital image was also used to measure at each stent struts site the neointimal thickness. Lumen area, area contained with the internal elastic lamina, and area within the external elastic lamina were also measured.

The mid-stent segment was used for measurement, analysis, and comparison. Data were also recorded (and included in the data section of this report) for proximal and distal segments.

Paired t-testing was performed to compare variables across the polymer only stents (control group) and polymer plus drug stents (treatment group). No animal died in this study before scheduled timepoints.

Table 3 shows the pigs and arteries used. In Table 3, LCX means the circumflex branch of the left coronary artery, LAD means the left anterior descending coronary artery, and RCA means the right coronary artery.

TABLE 3

| | Pigs and Vessels Used | |
|---|---|---|
| 1 | 2000-G-693 | RCA - Control |
| | 2000-G-693 | LCX - Test |
| 2 | 2000-G-698 | RCA - Test |
| | 2000-G-698 | LAD - Control |
| 3 | 2000-G-702 | RCA - Test |
| | 2000-G-702 | LAD - Control |
| 4 | 2000-G-709 | RCA - Control |
| | 2000-G-709 | LAD - Test |
| 5 | 2000-G-306 | RCA - Control |
| | 2000-G-306 | LAD - Test |
| | 2000-G-306 | * LCX - Test |
| 6 | 2000-G-672 | RCA - Test |
| | 2000-G-672 | LAD - Control |
| 7 | 2000-G-712 | RCA - Control |
| | 2000-G-712 | LCX - Test |
| 8 | 2000-G-735 | RCA - Control |
| | 2000-G-735 | LAD - Test |
| 9 | 2000-G-736 | RCA - Control |
| | 2000-G-736 | LCX - Test |
| 10 | 2000-G-740 | RCA - Test |
| 11 | 2000-G-742 | LAD - Test |
| | 2000-G-742 | OM (LCX) - Control |
| 12 | 2000-G-744 | RCA - Test |
| | 2000-G-744 | LAD - Control |
| 13 | 2000-G-748 | RCA - Test |
| | 2000-G-748 | LAD - Control |
| 14 | 2000-G-749 | RCA - Control |
| | 2000-G-749 | LCX - Test |

TABLE 3-continued

| | Pigs and Vessels Used | |
|---|---|---|
| 15 | 2000-G-753 | RCA - Control |
| | 2000-G-753 | LAD - Test |
| 16 | 2000-G-754 | RCA - Test |
| | 2000-G-754 | LCX - Control |
| 17 | 2000-G-755 | RCA - Control |
| | 2000-G-755 | LAD - Test |
| 18 | 2000-G-756 | RCA - Test |
| | 2000-G-756 | LAD - Control |
| 19 | 2000-G-757 | LAD - Control |
| | 2000-G-757 | LCX - Test |
| 20 | 2000-G-760 | LAD - Test |
| | 2000-G-760 | LCX - Control |

Table 4 shows the summary results for all data for mean injury and neointimal thickness for each stent, including proximal, mid, and distal segments. Table 4 also shows lumen size, percent stenosis, and artery size as measured by the internal elastic laminae (IEL) and external elastic laminae (EEL).

There was no statistically significant difference for neointimal area or thickness across proximal, mid, or distal segments within the test group polymer plus drug stents) or control groups (polymer only stents). This observation is quite consistent with prior studies, and thus allows use of only the mid segment for statistical comparison of test devices (polymer plus drug stents) vs. control devices (polymer only stents).

Table 5 shows the statistical t-test comparisons across test groups and control groups. There was a statistically significant difference in neointimal thickness, neointimal area, lumen size, and percent lumen stenosis, the drug eluting stent being clearly favored. Conversely, there were no statistically significant differences between the test group (polymer plus drug stents) and the control group (polymer only stents) for mean injury score, external elastic laminae, or internal elastic laminae areas.

Figure 3A:
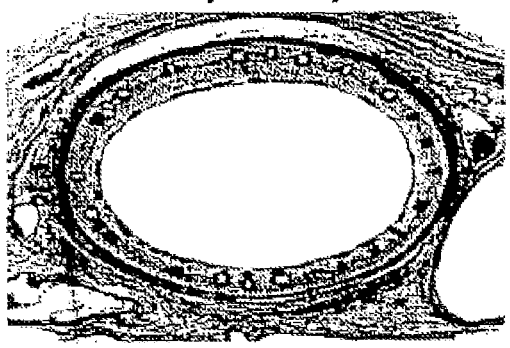
FIG. 3A is a cross-sectional view of a vessel segment in which was placed a stent coated with a polymer only.
Figure 3B:
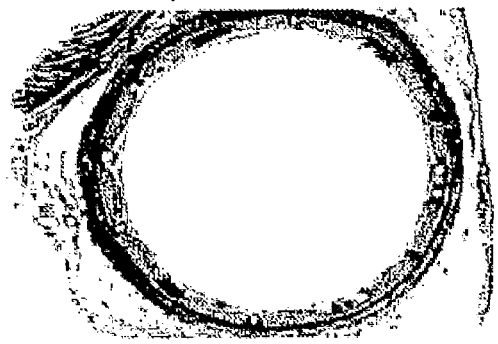
FIG. 3B is a cross-sectional view of a vessel segment in which was placed a stent coated with a polymer plus drug.

The reference arteries proximal and distal to the stented segments were observed, and quantitated. These vessels appeared normal in all cases, uninjured in both the control group (polymer only stents) and the test group polymer plus drug stents). See FIGS. 3A and 3B. The data below there were no statistically significant differences in size between the stents in the control group and the stents in the test group.

| | Proximal Reference Diameter (mm) | Distal Reference Diameter (mm) |
|---|---|---|
| Control (mean ± SD) | 4.46 ± 1.20 | 3.96 ± 1.16 |
| Test (mean ± SD) | 4.26 ± 1.26 | 3.41 ± 0.96 |

TABLE 4

Summary: All Measures (Distal, Mid, Proximal)

| ID | | prox ref | dist ref | lumen | IEL | EEL | mean injury | % stenosis | Neointimal area | NIT |
|---|---|---|---|---|---|---|---|---|---|---|
| Control | Distal | | | | | | | | | |
| Mean | | 4.46 | 3.96 | 4.88 | 7.66 | 9.00 | 0.22 | 36.10 | 2.79 | 0.41 |
| SD | | 1.20 | 1.16 | 1.30 | 1.15 | 1.10 | 0.26 | 15.41 | 1.29 | 0.17 |
| Control | Mid | | | | | | | | | |
| Mean | | 4.46 | 3.96 | 4.94 | 7.71 | 9.08 | 0.08 | 36.23 | 2.77 | 0.38 |
| SD | | 1.20 | 1.16 | 1.44 | 1.07 | 1.15 | 0.14 | 14.93 | 1.20 | 0.16 |
| Control | Proximal | | | | | | | | | |
| Mean | | 4.46 | 3.96 | 5.11 | 7.89 | 9.30 | 0.15 | 35.35 | 2.78 | 0.38 |
| SD | | 1.20 | 1.16 | 1.38 | 1.33 | 1.42 | 0.22 | 11.94 | 1.04 | 0.12 |
| Test | Distal | | | | | | | | | |
| Mean | | 4.26 | 3.41 | 6.04 | 7.70 | 9.01 | 0.26 | 22.35 | 1.66 | 0.25 |
| SD | | 1.26 | 0.96 | 1.55 | 1.49 | 1.47 | 0.43 | 8.58 | 0.58 | 0.06 |
| Test | Mid | | | | | | | | | |
| Mean | | 4.26 | 3.41 | 6.35 | 7.75 | 8.98 | 0.04 | 18.71 | 1.41 | 0.22 |
| SD | | 1.26 | 0.96 | 1.29 | 1.18 | 1.31 | 0.07 | 5.68 | 0.33 | 0.05 |
| Test | Proximal | | | | | | | | | |
| Mean | | 2.56 | 2.15 | 3.31 | 4.06 | 4.66 | 0.19 | 16.79 | 1.29 | 0.18 |
| SD | | 1.66 | 1.37 | 2.39 | 3.48 | 4.15 | 0.13 | 9.97 | 0.80 | 0.12 |

TABLE 5

Statistical Comparison of Test vs. Control Parameters: Mid-Section Data
t-test Statistics

| Parameter | Difference | t-test | DF | Std Error | Lower 95% | Upper 95% | P |
|---|---|---|---|---|---|---|---|
| Lumen | −1.17 | −2.28 | 38 | 0.52 | −2.21 | −0.13 | 0.029 |
| IEL | 0.03 | 0.088 | 38 | 0.36 | −0.71 | 0.78 | 0.93 |
| EEL | 0.2 | 0.499 | 38 | 0.39 | −0.599 | 0.99 | 0.62 |
| NI Thickness | 0.18 | 5.153 | 38 | 0.034 | 0.106 | 0.244 | <.0001 |
| NI Area | 1.21 | 3.62 | 38 | 0.33 | 0.53 | 1.88 | 0.0008 |
| Mean Injury | 0.038 | 1.137 | 38 | 0.033 | −0.02 | 0.106 | 0.26 |
| % Stenosis | 14.54 | 2.97 | 38 | 4.9 | 4.61 | 24.47 | 0.005 |

The data demonstrates that statistically significant differences exist for morphometric measures of efficacy favoring the stent that elutes zotarolimus. The stent of this invention results in lower neointimal area, lower neointimal thickness, and greater lumen area. There were no significant differences within the test group (polymer plus drug stents) and the control group (polymer only stents) for inflammation or injury parameters. There were no significant differences in artery sizes (including the stent) for the control group compared to the test group. These latter findings suggest no significant difference in the arterial remodeling characteristics of the polymeric coating including the drug.

At most, mild inflammation was found on both the polymer plus drug stent and the polymer only stent. This finding suggests that the polymer exhibits satisfactory biocompatibility, even without drug loading. Other studies show that when drug has completely gone from the polymer, the polymer itself creates enough inflammation to cause neointima. This observation may be responsible for the late catch-up phenomenon of clinical late restenosis. Because the polymer in this example did not cause inflammation in the coronary arteries, late problems related to the polymer after the drug is exhausted are unlikely.

In conclusion, a stent eluting the compound zotarolimus from a polymer showed a reduction in neointimal hyperplasia in the porcine model when placed in a coronary artery.

Example 4

The purpose of this example is to determine the rate of release of the zotarolimus drug from 316L Electropolished Stainless Steel Coupons coated with a biocompatible polymer including phosphorylcholine side groups.

Rubber septa from lids from HPLC vials were removed from the vials and placed into glass vials so that the "Teflon" side faced up. These septa served as supports for the test samples. The test samples were 316L stainless steel coupons that had been previously coated with a biocompatible polymer including phosphorylcholine side groups (PC polymer). Coronary stents are commonly made of 316L stainless steel and can be coated with the PC polymer to provide a depot site for loading drugs. The coated coupons, which serve to simulate stents, were placed onto the septa. By using a glass Hamilton Syringe, a solution of zotarolimus and ethanol (10 µl) was applied to the surface of each coupon. The solution included zotarolimus (30.6 mg) dissolved in 100% ethanol (3.0 ml). The syringe was cleaned with ethanol between each application. The cap to the glass vial was placed on the vial loosely, thereby assuring proper ventilation. The coupon was allowed to dry for a minimum of 1.5 hours. Twelve (12) coupons were loaded in this way—six being used to determine the average amount of drug loaded onto the device and six being used to measure the time needed to release the drug from the devices.

To determine the total amount of zotarolimus loaded onto a coupon, a coupon was removed from the vial and placed into 50/50 acetonitrile/0.01M phosphate buffer (pH 6.0, 5.0 ml). The coupon was placed onto a 5210 Branson sonicator for one hour. The coupon was then removed from the solution, and the solution was assayed by HPLC.

The time release studies were performed by immersing and removing the individual coupons from fresh aliquots (10.0 ml) of 0.01 M phosphate buffer at a pH of 6.0 at each of the following time intervals −5, 15, 30 and 60 minutes. For the remaining time points of 120, 180, 240, 300, 360 minutes, volumes of 5.0 ml of buffer were used. To facilitate mixing during the drug release phase, the samples were placed onto an Eberbach shaker set at low speed. All solution aliquots were assayed by HPLC after the testing of the last sample was completed.

The HPLC analysis was performed with a Hewlett Packard series 1100 instrument having the following settings:

| | |
|---|---|
| Injection Volume = | 100 µl |
| Acquisition Time = | 40 minutes |
| Flow Rate = | 1.0 ml/min |
| Column Temperature = | 40° C. |
| Wavelength = | 278 nm |
| Mobile Phase = | 65% Acetonitrile/35% $H_2O$ |
| Column = | YMC ODS-A S5 µm, 4.6 × 250 mm Part No. A12052546WT |

The results from the above experiment showed the following release data Table 6:

TABLE 6

| Time (min.) | Percent Release | Standard Deviation |
|---|---|---|
| 0.00 | 0.00 | 0.00 |
| 5.00 | 1.87 | 1.12 |
| 15.00 | 2.97 | 1.47 |
| 30.00 | 3.24 | 1.28 |
| 60.00 | 3.29 | 1.29 |
| 120.00 | 3.92 | 1.28 |
| 180.00 | 4.36 | 1.33 |
| 240.00 | 4.37 | 1.35 |
| 300.00 | 6.34 | 2.07 |
| 360.00 | 7.88 | 1.01 |

Example 5

The purpose of this example was to determine the loading and release of zotarolimus from 15 mm BiodivYsio drug delivery stents.

To load the stents with drug, a solution of zotarolimus in ethanol at a concentration of 50 mg/ml was prepared and dispensed into twelve vials. Twelve individual polymer-coated stents were placed on fixtures constructed to hold the stent in a vertical position and the stents were immersed vertically in the drug solution for five minutes. The stents and fixtures were removed from the vials and excess drug solution was blotted away by contacting the stents with an absorbent material. The stents were then allowed to dry in air for 30 minutes in an inverted vertical position.

The stents were removed from the fixtures, and each stent was placed into 50/50 acetonitrile/phosphate buffer pH 5.1, 2.0 ml) and sonicated for one hour. The stents were removed from the solution and solutions were assayed for concentration of drug, which allowed calculation of the amount of drug originally on the stents. This method was independently shown to remove at least 95% of the drug from the stent coating. On average, the stents included 120±9 micrograms of drug.

The drug-loaded stents were placed on the fixtures and placed into 0.01 M phosphate buffer (pH=6.0, 1.9 ml) in individual vials. These samples were placed onto a Eberbach shaker set at low speed to provide back-and-forth agitation. To avoid approaching drug saturation in the buffer, the stents were transferred periodically to fresh buffer vials at the following points: 15, 30, 45, 60, 120, 135, 150, 165, 180, 240, 390 minutes. The dissolution buffer vials were assayed by HPLC for the drug concentration at the end of the drug release period studied. The data, represented as % cumulative release of the drug as a function of time, is shown in tabular form below Table 7:

TABLE 7

| Time (min) | % Cumulative Release of Drug |
|---|---|
| 15 | 0.3 |
| 30 | 1.1 |
| 45 | 2.1 |
| 60 | 3.2 |
| 120 | 4.3 |
| 135 | 5.9 |
| 150 | 6.3 |
| 165 | 6.8 |
| 180 | 7.4 |
| 240 | 10.8 |
| 390 | 13.2 |

Example 6

Zotarolimus, a tetrazole analog of rapamycin, has been shown to possess anti-restenosis activity in swine coronary stent-induced injury (Touchard A G, Burke S E, Toner J L, Cromack K and Schwartz R S. *Zotarolimus-eluting stents reduce experimental coronary artery neointimal hyperplasia after 4 weeks. Eur Heart J.* 27:988-993, 2006). Delivered from the Biocompatibles BiodivYsio PC Coronary Stents in Porcine Coronary Arteries, Technical Report, Mayo Clinic and Foundation, Rochester, Minn.) and rat balloon angioplasty (Gregory, C. Summary of Study Evaluating Effects of zotarolimus in a Rat Model of Vascular Injury) models. The objective of this example was to assess the safety and pharmacokinetics (PK) of escalating single intravenous (IV) doses of zotarolimus in healthy males.

In the present, first-time-in-man study, the safety and pharmacokinetics of zotarolimus were investigated following intravenous bolus administration of zotarolimus over a 100 to 900 µg dose range. The intravenous bolus dose administration would mimic the most rapid unexpected release of zotarolimus from drug-coated stents in vivo.

This was a Phase 1, single escalating dose, double-blind, randomized, placebo-controlled, single-center study. Sixty (60) adult healthy males were divided into 5 IV dose groups of 100, 300, 500, 700, and 900 µg. Demographic information for the subjects is summarized in Table 8.

TABLE 8

Demographic Summary for All Subjects

| | Mean ± SD (N = 60) | Min-Max |
|---|---|---|
| Age (years) | 32.6 ± 7.1 | 19-44 |
| Weight (kg) | 80.0 ± 10.6 | 62-104 |
| Height (cm) | 180.5 ± 7.2 | 160-195 |
| Race | 60 Caucasians (100%) | |

Subjects were randomly assigned to receive a single intravenous dose of zotarolimus or a matching intravenous placebo under fasting conditions, as shown in the dosing scheme shown in Table 9.

TABLE 9

| Treatment Group | Double-blind Treatment | Number of Subjects |
|---|---|---|
| I | 100 µg zotarolimus/Placebo | 8/4 |
| II | 300 µg zotarolimus/Placebo | 8/4 |
| III | 500 µg zotarolimus/Placebo | 8/4 |
| IV | 700 µg zotarolimus/Placebo | 8/4 |
| V | 900 µg zotarolimus/Placebo | 8/4 |

Higher doses were administered after evaluating the safety data from the preceding lower dose groups. The treatment groups were separated by at least 7 days. For safety reasons, each treatment group was divided into two cohorts of six subjects and the doses of the two cohorts of a group were separated by at least 1 day.

Doses were administered as IV bolus over 3 minutes, with 8 subjects. Four subjects received zotarolimus and 4 subjects received placebo in each dose group. Blood was sampled for 168 hours and concentrations of zotarolimus measured using LC-MS/MS with a LOQ of 0.20 ng/mL Seven (7)-mL blood samples were collected by venipuncture into evacuated collection tubes including edetic acid (EDTA) prior to dosing (0 hour) and at 0.083 (5 min), 0.25, 0.5, 1, 2, 4, 8, 12, 16, 24, 36, 48, 72, 96, 120, 144, and 168 hours after dosing on Study Day 1.

Blood concentrations of zotarolimus were determined using a validated liquid/liquid extraction HPLC tandem mass spectrometric method LC-MS/MS). (Ji, Q C, Reimer M T, El-Shourbagy, T A.: *A 96-well liquid-liquid extraction HPLC-MS/MS method for the quantitative determination of ABT-578 in human blood samples*, J. of Chromatogr. B 805, 67-75 (2004).) The lower limit of quantification of zotarolimus was 0.20 ng/mL using 0.3 mL blood sample. AU calibration curves had coefficient of determination ($r^2$) values greater than or equal to 0.9923.

Safety was evaluated based on adverse event, physical examination, vital signs, ECG, injection site and laboratory tests assessments.

Pharmacokinetic parameter values of zotarolimus were estimated using noncompartmental methods. These parameters included: concentration at 5-minutes zotarolimus post-dose ($C_5$), dose-normalized $C_5$, elimination rate constant ($\beta$), half-life ($t_{1/2}$), the area under the blood concentration vs. time curve from time 0 to time of the last measurable concentration ($AUC_{0-last}$), dose-normalized $AUC_{0-last}$, the area under the blood concentration vs. time curve extrapolated to infinite time ($AUC_{0-inf}$), dose-normalized $AUC_{0-inf}$, total clearance (CL), and volume of distribution ($Vd_\beta$).

Figure 4:
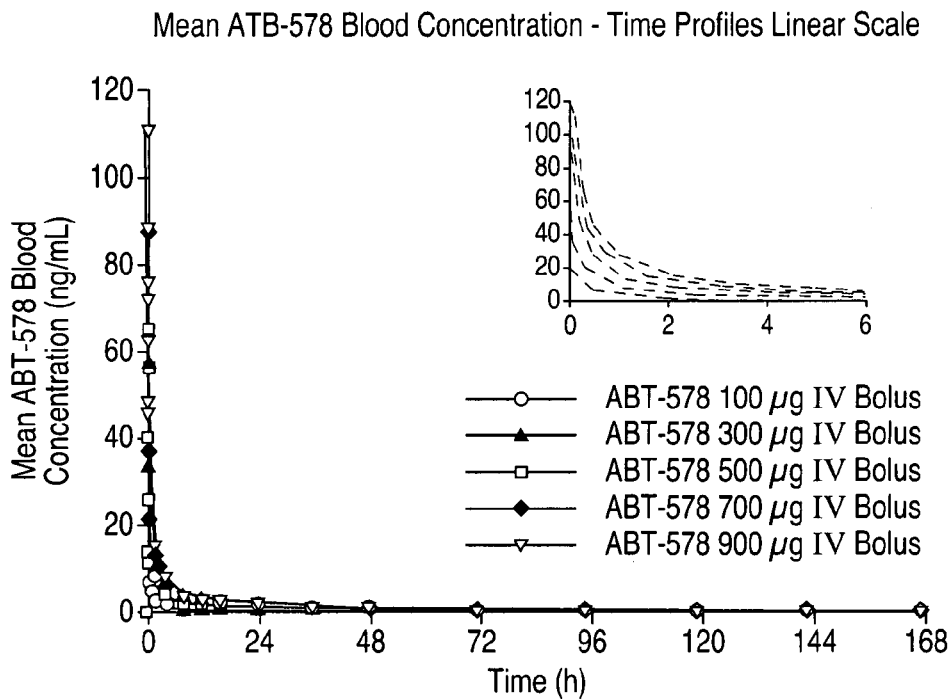
FIG. 4 shows on a linear scale mean blood-concentration—time plot for single escalating i.v. doses of zotarolimus in humans.
Figure 5:
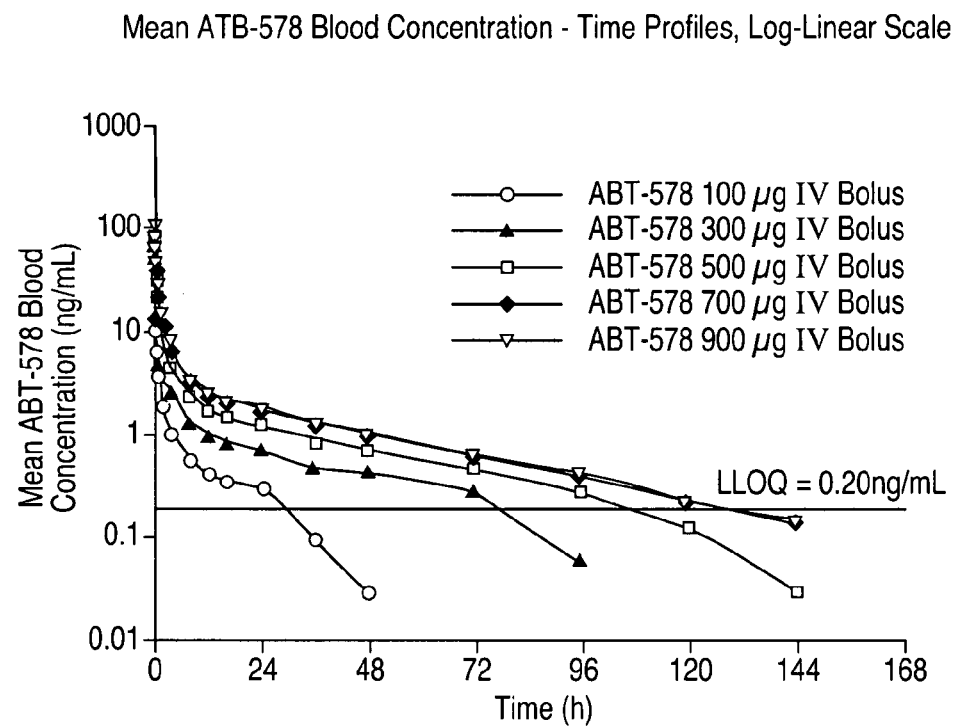
FIG. 5 shows on a log-linear scale mean blood concentration-time plots, following single escalating i.v. doses of zotarolimus in humans.

Mean blood concentration-time plots, following intravenous doses of zotarolimus are presented in FIGS. 4 and 5 on linear scale and log-linear scale, respectively.

Mean±SD pharmacokinetic parameters of zotarolimus after administration of each of the two regimens are shown in Table 10.

TABLE 10

Mean ± SD Pharmacokinetic Parameters of Zotarolimus

| Pharmacokinetic Parameters | Dose of Zotarolimus | | | | |
|---|---|---|---|---|---|
| | 100 µg (N = 8) | 300 µg (N = 8) | 500 µg (N = 8) | 700 µg (N = 8) | 900 µg (N = 8) |
| $C_5$ (ng/mL) | 13.48 ± 2.87 | 36.71 ± 9.82* | 56.50 ± 27.54* | 88.73 ± 5.00 | 110.78 ± 15.91* |
| $C_5$/Dose (ng/mL/µg) | 0.13 ± 0.03 | 0.12 ± 0.03 | 11 ± 0.05 | 0.13 ± 0.01 | 0.12 ± 0.02 |
| $AUC_{0-last}$ (ng · h/mL) | 24.57 ± 5.89 | 77.79 ± 13.70 | 146.04 ± 32.39 | 207.92 ± 19.44 | 240.80 ± 19.19 |
| $AUC_{0-last}$/Dose (ng · h/mL/µg) | 0.25 ± 0.06 | 0.26 ± 0.05 | 0.29 ± 0.06 | 0.30 ± 0.03 | 0.27 ± 0.02 |
| $AUC_{0-inf}$ (ng · h/mL) | 35.28 ± 6.15 | 91.17 ± 14.68 | 162.44 ± 29.58 | 221.77 ± 19.60 | 254.47 ± 17.60 |
| $AUC_{0-inf}$/Dose (ng · h/mL/µg)# | 0.35 ± 0.06 | 0.30 ± 0.05 | 0.32 ± 0.06 | 0.32 ± 0.03 | 0.28 ± 0.02 |
| $\beta$ (1/h)# | 0.027 ± 0.006 | 0.019 ± 0.002 | 0.017 ± 0.003 | 0.020 ± 0.001 | 0.018 ± 0.002 |
| $t_{1/2}$(h)$ | 26.0 ± 6.0 | 35.9 ± 4.6 | 40.2 ± 7.8 | 35.0 ± 2.4 | 39.0 ± 3.9 |
| CL (L/h) | 2.90 ± 0.44 | 3.36 ± 0.50 | 3.17 ± 0.58 | 3.18 ± 0.28 | 3.55 ± 0.24 |
| $Vd_\beta$ (L)# | 113 ± 23 | 175 ± 23 | 190 ± 49 | 161 ± 15 | 202 ± 29 |

$Harmonic mean ± pseudo-standard deviation; evaluations of $t_{1/2}$ were based on statistical tests for $\beta$
A >10% sampling time deviation occurred for the 5-minutes sample for Subjects 201, 304, and 512; $C_5$ concentrations for these subjects were not calculated. (N = 7)
Statistically significant monotonic trend with dose To investigate the questions of dose proportionality and linear pharmacokinetics, an analysis of covariance (ANCOVA) was performed. Subjects were classified by dose level, and body weight was a covariate. The variables analyzed included $\beta$, $Vd_\beta$, dose-normalized $C_5$, and logarithms of dose-normalized $AUC_{0-last}$ and dose-normalized $AUC_{0-inf}$. The primary test of the hypothesis of invariance with dose was a test on dose-level effects with good power for a monotonic function of dose. In addition, the highest and lowest dose levels were compared within the framework of the ANCOVA.

Figure 6:
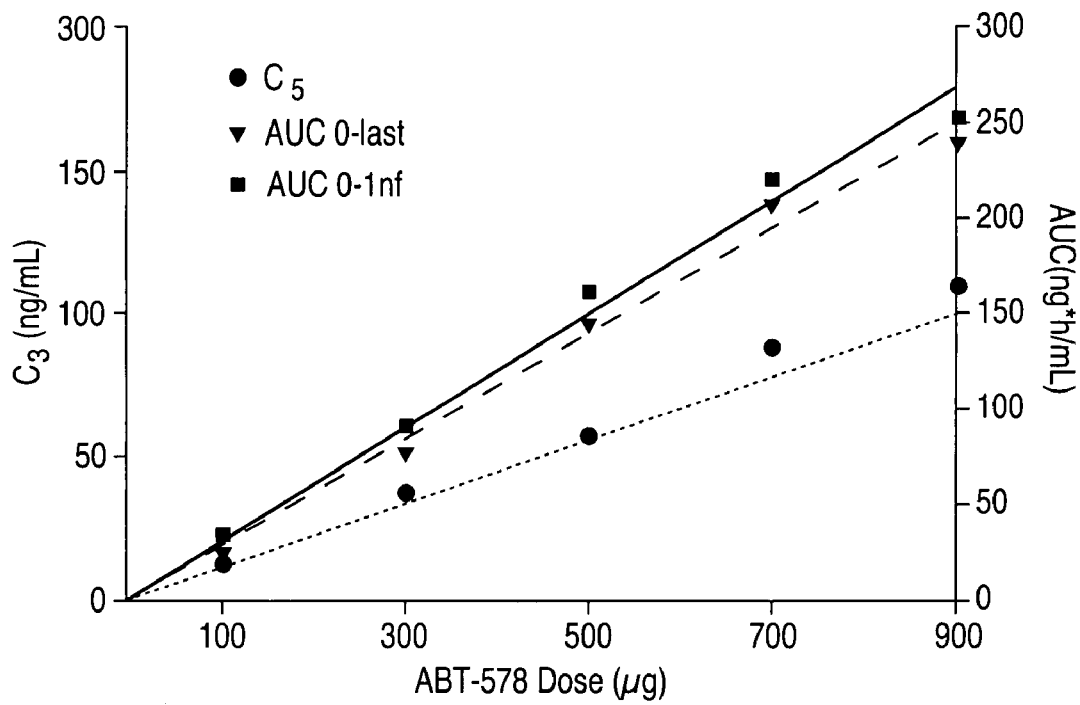
FIG. 6 shows dose proportionality of zotarolimus $C_{max}$ and AUC parameters following single escalating intravenous doses in humans.

FIG. 6 depicts the dose proportionality of zotarolimus $C_{max}$, $AUC_{0-last}$, and $AUC_{0-inf}$. As can be seen in this figure, no statistically significant monotonic trend was observed with dose normalized $C_{max}$, and $AUC_{0-last}$ suggesting a dose proportional increase in these parameters. A statistically significant monotonic trend with dose was observed for the dose-normalized $AUC_{0-inf}$ of zotarolimus (p=0.0152). However, a pairwise comparison of dose-normalized $AUC_{0-inf}$ across all groups showed that only 100 µg dose-normalized $AUC_{0-inf}$ was statistically significant different from that of 900 µg and 300 µg p=0.0032 and p=0.0316, respectively). A statistically significant monotonic trend was also observed with $\beta$. This departure could be due to slight overestimation of $\beta$ with the 100 µg dose group. The mean zotarolimus $C_5$ (concentration at 5 minutes) and $AUC_{0-inf}$ increased proportionally with dose, as shown in Table 11.

TABLE 11

| Pharmacokinetic Parameters | Dose (μg) (N = 8) | | | | |
|---|---|---|---|---|---|
| | 100 | 300 | 500 | 700 | 900 |
| $C_5$ (ng/mL) | 13.48 ± 2.87 | 36.71 ± 9.82 | 56.50 ± 27.54 | 88.73 ± 5.00 | 110.78 ± 15.91 |
| $AUC_{0\text{-}inf}$ (ng · h/mL) | 35.28 ± 6.15 | 91.17 ± 14.68 | 162.44 ± 9.58 | 221.77 ± 19.60 | 254.47 ± 17.60 |
| CL (L/h) | 2.90 ± 0.44 | 3.36 ± 0.50 | 3.17 ± 0.58 | 3.18 ± 0.28 | 3.55 ± 0.24 |

The mean half-life ranged between 26.0-40.2 h over the studied doses and was not significantly different over the 300-900 μg dose range. Zotarolimus was well tolerated at all doses and no clinically significant physical examination results, vital signs or laboratory measurements were observed.

Safety

The most common treatment-emergent adverse events (reported by two or more subjects in any one treatment group) associated with zotarolimus were injection site reaction and pain.

The majority of the adverse events was mild in severity and resolved spontaneously.

There were no serious adverse events reported in this study.

There were no clinically significant changes in physical examination findings, vital signs, clinical laboratory or ECG parameters during the study.

Conclusion

The pharmacokinetics of IV Zotarolimus are dose-proportional over the 100-900 μg dose range with respect to $C_5$ and $AUC_{0\text{-}inf}$. Overall, the pharmacokinetics of Zotarolimus were essentially linear across the 100 μg to 900 μg dose range as illustrated by the dose proportional increases in $C_5$, $AUC_{0\text{-}last}$, and $AUC_{0\text{-}inf}$. Single IV bolus doses up to 900 μg were administered without safety concerns.

Mean elimination half-life of zotarolimus ranged from 26.0 to 40.2 hours over the studied dose range. The mean clearance and volume of distribution ranged from 2.90 to 3.55 L/h and 113 to 202 L, respectively. The observed departure from linear kinetics for P and, to a significant extent, for $Vd_\beta$ was due to an overestimation of P for the 100 μg dose group.

Zotarolimus in single doses of 100 to 900 μg were generally well tolerated by the subjects.

Example 7

The present study was designed to evaluate the pharmacokinetics of zotarolimus following multiple dosing and to assess its safety while maximizing systemic exposure of healthy subjects. The primary goal was to achieve a total exposure of zotarolimus significantly above the anticipated levels of the drug eluted from coated stents. The study investigated pharmacokinetics and safety of zotarolimus in a Phase 1, multiple dose-escalation study following multiple intravenous infusions of 200, 400 and 800 μg doses, every day for fourteen consecutive days in healthy subjects.

Methods

Phase 1, multiple-escalating dose, double-blind, placebo-controlled, randomized study. Seventy-two subjects equally divided in 3 once-daily (QD) regimens (200, 400 or 800 μg QD with 16 active and 8 placebo per regimen) were administered a 60-minute QD IV infusion of zotarolimus for 14 consecutive days. Blood samples were collected over 24 hours following the first dose, before dosing on days 10, 11, 12, 13, and for 168 hours following Day 14 dose. Urine samples were collected over 24 hours on days 1, 14, 16, 18 and 20. Blood and urine zotarolimus concentrations were determined using a validated LC/MS/MS method. Pharmacokinetic parameters were determined by compartmental analysis. All Day-$AUC_{0\text{-}\infty}$ (area under blood concentration-time curve from time 0 to infinity including all 14 doses) was calculated. Dose and time-linearity and achievement of steady-state were evaluated. Fraction of drug eliminated in urine was determined.

Seventy-two (72) male and female subjects in general good health were enrolled in this study. Demographic information is summarized in Table 12.

TABLE 12

Demographic Summary for All Randomized Group I, Group II and Group III Subjects

| | Mean ± SD (N = 72) | Min-Max |
|---|---|---|
| Age (years) | 36.9 ± 7.8 | 19-59 |
| Weight (kg) | 78.0 ± 8.2 | 61-97 |
| Height (cm) | 178.5 ± 6.3 | 163-193 |
| Sex | 70 Males (97%), 2 Females (3%) | |
| Race | 71 White (99%), 1 Black (1%) | |

Subjects were randomized at two different sites to three groups (Groups I, II and III) as shown in Table 13. Within each group, subjects were equally divided at the two study sites with each site enrolling 12 subjects (zotarolimus, eight subjects; placebo four subjects). The dosing scheme within each dose group is presented below:

TABLE 13

Dosing Scheme

| Group | Number of Subjects | Double-Blind IV Treatment |
|---|---|---|
| I | 16[+] | 200 μg zotarolimus over 60 min QD for 14 days |
| | 8 | Placebo over 60 min QD for 14 days |
| II | 16 | 400 μg zotarolimus over 60 min QD for 14 days |
| | 8 | Placebo over 60 min QD for 14 days |
| III | 16 | 800 μg zotarolimus over 60 min QD for 14 days |
| | 8 | Placebo over 60 min QD for 14 days |

[+]Subject 2112 prematurely discontinued the study; subject withdrew consent on Study Day 19.

Subjects received, under fasting conditions, a single 60-minute daily (QD) intravenous infusion of 200, 400, or 800 μg of zotarolimus or a matching intravenous infusion of placebo for Groups I, II and III, respectively on Study Days 1 through 14. The drug was administered via a syringe pump connected to a y-site device, which also infused 125-150 mL of 5% aqueous dextrose solution (D5W) over 60 minutes. The groups were dosed sequentially with at least 7 days separating the last dose of the previous group and the first dose of the next group during which time safety data from the previous group was analyzed. Dose escalation was dependent on the safety analysis of the lower dose group.

Five (5)-mL blood samples were collected in potassium EDTA containing tubes to evaluate zotarolimus concentrations prior to dosing (0 hour), and at 0.25, 0.5, 1.0, 1 hour 5 min, 1.25, 1.5, 2, 3, 4, 8, 12, 18 and 24 hours after starting infusion on Study Days 1 and 14. Additional samples were collected at 36, 48, 72, 96, 120, 144 and 168 hours after starting infusion on Study Day 14 and before dosing on Days 10, 11, 12 and 13. Urine was collected in containers without preservatives over the following intervals: 0 to 6, 6 to 12, 12 to 18 and 18 to 24 hours after starting the infusion on Study Days 1, 14, 16, 18 and 20.

Blood and urine concentrations of zotarolimus were determined using a validated liquid/liquid extraction HPLC tandem mass spectrometric method (LC-MS/MS). The lower limit of quantification of zotarolimus was 0.20 ng/mL using 0.3 mL blood sample and 0.50 ng/mL using 0.3 mL urine sample.

Safety was evaluated based on adverse event, physical examination, vital signs, ECG, injection site and laboratory tests assessments Results Zotarolimus blood concentration-time data for all subjects were described by a three compartment open model with first order elimination. Over the studied regimens, the range of mean compartmental pharmacokinetic parameters were: CL 4.0-4.6 L/h; $V_1$ 11.3-13.1 L; $V_{ss}$ 92.5-118.0 L, and terminal elimination $t_{1/2}$ 24.7-31.0 h. Zotarolimus pharmacokinetics were consistent with dose linearity over the studied regimens, on days 1 and 14. The pharmacokinetic model simultaneously fit data for days 1 and 14, indicating time-linear pharmacokinetics. All Day-$AUC_{0-\infty}$ for the studied regimens ranged from 677-2395 ng·hr/mL. On average, 0.1% of zotarolimus dose was recovered in the urine within a 24-hour period post-dose.

Pharmacokinetic and Statistical Analysis

The pharmacokinetic parameter values of zotarolimus were estimated for individual subjects using compartmental analysis. Data from the first dose on Study Day 1, the last dose on Study Day 14 and the trough concentrations on Study Days 10, 11, 12 and 13 were simultaneously modeled for each individual subject. Parameters determined were: volume of the central compartment ($V_1$), terminal elimination rate constant gamma), clearance (CL), volume of distribution at steady state ($V_{ss}$), half-life ($t_{1/2}$), maximum concentration ($C_{max}$), time of maximum concentration ($T_{max}$), area under the blood concentration versus time curve for Day 14 ($AUC_\tau$) and corresponding dose normalized $C_{max}$ and $AUC_\tau$. The optimal model for each individual was used to predict the individual's concentration-time profile over a 14-day period to estimate the chronic exposure over the study duration, i.e. $C_{max}$ and All Day-$AUC_{0-\infty}$ (Area under the predicted blood concentration-time profile from time 0 to infinity taking into account all 14 doses in the study).

To assess dose proportionality for the Study Day 14 dose an analysis of covariance (ANCOVA) for the logarithm of dose-normalized $C_{max}$, dose-normalized AUC, and terminal elimination rate constant ☐ was performed. The center and the dose were factors and body weight was a covariate. To address the question of whether steady state was reached, a repeated measures analysis, with center and dose level as factors, was performed on the dose-normalized pre-dose concentrations of Study Days 10-14.

Pharmacokinetics

Figure 7:
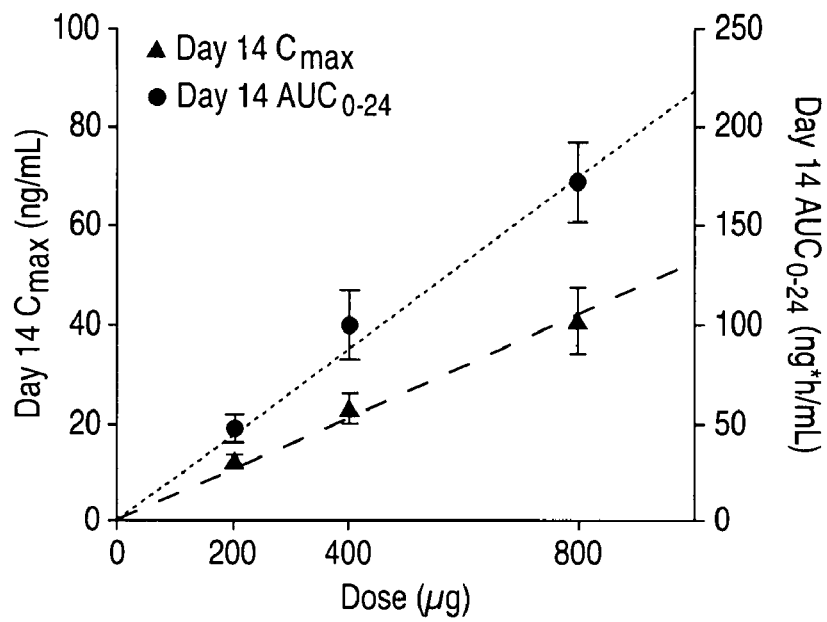
FIG. 7 shows mean blood concentration-time plots of zotarolimus following multiple intravenous doses in humans.

Zotarolimus blood concentration-time data for all subjects were described by a three compartment open model with first order elimination. The mean blood concentrations for zotarolimus for Day 1, Day 14 and Days 1 through 14 are presented in FIG. 7. The mean±SD of pharmacokinetic parameters of zotarolimus are presented in Table 14.

TABLE 14

Mean ± SD Compartmental Pharmacokinetic Parameters of zotarolimus

| Pharmacokinetic Parameters (units) | | 200 μg QD (N = 15) | Dose Groups 400 μg QD (N = 16) | 800 μg QD (N = 16) |
|---|---|---|---|---|
| $V_1$ | (L) | 11.4 ± 1.7 | 11.3 ± 1.0 | 13.1 ± 3.2 |
| Gamma | (h-1) | 0.028 ± 0.005 | 0.022 ± 0.003 | 0.023 ± 0.003 |
| $C_{max}$* | (ng/mL) | 11.2 ± 1.1 | 21.4 ± 2.4 | 38.7 ± 6.3 |
| $C_{max}$/Dose* | (ng/mL/μg) | 0.056 ± 0.006 | 0.053 ± 0.006 | 0.048 ± 0.008 |
| $AUC_\tau$* | (ng·h/mL) | 49.0 ± 6.2 | 104.2 ± 19.0 | 179.5 ± 17.4 |
| $AUC_\tau$/Dose* | (ng·h/mL/μg) | 0.245 ± 0.031 | 0.260 ± 0.047 | 0.224 ± 0.022 |
| $t_{1/2}$$^\$$* | (h) | 24.7 ± 4.6 | 31.0 ± 4.6 | 30.0 ± 4.1 |
| CL* | (L/h) | 4.2 ± 0.6 | 4.0 ± 0.9 | 4.6 ± 0.4 |
| $V_{ss}$* | (L) | 92.5 ± 13.0 | 111.5 ± 21.1 | 118.0 ± 18.7 |

$Harmonic mean ± pseudo-standard deviation
*Secondary predicted parameters

As no bias in the observed versus predicted diagnostic plots over the studied regimens was observed, the ranges of the compartmental pharmacokinetic parameters over the studied dose regimens were very narrow and no meaningful trend over the studied dose regimens in the secondary parameters was observed; dose linearity was inferred for zotarolimus over the studied dose regimens.

Figure 8A:
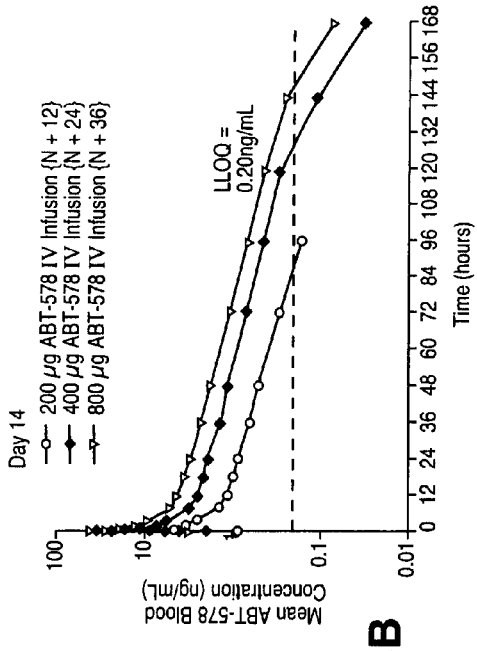
FIG. 8 shows mean zotarolimus blood concentration-time profiles for 200, 400 and 800 µg QD (daily) dose groups on Day 1 (FIG. 8*a*), Day 14 (FIG. 8*b*), and Days 1-14 (FIG. 8*c*).
Figure 8B:
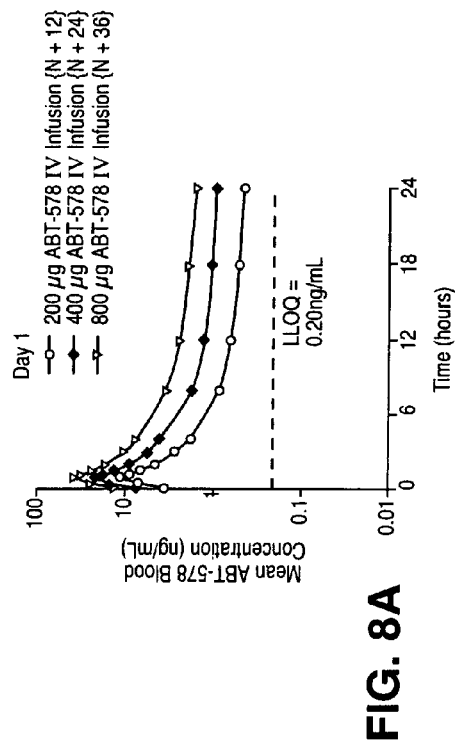
Figure 8C:
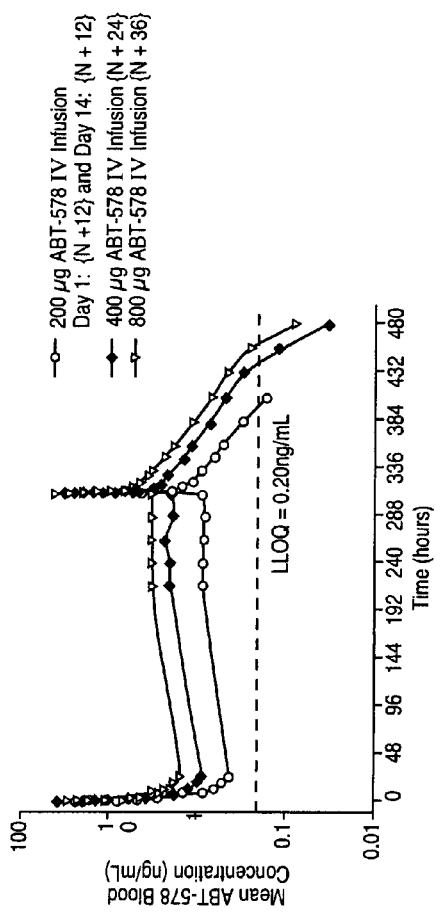

The following figure depicts the dose proportionality in zotarolimus Day 14 $C_{max}$ and $AUC_{0-24h}$ FIGS. 8a, 8b and 8c show mean zotarolimus blood concentration-time profiles for the 200, 400 and 800 μg QD dose groups on Day 1, Day 14 and Days 1-14, respectively. For each dose group, the model adequately described the data on Day 1 as well as Day 14 and in between as exemplified in FIG. 9 (example of mean observed and predicted blood concentration versus time plots upon fitting 800 μg QD dose group data). The excellent fit of the observed zotarolimus concentration-time data over Days 1 through 14 by a 3-compartment model that assumes linear kinetics indicates that zotarolimus exhibits time invariant clearance.

Figure 9:
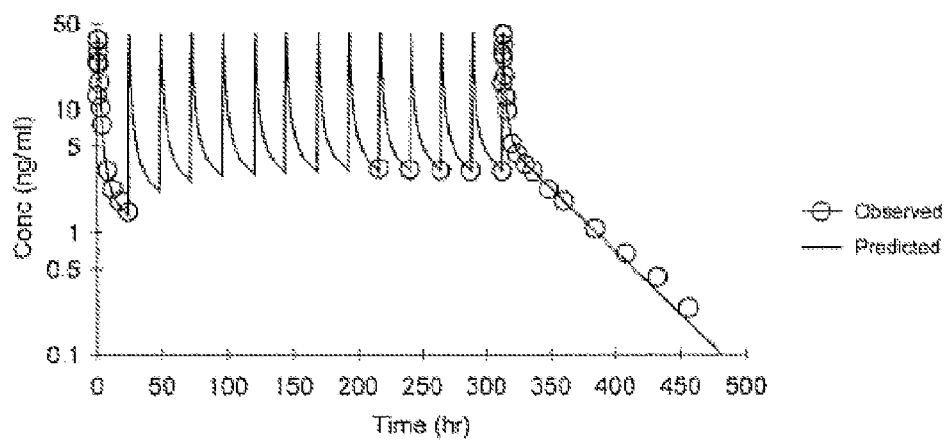
FIG. 9 shows observed zotarolimus concentration-time data over days 1 through 14 for 800 µg QD dose group.

As shown in FIG. 9, no statistical differences were observed in the dose-normalized pre-dose concentrations of Study Days 10-14.

The median $C_{max}$ for the 200, 400 and 800 μg QD dose groups was 11.4, 22.1 and 38.9 ng/mL, respectively. The corresponding median All Day -$AUC_{0-\infty}$ was 677, 1438, and 2395 ng·h/mL, respectively.

The fraction of the zotarolimus dose eliminated in the urine was calculated for the 800 μg QD dose group. On average, approximately 0.1% of zotarolimus was recovered in the urine within a 24-hour period on Day 1 and Day 14.

Safety

The most common treatment-emergent adverse events associated with zotarolimus were pain, headache, injection site reaction, dry skin, abdominal pain, diarrhea and rash. The majority of the adverse events were mild in severity and resolved spontaneously. There were no serious adverse events reported in this study. Specifically, no subject displayed any clinical or biochemical evidence of immunosuppression, QTc prolongation or clinically significant adverse events.

Conclusions

Zotarolimus pharmacokinetics were dose proportional and time invariant when administered intravenously for 14 consecutive days, over the studied dose regimens.

Steady state for QD dosing of zotarolimus was reached by Day 10, the day on which the first trough samples were measured.

Renal excretion is not a major route of elimination for zotarolimus as approximately 0.1% of the dose was excreted as unchanged drug in the urine per day.

Zotarolimus is generally well tolerated when given in multiple doses of 200, 400, and 800 μg for 14 consecutive days.

Example 8

Anti-Inflammatory Effects of Zotarolimus and Dexamethasone Individually

Inflammatory responses following percutaneous transluminal coronary angioplasty (PTCA) and stenting have been suggested to play a role in the vascular remodeling associated with restenosis {R. G. Macdonald, R. S. Panush and C. J. Pepine, Rationale for use of glucocorticoids in modification of restenosis after percutaneous transluminal coronary angioplasty, Am J Cardiol, 60, 3, 1987, 56B-60B; J. S. Forrester, M. Fishbein, R. Helfant and J. Fagin, A paradigm for restenosis based on cell biology: clues for the development of new preventive therapies, J Am Coll Cardiol, 17, 3, 1991, 758-69; S. P. Karas, E. C. Santoian and M. B. Gravanis, Restenosis following coronary angioplasty, Clin Cardiol, 14, 10, 1991, 791-801; P. Libby and S. K. Clinton, Cytokines as mediators of vascular pathology, Nouv Rev Fr Hematol, 34 Suppl, 1992, S47-53}. A number of cell types contribute to this response including circulating monocytes, macrophages, neutrophils, eosinophils, platelets, vascular smooth muscle and endothelial cells {R. G. Macdonald, R. S. Panush and C. J. Pepine, Rationale for use of glucocorticoids in modification of restenosis after percutaneous transluminal coronary angioplasty, Am J Cardiol, 60, 3, 1987, 56B-60B}. Activation of immune cells following PTCA results in cytokine/chemokine production and the recruitment of circulating monocytes to the vascular wall. Three important cytokines, produced by monocytes are tumor necrosis factor α (TNFα), monocyte chemoattractant protein I (MCP-1), and interleukin 6 (IL-6). They have been shown to increase following PTCA and increased levels of MCP-1 and IL-6 are associated with an increased incidence of restenosis {Y. Hojo, U. Ikeda, T. Ibatsuki, O. Mizuno, H. Fukazawa, H. Fujikawa and K. Shimada, Chemokine expression in coronary circulation after coronary angioplasty as a prognostic factor for restenosis, Atherosclerosis, 156, 1, 2001, 165-70; F. Cipollone, M. Marini, M. Fazia, B. Pini, A. Jezzi, M. Reale, L. Paloscia, G. Materazzo, E. D'Annunzio, P. Conti, F. Chiarelli, F. Cuccurullo and A. Mezzetti, Elevated circulating levels of monocyte chemoattractant protein-1 in patients with restenosis after coronary angioplasty, Arterioscler Thromb Vasc Biol, 21, 3, 2001, 327-34}. Tumor necrosis factor α (TNFα) is a pro-inflammatory cytokine produced by monocytes and tissue macrophages, cell types which have been implicated in the pathophysiology of restenosis (Moreno P R, Bernardi V H, Lopez-Cuellar J, Newell J B, McMellon C, Gold H K, Palacios I F, Fuster V, Fallon J T. Macrophage infiltration predicts restenosis after coronary intervention in patients with unstable angina. Circ, 94(12), 1996: 3098-102). TNFα levels have been shown to be increased in humans with in-stent restenosis and levels of this cytokine are increased following angioplasty (Kozinski M, Krzewina-Kowalska A, Kubica J, Zbikowska-Gotz M, Dymek G, Piasecki R, Sukiennik A, Grzesk G, Bogdan M, Chojnicki M, Dziedziczko A, Sypniewska G. Percutaneous coronary intervention triggers a systemic inflammatory response in patients treated for in-stent restenosis—comparison with stable and unstable angina: Inflammation Research: 54: 2005:187-93). Anti-TNFα antibodies loaded onto a stent have been shown to reduce PCNA, a marker of cell proliferation in human saphenous vein cultures suggesting that blocking TNFα effects may result in the reduction of neointimal hyperplasia (Javed Q, Swanson N, Vohra H, Thurston H, Gershlick A H.; Tumor necrosis factor-alpha antibody eluting stents reduce vascular smooth muscle cell proliferation in saphenous vein organ culture. Exp Mol Path, 73(2): 2002: 104-11). Furthermore, increasing levels of TNFα can activate cytokine production by vascular smooth muscle and endothelial cells and this may lead to a sustained inflammatory response in the vascular wall.

The glucocorticosteriod dexamethasone has potent anti-inflammatory effects on a number of cell types. Dexamethasone has been proposed as an anti-restenotic agent and is currently used on the Dexamet drug-eluting stent (commercially available in Europe from Abbott Vascular Inc. (check) {D. W. Muller, G. Golomb, D. Gordon and R. J. Levy, Site-specific dexamethasone delivery for the prevention of neointimal thickening after vascular stent implantation, Coron Artery Dis, 5, 5, 1994, 435-42}. However, the effects of the immunosuppressants zotarolimus and sirolimus on the production of these important cytokines by human monocytes were not previously known.

In yet other embodiments, the second drug is a member of the group consisting of small molecules and biologics that reduce inflammatory cytokine activity. In still yet other embodiments, the second drug includes an anti-TNF alpha therapies consisting of the group adalimumab, anti-MCP-1 therapies and CCR2 receptor antagonists, anti-IL-18 therapies, anti-IL-1 therapies, and their salts, esters, prodrugs, and derivatives or any combination thereof.

Experiments were performed to determine the effects of zotarolimus, sirolimus and dexamethasone on the production of TNFα, IL-6 and MCP-1 by activated human monocytes In addition to monocytes and macrophages two other key cell types are involved in the etiology of restenosis, arterial smooth muscle and endothelial cells. These cells are activated and produce cytokines in response to TNFα. To determine the anti-inflammatory effects of dexamethasone, zotarolimus and sirolimus experiments were conducted with human coronary artery endothelial and smooth muscle cells hCaEC & hCaSMC, respectively). The activation of cytokine production by human coronary artery smooth muscle and endothelial cells following TNFα treatment was determined by measuring interleukine-8 (IL-8), MCP-1 and IL-6 production. As shown by the results of the experiments described below, the ability of these compounds to inhibit the production of cytokines supports their use in combination as anti-restenotic agents since these cytokines play a role in the development of restenosis.

Methods

Human monocytes (Cambrex, East Rutherford N.J.) were seeded into 96-well microplates (60,000 cells/well), cultured for 48 hours at 37° C., and then stimulated with bacterial lipopolysaccharide (LPS, 25 or 100 ng/ml) for 24 hours in the presence and absence of test compounds in culture media. After 24 hours, the supernatants were carefully collected and TNFα, IL-6 and MCP-1 levels determined by ELISA. Primary cultures of human coronary artery endothelial and smooth muscle cells were obtained from Cambrex and maintained as described by the vendor. Cells were seeded into 96-well microplates at a concentration of 5000 cells/well (hCaSMC) and 7500 cells/well hCaEC) and allowed to attach. After 24 hours the supernatants were removed and replaced with media containing TNFα (5 ng/ml) in the presence and absence of various concentrations of zotarolimus, dexamethasone or sirolimus. The cells were incubated for 24 hours and the supernatants carefully removed and frozen until measurement. Cytokine levels were measured in the supernatants by sandwich ELISA.

Results and Conclusions

Figure 10:
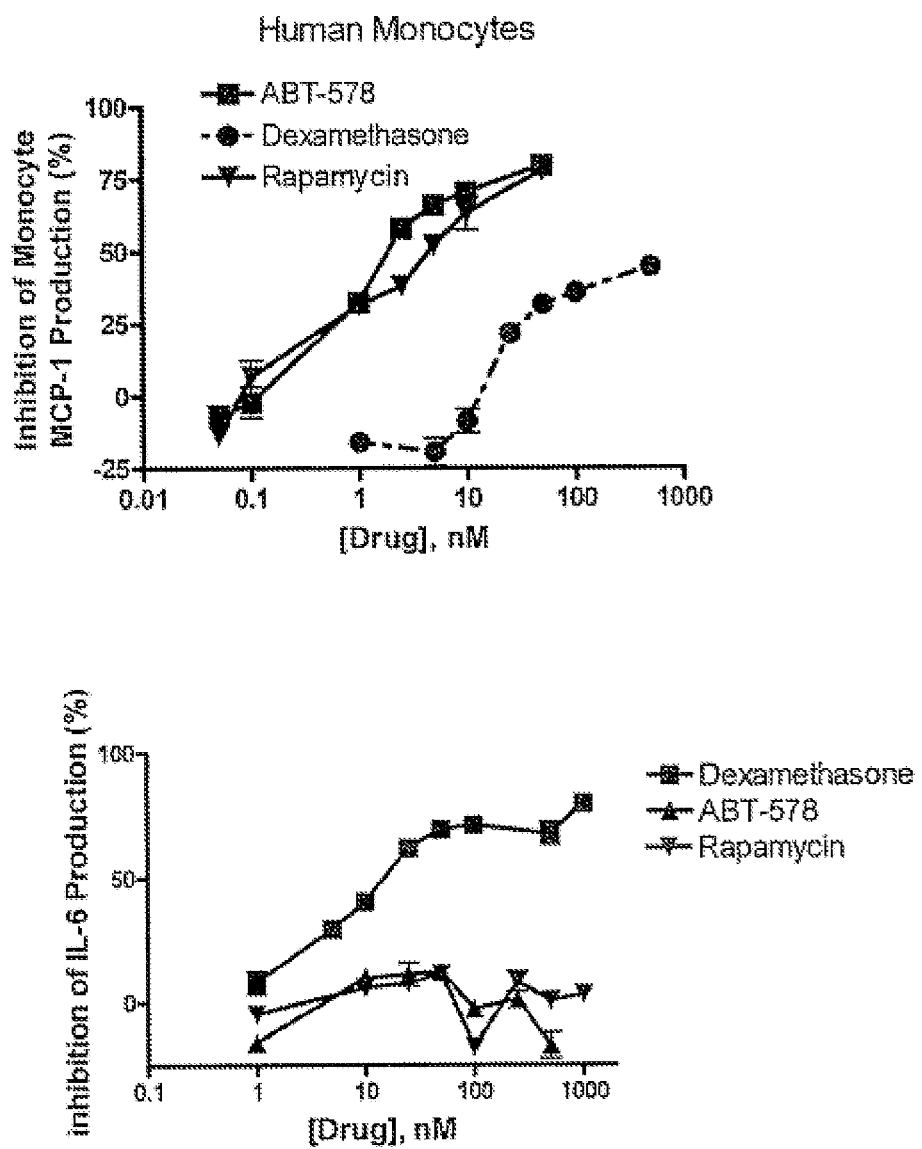
FIGS. 10 and 11 are graphs showing effects of zotarolimus, dexamethasone and paclitaxel on LPS-stimulated MCP-1, IL-6 and TNF-α production by human monocytes in vitro.
Figure 11:
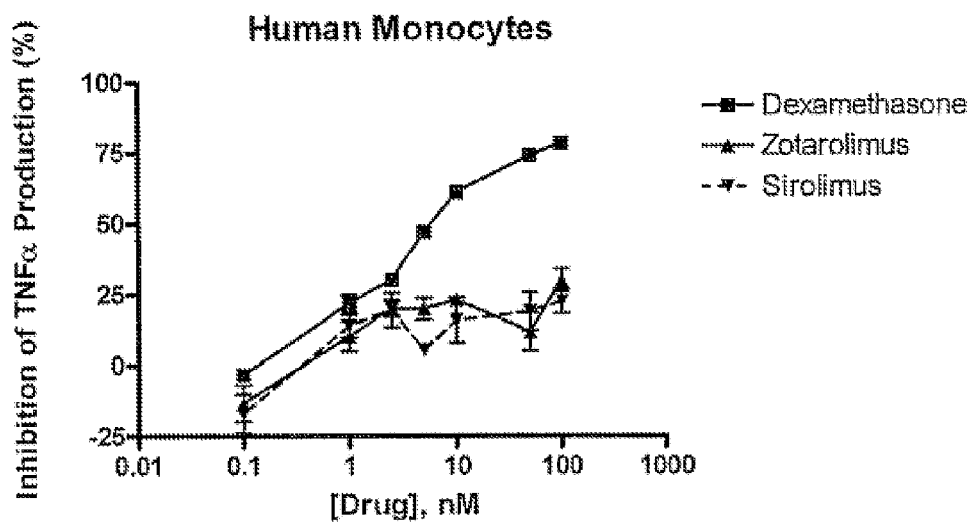

FIG. 10 shows that dexamethasone, zotarolimus and rapamycin all dose-dependently inhibit MCP-1 production by human monocytes in vitro. However, zotarolimus and rapamycin are much more potent and efficacious in this effect than dexamethasone. Conversely, dexamethasone potently blocks the production of TNFα and IL-6 and these effects are not demonstrated by either zotarolimus or rapamycin (FIGS. 10 and 11). In hCaSMC the only agent demonstrating activity was dexamethasone which dose-dependently inhibits cytokine production. Dexamethasone blocks hCaSMC MCP-1 production by 57.2%, IL-6 by 65.7% and IL-8 by 68.4%. The data for all three cell types are summarized in Table 15. None of the agents tested inhibit cytokine production by hCaEC by 50% compared to controls. Since the blockade of the production of all three cytokines, (TNFα, MCP-1 and IL-6) is a beneficial anti-inflammatory effect in the prevention of restenosis, these data support the combined use of zotarolimus and dexamethasone.

TABLE 15

Summary of the Anti-inflammatory Effects of Dexamethasone

| Cell Type | Maximal Inhibitory Activity | | |
|---|---|---|---|
| | Dexamethasone | Zotarolimus | Sirolimus |
| Monocytes | | | |
| IL-6 | +++ | – | – |
| MCP-1 | + | +++ | +++ |
| TNF | +++ | – | – |
| hCaEC | | | |
| IL-6 | – | – | – |
| Il-8 | – | – | – |
| MCP-1 | – | – | – |
| hCaSMC | | | |
| IL-6 | + | – | – |
| Il-8 | + | – | – |
| MCP-1 | + | – | – |

– indicates maximal inhibitory activity less than 50% of control;
+ indicates maximal inhibitory activity of 50-75% of control;
+++ indicates maximal inhibitory activity of 75-100% of control Example 9

Antiproliferative Activity of Zotarolimus and Dexamethasone

Dexamethasone has been proposed as an anti-restenotic agent and is currently used on the Dexamet drug-eluting stent (commercially available in Europe from Abbott Vascular Devices). Dexamethasone has previously been shown to be a potent hCaSMC, but not hCaEC, antiproliferative agent, (Li L, Burke, S E, Chen, Y-C J. *Comparison of drugs in inhibiting human smooth muscle and endothelial cell proliferation*.: Abbott Laboratories Corporate Technology Exchange Poster Presentations; Oct. 27, 2003: R. Voisard, U. Seitzer, R. Baur, P. C. Dartsch, H. Osterhues, M. Hoher and V. Hombach, *Corticosteroid agents inhibit proliferation of smooth muscle cells from human atherosclerotic arteries in vitro*, Int J Cardiol, 43, 3, 1994, 257-67). In addition to its antiproliferative activity, dexamethasone has potent anti-inflammatory activity. Inflammation following stent implantation has been proposed to promote restenosis and agents which interfere with the vascular inflammatory response may attenuate restenosis P. Libby and S. K. Clinton, *Cytokines as mediators of vascular pathology*, Nouv Rev Fr Hematol, 34 Suppl, 1992, S47-53).

Experiments were performed to investigate interactions between zotarolimus and the corticosteroid dexamethasone. The effect of dexamethasone on the antiproliferative activity of zotarolimus in human coronary artery smooth muscle (hCaSMC) and endothelial cells hCaEC) was determined using an in vitro proliferation assay. The proliferation and migration of vascular smooth muscle cells into the vascular neointima is a characteristic pathologic response seen in restenotic lesions (A. Lafont and P. Libby, The smooth muscle cell: sinner or saint in restenosis and the acute coronary syndromes? J Am Coll Cardiol, 32, 1, 1998, 283-5). As a result, in vitro assays which specifically measure the antiproliferative activity of candidate anti-restenotic compounds on human coronary artery smooth muscle and endothelial cells should predict potential anti-restenotic activity in vivo. The tritium incorporation assay is an accurate and sensitive method used in the art to determine cell number and proliferation. Compounds or combinations of compounds which attenuate growth factor-mediated human coronary artery smooth muscle cell hCaSMC) proliferation, as measured by the tritium incorporation assay in vitro, are candidate anti-restenotic agents. This assay was employed to determine if agents which demonstrate antiproliferative activity alone also demonstrate similar activity in combination.

Figure 12:
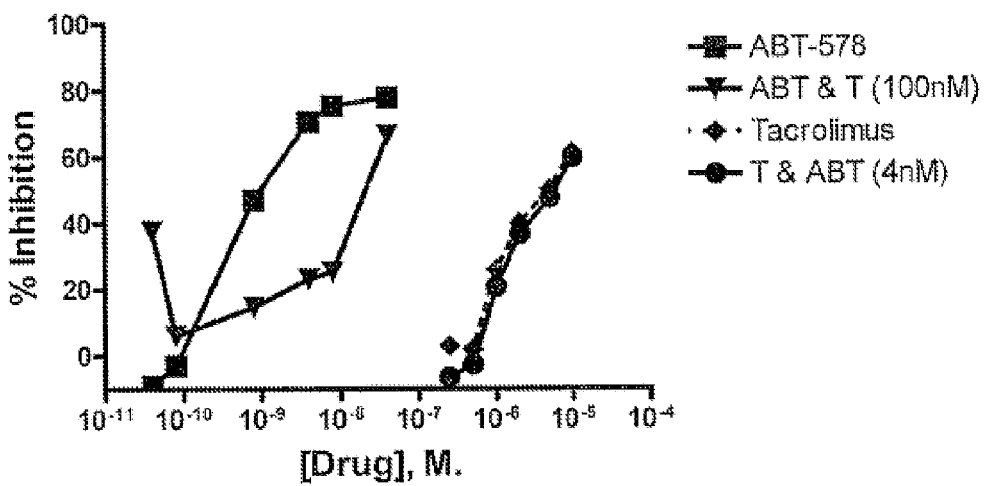
FIG. 12 is a graph showing the attenuation of the anti-proliferative activity of zotarolimus in the presence of tacrolimus. shows that tacrolimus blocks the anti-proliferative activity of zotarolimus in smooth muscle cells in retro.

Furthermore, agents which demonstrate low potency antiproliferative activity may block the activity of more potent antiproliferative agents when administered in combination. The attenuation of zotarolimus's antiproliferative activity by tacrolimus is a clear example of this effect (FIG. 12). As can be seen in the figure, tacrolimus ("T") blocked the antiproliferative activity of zotarolimus in hCaSMC. Tacrolimus (100 nM) increased the IC50 of zotarolimus and the presence of tacrolimus (250 nM or greater) completely blocked the activity of zotarolimus (4 nM). Both zotarolimus and tacrolimus bind the common receptor FKBP-12, although binding of each affects distinct signaling pathways.

To determine the potential anti-restenotic activity of combinations of zotarolimus and dexamethasone, the proliferation of hCaSMC and hCaEC was measured in the presence of each single compound and in combination.

Dexamethasone suppresses the synthesis of key proteins required for cell division in some cell types and is a potent anti-inflammatory (Voisard R, Seitzer U, Baur R, et al. Corticosteroid agents inhibit proliferation of smooth muscle cells from human atherosclerotic arteries in vitro. *Int J Cardiol*. Mar. 1, 1994; 43(3):257-267; N. Baghdassarian, A. Peiretti, E. Devaux, P. A. Bryon and M. French, Involvement of p27Kip1 in the G1- and S/G2-phase lengthening mediated by glucocorticoids in normal human lymphocytes, Cell Growth Differ, 10, 6, 1999, 405-12). Zotarolimus, like rapamycin, blocks cyclin-dependent kinase via mTOR inhibition and inhibits cell cycle progression at the G1-S phase (S. O. Marx, T. Jayaraman, L. O. Go and A. R. Marks, Rapamycin-FKBP inhibits cell cycle regulators of proliferation in vascular smooth muscle cells, Circ Res, 76, 3, 1995, 412-7; Sehgal S. N., Rapamune (RAPA, rapamycin, sirolimus): mechanism of action immunosuppressive effect results from blockade of signal transduction and inhibition of cell cycle progression. *Clin Biochem*. July 1998; 31(5):335-340; S. N. Sehgal, Sirolimus: its discovery, biological properties, and mechanism of action, Transplant Proc, 35, 3 Suppl, 2003, 7S-14S). To determine if dexamethasone attenuated or augmented the antiproliferative activity of zotarolimus on hCaSMC, the effect of these agents alone and in combination on growth factor induced proliferation was determined. Since re-endothelialization of vascular lesions is considered beneficial, the antiproliferative effects of both agents on hCaEC were assessed alone and in combination. Data were analyzed for interactions (additivity) using an isobologram approach and a combination index analysis as described below.

Proliferation Assay Methods $^3$H Thymidine Uptake Study

Cell proliferation was monitored by following incorporation of $^3$H-thymidine into newly synthesized DNA of cells stimulated by serum and growth factors. Exponentially growing hCaSMCs were seeded into 96-well flat bottom tissue culture plates at 5,000 cells/well (10,000 cells/well for hCaECs). The cells were allowed to attach overnight. The growth medium was removed the following day and cells were washed twice with unsupplemented (basal) medium to remove traces of serum and growth factors. Basal medium (200 µl) was added to each well and the cells incubated in medium lacking growth factors and serum to starve and synchronize them in the $G_0$ state. After starvation (48 hours for hCaSMCs and 39 hours for hCaECs) in medium lacking serum and growth factors, the cells were replenished with 200 µl supplemented medium in the absence or presence of drugs at the desired concentrations. DMSO was maintained at a final concentration of 0.1% in all wells. After a 72-hour incubation period, 25 µl (1 µCi/well) of $^3$H-thymidine (Amersham Biosciences) were added to each well. The cells were incubated at 37° C. for 16-18 hours to allow incorporation of $^3$H-thymidine into newly synthesized DNA and the cells harvested onto 96-well plates containing bonded glass fiber filters using a cell harvester (Harvester 9600, TOMTEC). The filter plates were air dried overnight and MicroScint-20 (25 µl) was added to each filter well and the plates were counted using a TopCount microplate scintillation counter. Controls included medium only, starved cells and cells in complete medium. Drug activity was established by determining the inhibition of $^3$H-thymidine incorporation into newly synthesized DNA relative to cells grown in complete medium.

The data are presented as percent inhibition of $^3$H-thymidine incorporation relative to vehicle treated controls and are given as the mean±SEM of 3-4 experiments. A semi-log plot of the average values of inhibition from each experiment versus drug concentration was generated and the $IC_{50}$ for each experiment was determined by extrapolation of the 50% inhibition level relative to cells incubated in complete medium in the absence of drugs. The final $IC_{50}$s are means of the 3-4 experiments.

In these experiments, the x-axis represents the concentration of the drug being varied. For most of these curves that is zotarolimus alone and in combination with a fixed concentration of dexamethasone. Each graph contains a dexamethasone alone curve and a zotarolimus alone curve. The set of curves in each graph is generated by adding dexamethasone at a fixed concentration (1, 5, 10 or 25 nM) to various concentrations of zotarolimus (0, 0.04, 0.08, 0.8, 4, 8, 40 nM). Each curve represents the dose-response of zotarolimus (whose concentration is given on the x-axis) in the presence of the fixed concentration of dexamethasone given in the legend). Note that in hCaEC higher fixed concentrations of dexamethasone were used (1, 10, 100, 1000 nM).

Two methods were used to analyze the combined effects of zotarolimus and dexamethasone on hCaSMC proliferation. Isobolograms were generated at several effect levels using the method of Tallarida R. J. Tallarida, Drug synergism: its detection and applications, J Pharmacol Exp Ther, 298, 3, 2001, 865-72). The concentration response curves were fit by non-linear regression Prism, GraphPad) to obtain $EC_{50}$ and hill slope values. The concentration eliciting a specific antiproliferative effect was determined using a 4-parameter equation (Equation 1).

$$Y = \text{Bottom} + (\text{Top} - \text{Bottom})/(1 + 10\wedge((\text{Log}EC50 - X) * HillSlope)) \quad [1]$$

$X$ is the logarithm of concentration. $Y$ is the response

Alternatly:

$$Y = \text{Bottom} + \frac{(\text{Top} - \text{Bottom})}{1 + \frac{EC_{50}^{Hillslope}}{[X]^{Hillslope}}}$$

Where X=log concentration of drug yielding Y response and top and bottom values are constrained to 100 and 0, respectively. In addition to isobolograms, the data were analyzed for synergism using the method of Chou and Talalay (T. C. Chou and P. Talalay, *Quantitative analysis of dose-effect relationships: the combined effects of multiple drugs or enzyme inhibitors*, Adv Enzyme Regul, 22, 1984, 27-55) with the following exception. The regression model generated for each curve was used in place of median-effect data (log-logit plot) because the non-linear 4-parameter equation more accurately models the concentration-response curve. The median-effect plot is heavily influenced by values of fractional occupancy below 0.2 and greater than 0.8. The combination indices (CI) for several drug combinations yielding 25%, 50%, 60% and 75% were calculated according to equation 2 (Chou T C, Talalay P. Quantitative analysis of dose-effect relationships: the combined effects of multiple drugs or enzyme inhibitors. *Adv Enzyme Regul.* 1984; 22:27-55), $$(D)_1/(D_x)_1 + (D)_2/(D_x)_2 + (D)_1(D)_2/(D_x)_1(D_x)_2 = CI \quad \text{(equation 2)}$$

where at a specified effect level $(D)_1$ and $(D)_2$ are the concentrations of drug 1 and drug 2 in the combination and $(D_x)_1$ and $(D_x)_2$ are the concentrations of drug I alone and drug 2 alone.

CI values reflect the summation of effects of the combinations assuming each drug was acting in accordance with its own potency. Equation 2 describes predicted effects for the combination of two mutually nonexclusive compounds. If each drug contributes to the combined effect in accordance to its own dose-dependent fractional occupancy, then the CI is equal to 1. Since CI is dependent on the level of effect observed, CI was determined at several effect levels using multiple drug combinations. CI values were plotted as a function of the effect level (or fa) at which they were calculated. CI values, similar to the isobologram analysis are effect level dependent and vary as the level of effect changes therefore it is important to consider effect level in comparing CI values. The accuracy of CI values are, in turn dependent on the accuracy of the concentration values used in their calculation. In this study an accurate method (iterative curve fitting by GraphPad software) was used to calculate drug concentrations from each cumulative dose-response curve at several effect levels. Dose-response curves can be fit to data, which may demonstrate little dose-dependent activity. This is particularly apparent when analyzing dose-response curves generated in the presence of a high concentration of one of the test agents. Errors in determination of drug concentrations from the dose-response curves under these conditions may result in high CI values at low effect levels ($f_a$). Therefore, CI values generated from well defined dose-response curves near or above half-maximal effects (i.e., $f_a$~0.5) are the most accurate predictors of the activity of drug combinations. Under these conditions values of CI below one are considered supra-additive and values significantly over one are considered sub-additive. Values near one are considered additive.

Results and Conclusions

Figure 13:
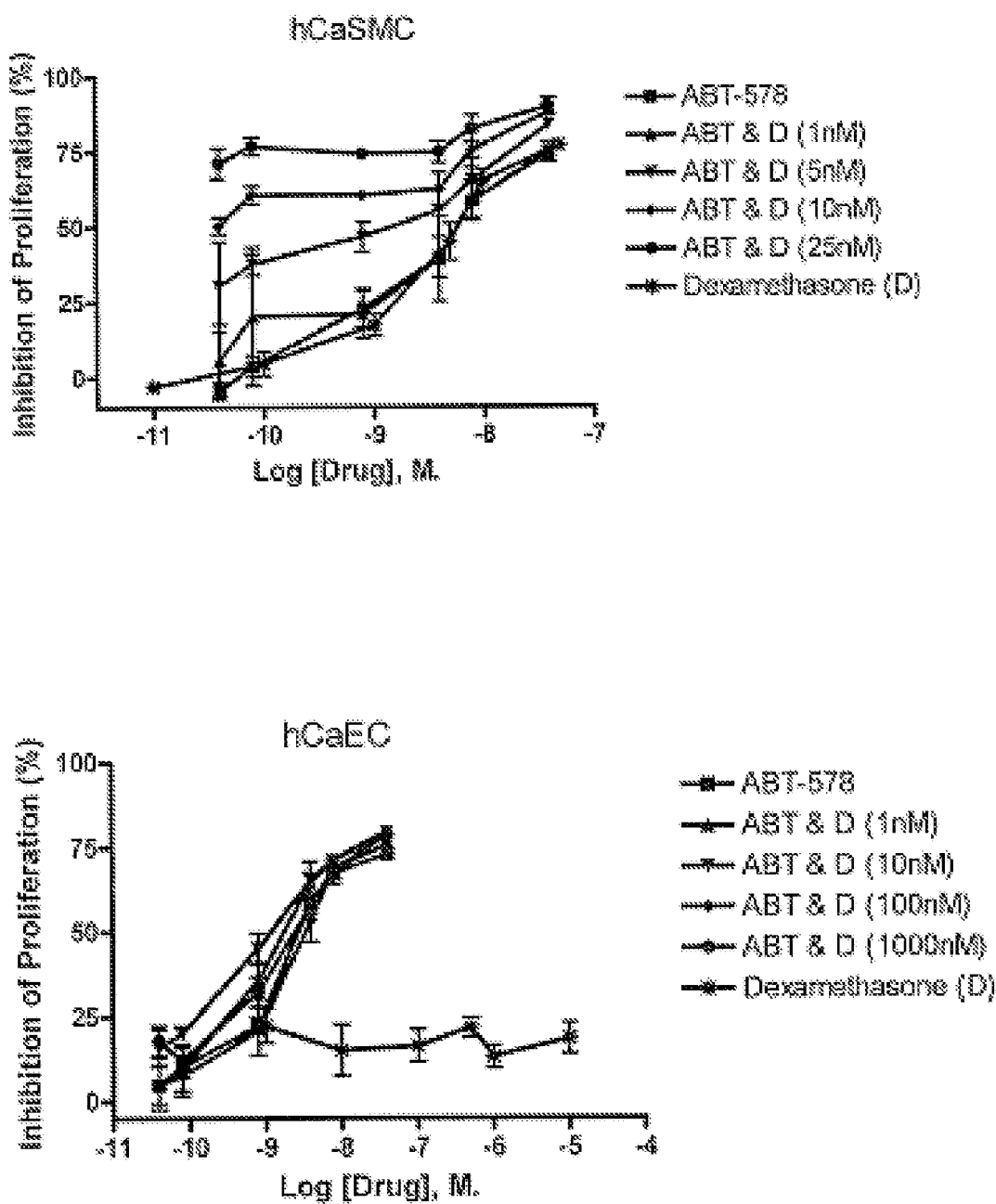
FIG. 13 is a graph of anti-proliferative activity of zotarolimus alone, dexamethasone alone and zotarolimus/dexamethasone combination in human coronary artery smooth muscle cells and endothelial cells.

FIG. 13 shows that dexamethasone does not affect the proliferation of hCaEC but dose-dependently blocks hCaSMC proliferation with an $IC_{50}$ of 9.3 (Table 16). In addition, the data shows that the presence of dexamethasone does not attenuate the antiproliferative activity of zotarolimus, i.e., these drugs in combination are complementary. The data (FIG. 13) also shows that increasing concentrations of both dexamethasone and zotarolimus result in significant inhibition of hCaSMC cell proliferation. Since the combination demonstrates this activity in vitro, these data predict the combinations of zotarolimus and dexamethasone would be beneficial in preventing restenosis.

TABLE 16

Inhibition of Human CaSMC and CaEC Proliferation by Zotarolimus (zotarolimus) and Dexamethasone (DEX) Alone and in Combination.

| Drug | hCaSMC $IC_{50}$ (nM) Mean ± SEM | Drug | hCaEC $IC_{50}$ (nM) Mean ± SEM |
|---|---|---|---|
| Zotarolimus alone | 6.2 ± 1.2 | Zotarolimus alone | 3.2 ± 0.5 |
| Dexamethasone alone | 9.3 ± 0.5 | Dexamethasone alone | >10,000 |
| Zotarolimus + 1 nM DEX | 6.2 ± 1.5 | Zotarolimus + 1 nM DEX | 2.6 ± 0.4 |
| Zotarolimus + 5 nM DEX | 3.8 ± 0.8 | Zotarolimus + 10 nM DEX | 1.7 ± 0.8 |
| Zotarolimus + 10 nM DEX | N.D.* | Zotarolimus + 100 nM DEX | 4.4 ± 0.7 |
| Zotarolimus + 25 nM DEX | N.D.* | Zotarolimus + 1000 nM DEX | 3.3 ± 0.2 |

N.D.* Not detectable: Concentrations of dexamethasone alone at or above 10 nM inhibit proliferation by greater than 50% preventing calculation of zotarolimus $IC_{50}$'s in these experiments.

Figure 14:
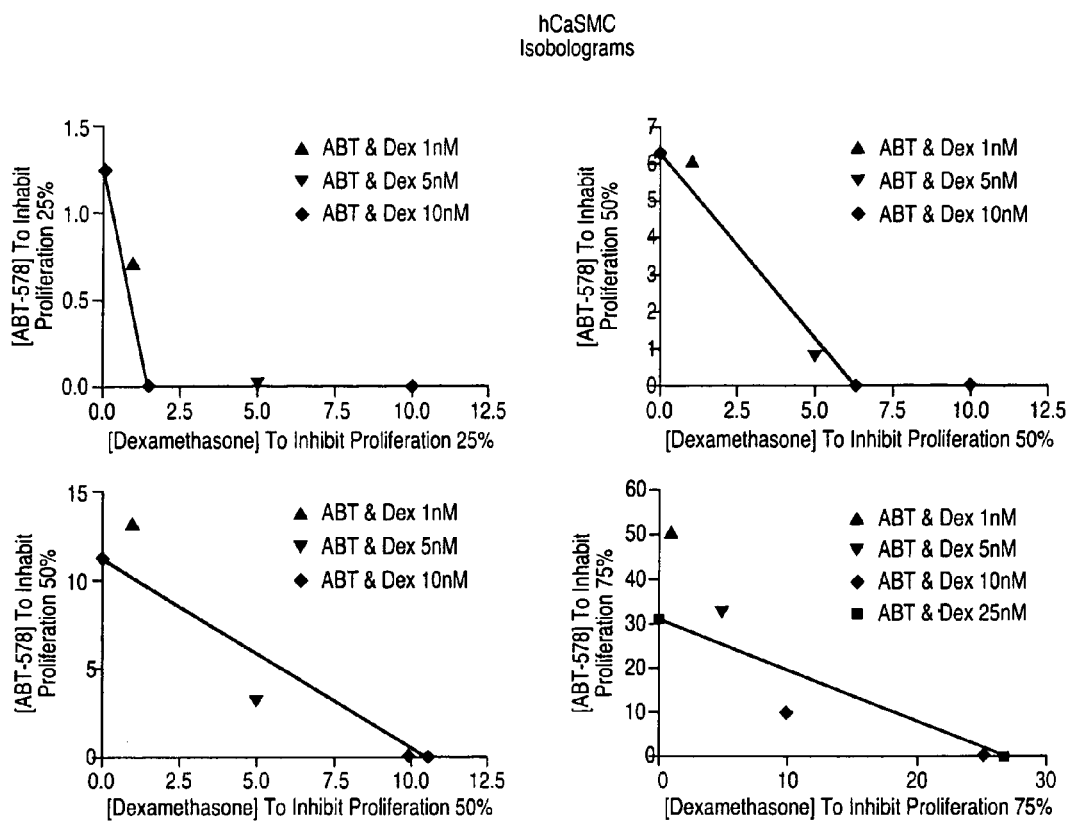
FIG. 14 shows isobolograms of the anti-proliferative activity of a zotarolimus/dexamethasone combination in human coronary artery smooth muscle cells.
Figure 15:
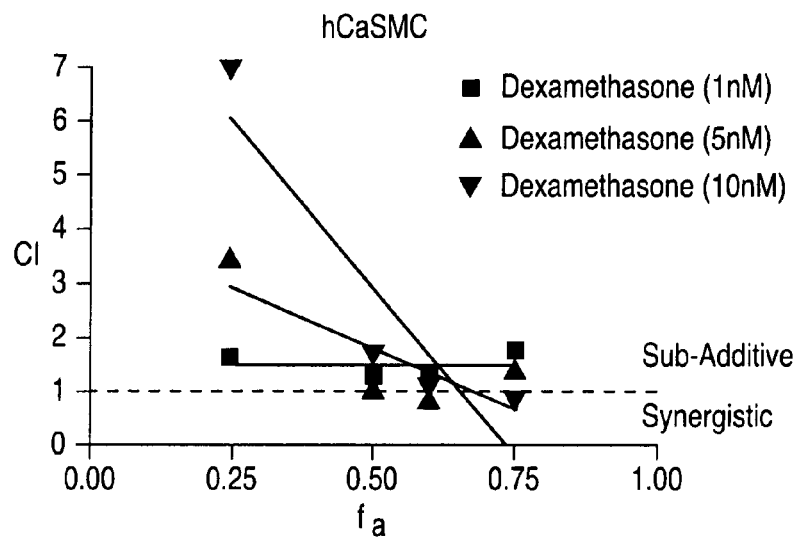
FIG. 15 is a graph of the combination index activity of the anti-proliferative activity of several zotarolimus/dexamethasone combinations in human coronary artery smooth muscle cells.

The higher dexamethasone doses achieved higher levels of proliferation inhibition. The isobologram analysis for hCaSMC is given in FIG. 14 and the combination index (CI) analysis is FIG. 15. In FIG. 14, the concentrations producing the specified level of activity were determined from the dose-response curves generated by non-linear curve fitting of the data means. In FIG. 15, CI levels were determined from the mean data using the method of Chou and Talalay, referenced above. $f_a$ represents the fractional percent inhibition.

The isobologram analysis was performed at various effect levels to determine if the combination of zotarolimus and dexamethasone has additive activity in inhibiting cell proliferation. The combination index analysis shows similar results but all effect levels can be presented in one figure. The isobologram and combination index analyses both show that the combination of zotarolimus and dexamethasone block proliferation and that this effect is similar to that predicted by summing the effects of each single agent since CI values are near one at the half-maximal effect level. No combination analyses were performed on the data from hCaEC since dexamethasone does not demonstrate activity in this cell type.

Dexamethasone blocks hCaSMC proliferation but does not affect hCaEC proliferation. Furthermore, since re-endothelialization of the injured vascular wall is considered beneficial in the prevention of restenosis, these data support the use of dexamethasone as an anti-restenotic agent.

Example 10

Elution Experiments

I. Coating the Stents with Pc-1036 (should Add Pc-2126?John Thinking about)

Prior to any experimentation, coated stents were prepared. These were 3.0 mm×15 mm 316L electropolished stainless steel stents. Each clean stent was spray coated using a filtered 20-mg/mL solution of phosphoryl choline polymer PC-1036 product of Biocompatibles Ltd., Farnham, Surrey, UK) in ethanol. The stents were initially air dried and then cured at 70° C. for 16 hours. They were then sent for gamma irradiation at <25 KGy.

II. Loading the Stent with Drugs of Interest

In these experiments, agents were loaded onto stents and elution profiles were examined. In general, the procedure was as follows. Multiple PC-coated stents were loaded with a drug or drug combination solution. The solutions of the drug(s) were usually in the range of 2-20 mg/mL of zotarolimus (zotarolimus) and 10.0 mg/mL dexamethasone in 100% ethanol, with ~10% PC-1036 added to the solution to enhance film formation. The loading of drug combinations and individual drugs onto the stents was accomplished by spray loading the desired drug(s) onto a stent in a single pass spray system within an isolator unit. All drug-eluting stents were made from Abbott's proprietary TriMaxx construct 15 mm×3.0 mm stents, and all catheters were Medtronic Minneapolis, Minn.) OTW, 15 mm×3.0 mm. The numbers manufactured for each combination provided sufficient numbers for accelerated elution, drug load content, impurity profile, and animal efficacy testing.

The stents were weighed before loading with the drug solution. All stents were spray loaded to their targeted drug contents from solutions containing the appropriate drug(s) and PC1036 in ethanol in a 91:9 ratio. For dexamethasone:zotarolimus combinations, stents were prepared at 10 μg/mm of each drug. 10 ug/mm zotarolimus alone was loaded on single drug stents. Once loaded, all stents were dried in open vials for 30 minutes in an oven set at 40° C. and weighed to determine drug loads. The drug-loaded stents were then overcoated with 5 μg/mm of PC1036 by spraying with a 10 mg/ml polymer solution in ethanol.

After overcoating, the stents were cured in an oven at 70° C. for two hours before weighing to determine overcoat weight. After drug loading, the stents were assembled onto catheters, crimped onto the balloon. The stents were then visually inspected for coating and physical defects. Each stent/catheter was inserted into a packaging hoop and then a Tyvek pouch. The pouch was sealed with a Vertrod Impulse Heat sealer. A stent identification label was placed in the bottom corner on the front side of the pouch, outside of the sealed area containing the product. The product was then placed in white boxes labelled with the product details and shipped for EtO sterilisation. On return from sterilisation, the product was packaged in foil pouches containing sachets of oxygen scavenger and desiccant. The pouches were labelled with the stent identification number and product details. The pouches were sealed whilst flushing with nitrogen.

III. Extracting Drugs from the Stent

For each drug or drug combination tested, three stents were used to evaluate the total amount of drug loaded by the above procedure. The stents were immersed in 6 mL of 50% acetonitrile, 50% buffer solution and sonicated for 20 minutes. The concentration of the each drug in the extraction solution was analyzed by HPLC.

At the end of the elution experiments discussed below, the stents were removed from the elution media and immersed in 6 mL of 50% acetonitrile, 50% buffer solution and sonicated for 20 minutes. The concentration of the each drug in these vials indicated the amount of the drug remaining on the stents at the end of the elution experiments.

IV. Elution Process

For assessment of in vitro drug elution, stents (n=3 for each group) were expanded and then placed in a solution of 10 mM acetate buffer (pH=4.0) with 1% Solutol HS 15 heated to 37° C. in a USP Type II dissolution apparatus. A solubilizing agent was needed because the drugs have very low water solubility. The dissolution medium was buffered to minimize the degradation of "-olimus" drugs that happens at pHs above 6. Buffering at pH 4 solves this problem. Since these drugs have minimum dissociation at these pH ranges, pH has little impact on elution rate.

Samples were pulled from the dissolution bath at selected time intervals using a syringe sampler fitted with only Teflon, stainless steel or glass surfaces. Aliquots were collected after 15 min, 30 min, 1 hr, 2 hr, 4 hr, 6 hr, 8 hr, 12 hr, 18 hr and 24 hr. The samples are assayed for zotarolimus and dexamethasone concentration via HPLC. Data are expressed as drug eluted in micrograms and mean percent eluted.

In the HPLC method, it is necessary to use column switching to minimize the Solutol contamination of the analytical column and to allow rinsing of the guard column or the system becomes coated with the Solutol and the chromatographic retention changes dramatically. The sample was first injected onto a guard column. Once the analyte peak eluted from the guard column and passed onto the analytical column, the guard column was switched out of the analytical path. The guard column was then washed to remove the Solutol prior to the next injection.

V. Elution Results

Figure 16:
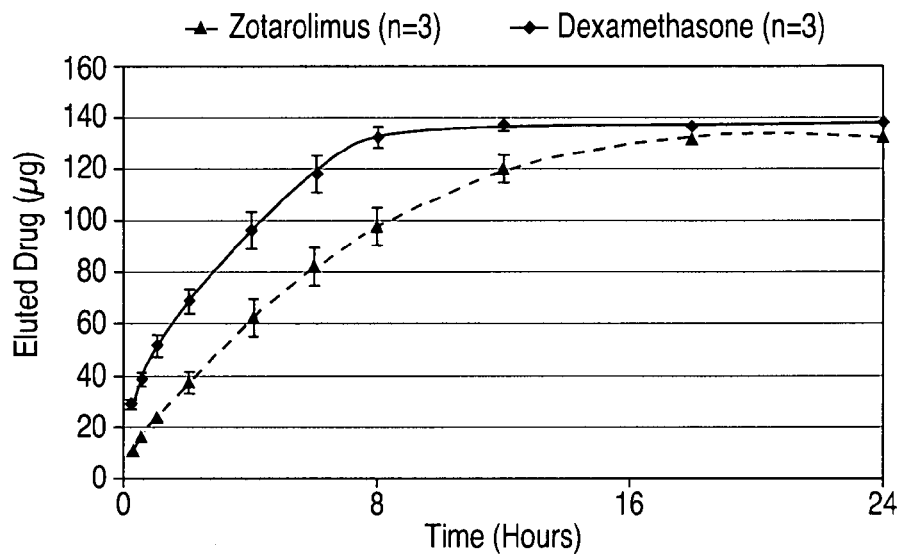
FIGS. 16 and 17 are graphs of accelerated elution rates from stents loaded with zotarolimus or dexamethasone.
Figure 17:
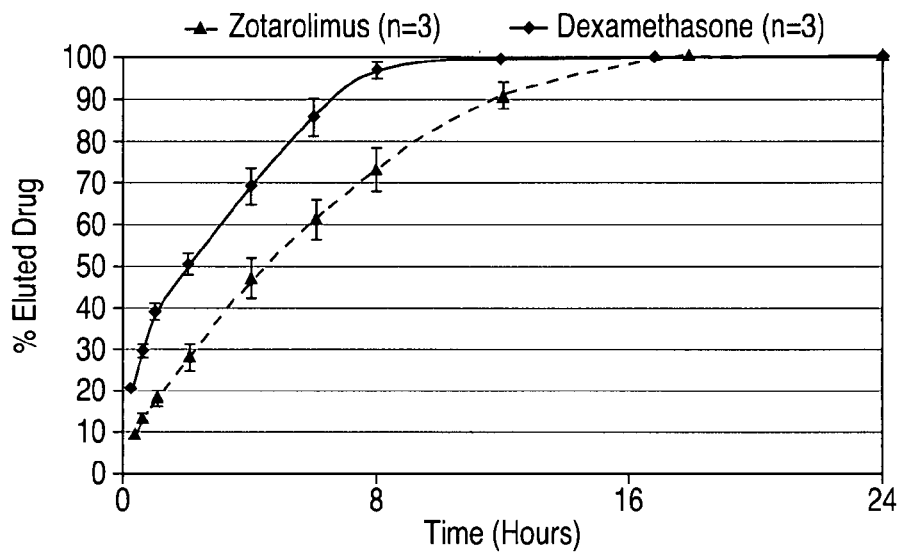
Figure 18:
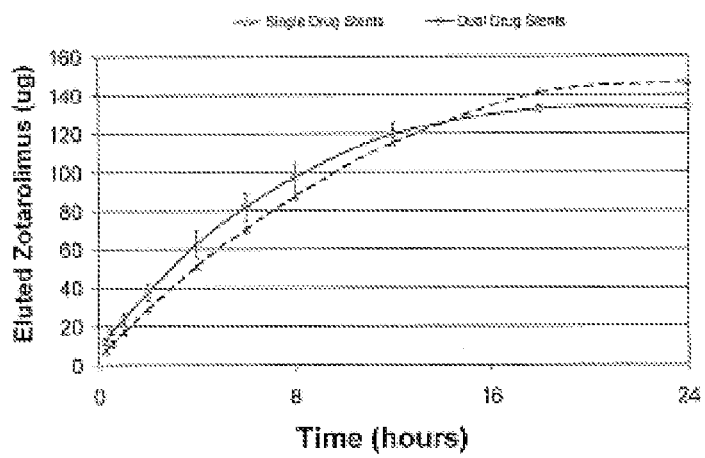
FIG. 18 is a graph showing the elution rates of zotarolimus alone and in the presence of dexamethasone.

FIGS. 16, 17, and 18 illustrate the accelerated elution rate of stents loaded with zotarolimus and Dexamethasone at 10 μg/mm each onto a stent with a 5 μg/mm topcoat of the polymer PC-1036 as detailed above.

In FIG. 16 (eluted drug in micrograms), the 24-hour elution profile shown is for a combination of the anti-inflammatory agent dexamethasone and the anti-proliferative agent is zotarolimus. Elution was carried out as described above. Dexamethasone has a slightly larger burst release at the beginning than zotarolimus but then the two drugs release at about the same rate.

FIG. 17 (% eluted drug) portrays the data in FIG. 15 normalized by the total drug determined on the stent after final stent extract. As can be seen, 100% of both drugs are recovered from the stent coatings. Total drug recovered is in excellent agreement with the drug load predicted by stent weight uptake during the drug loading process. This data along with drug potency and related substances testing on stents from the same batch indicate that the drugs are stable in the polymer coating when manufactured as outlined above. The small error bars (representing the standard deviations) shows that the dual drug elution stents can be manufactured with reproducible elution kinetics.

In FIG. 18, the two curves are the elution profiles (in micrograms release versus time) for zotarolimus, alone and in the presence of dexamethasone, respectively, under the same conditions. As can be seen, the two curves are very similar suggesting that dexamethasone has little effect on the elution profile of zotarolimus.

Example 11

Testing for Neointimal Hyperplasia and Endothelialization after Stent Implantation This test was used to determine the dual drug effect on neointimal hyperplasia and endothelialization. The test exploits the art-accepted porcine coronary overstretch model (Schwartz, R. S., Restenosis and the proportional neointimal response to coronary artery injury: results in a porcine model. *J Am Coll Cardiol*. February 1992; 19(2):267-274) and is usually conducted for approximately 2-8 weeks. Typically, experimental construct includes at least a stent control that resembles the experimental stent in every way except for the change of a single variable, including therapeutic substances or polymer.

In one example, two major coronary arteries may be implanted with one test stent each (Cypher® and Taxus®), and the third major coronary artery is implanted with a control ZoMaxx™ stent in each pig. Additional examples include the implantation of three TriMaxx® control stents, one in each major coronary artery. The responses to these control stents can be compared with those obtained from the ZoMaxx™, Cypher® and Taxus® stents implanted in separate animals.

Stents are implanted using standard techniques. At the conclusion of the study, animals are euthanized, and the hearts are removed, washed and fixed using standard histological preservation techniques (including formalin, formaldehyde, etc.). Stented vessels are excised, then infiltrated and embedded in a suitable medium for sectioning, including methylmethacrylate (MMA), paraffin, or cryomedia. All blocks containing stented vessels are sectioned so that informative sections are obtained; for example, three, in-stent sections and two control sections. Serial thin sections (approximately 5 μm) are usually taken at each level and stained to visualize the cells and tissues (e.g., hematoxylin and eosin (HE) and Masson's Verhoeff Elastin (MVE)). Sections are evaluated and scored using an image analysis system or other art accepted methods of morphological data collection and quantification. The data are scored for neointimal area, neointimal thickness, and percent-area stenosis.

A porcine coronary overstretch model study (Schwartz, R. S., Restenosis and the proportional neointimal response to coronary artery injury: results in a porcine model. *J Am Coll Cardiol*. February 1992; 19(2):267-274) was conducted to examine neointimal formation following stent implantation for 28 days. The study evaluated a number of drug-eluting stents randomized vs. control ZoMaxx™ drug-containing polymer coated stents. In each pig, two major coronary arteries were implanted with one test stent each, and the third major coronary artery was implanted with one ZoMaxx™ stent. The ZoMaxx™ stents including 10 μg/mm zotarolimus as the active pharmaceutical agent. Additionally, three pigs were implanted with three bare metal TriMaxx® stents each (9 total stents) for comparison. For the purposes of this disclosure, five types of stents were compared: 1) ZoMaxx™ stents (3.0×15 mm) containing 10 mcg zotarolimus/mm; 2) commercially available sirolimus-polymer coated Cypher® (3.0×13 mm) stents including 8.5 mcg/mm sirolimus (as defined in Cordis FDA presentation); 3) commercially available paclitaxel-polymer coated Taxus® (3.0×16 mm) stents including 6.8 mcg/mm paclitaxel (calculated); 4) stents coated with a combination of zotarolimus and dexamethasone (3.0×15 mm coated with 10 mcg/mm of each drug); 5) non-drug including TriMaxx® stents (3.0×15 mm).

Stents were implanted with a balloon/artery ratio of 1.30 as determined conventionally by quantitative coronary angiography.

Figure 19:
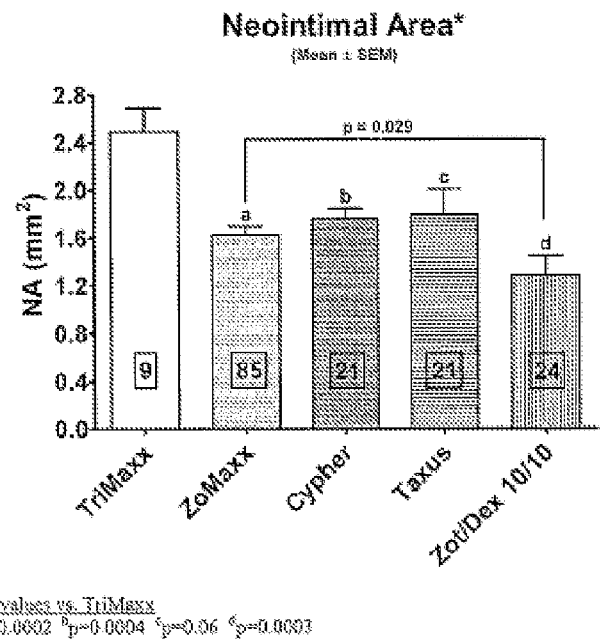
FIG. 19 is a bar graph showing neointimal areas in swine 28 days after implantation of zotarolimus/dexamethasone-eluting stents versus single drug-eluting stents and control stents.
Figure 20:
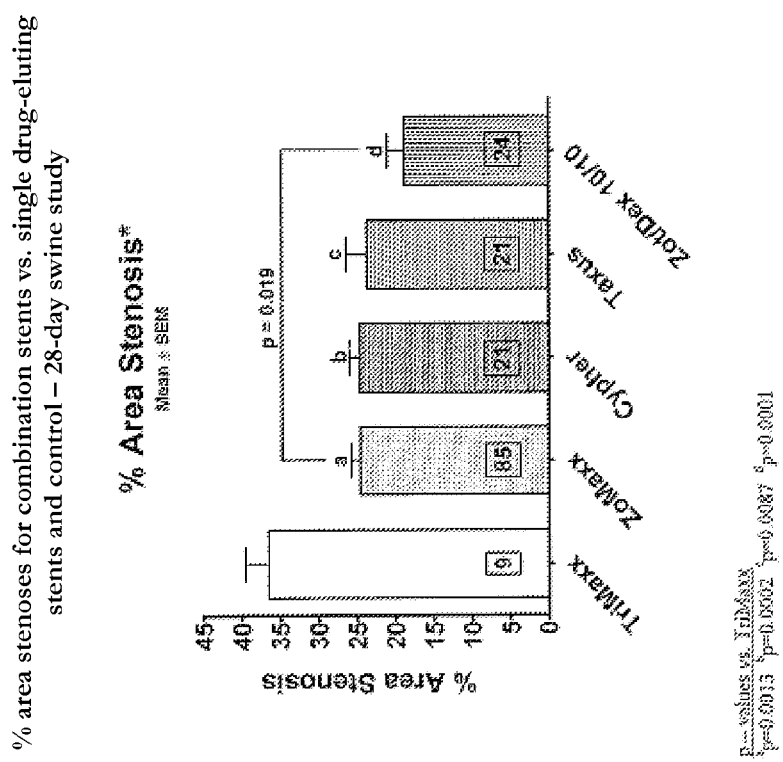
FIG. 20 is a bar graph showing neointimal thicknesses in swine 28 days after implantation of zotarolimus/dexamethasone-eluting stents versus single drug-eluting stents and control stents.
Figure 21:
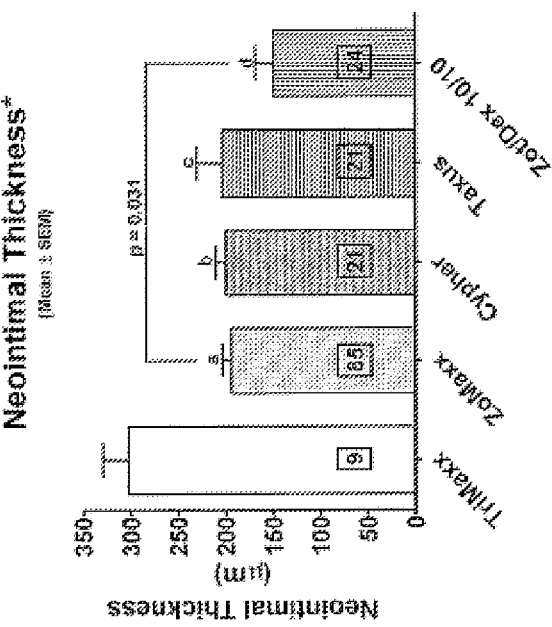
FIG. 21 is a bar graph showing percent area stenosis in swine 28 days after implantation of zotarolimus/dexamethasone-eluting stents versus single drug-eluting stents and control stents.
Figure 22:
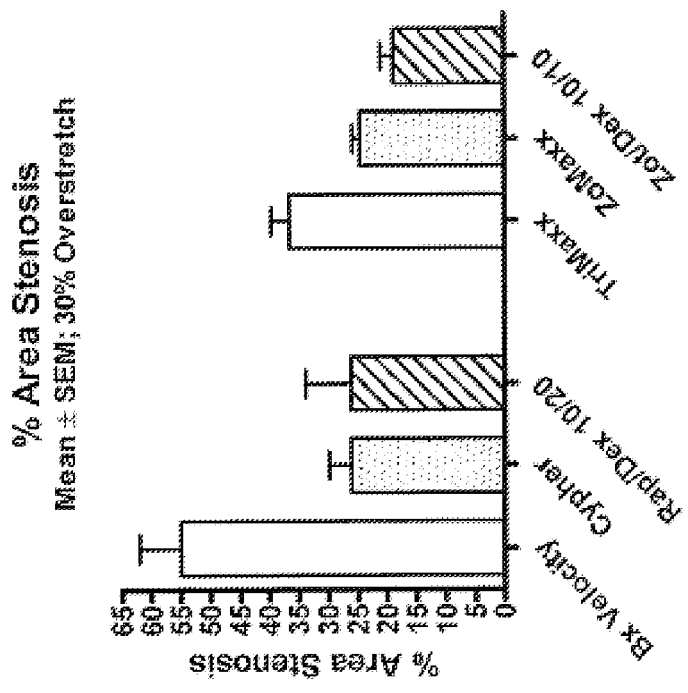
FIG. 22 is a bar graph comparing neointimal area measurements (30% overstretch) from two swine studies after implantation of zotarolimus/dexamethasone-eluting stents versus single drug-eluting stents and control stents.
Figure 23:
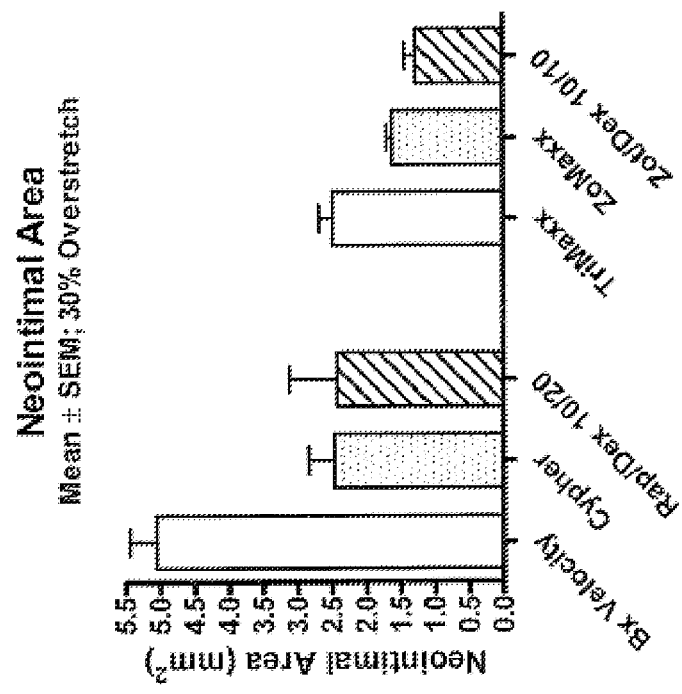
FIG. 23 is a bar graph comparing percent area stenosis (30% overstretch) from two swine studies after implantation of zotarolimus/dexamethasone-eluting stents versus single drug-eluting stents and control stent.
Figure 24:
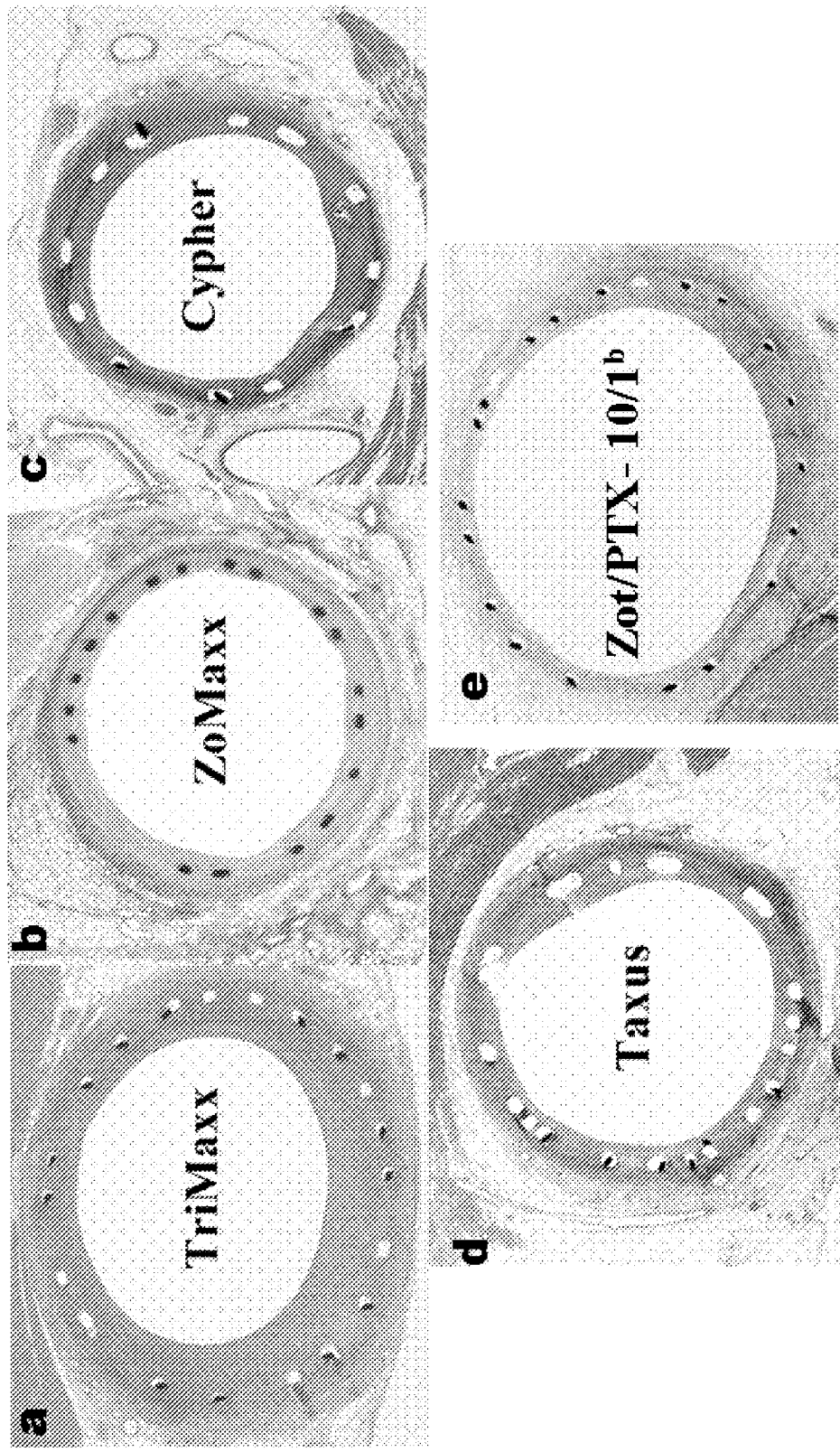
FIG. 24 is a photomicrograph showing the average responses in the two swine studies after implantation of zotarolimus/dexamethasone-eluting stents.

There were no cardiac or stent-related mortalities in the study. After 28 days, animals were euthanized, and the hearts were removed and perfusion fixed at 100 mmHg with lactated Ringer's solution until cleared of blood followed by 10% neutral buffered formalin. Stented vessels were excised then infiltrated and embedded in methylmethacrylate (MMA). All blocks containing stented vessels were sectioned so that three in-stent sections plus two control sections were taken. Two serial thin sections (approximately 5 microns) were taken at each level and stained with Hematoxylin and Eosin (HE) and Masson's Verhoeff Elastin (MVE). Sections were evaluated and scored using the BIOQUANT™ TCW98 image analysis system. Average values for all stents within the five groups for neointimal area, neointimal thickness, and % area stenosis are presented in FIGS. 18-20.

ZoMaxx™, Cypher®, and Taxus® stents had equivalent reductions in formation of neointima, as determined by conventional morphometric measures, compared to TriMaxx® stents. Stents including the zotarolimus/dexamethasone combination also showed a significant reduction in neointimal hyperplasia versus the TriMaxx® stents. In addition, these zotarolimus/dexamethasone combination stents ("Zot/Dex 10/10") also showed a further improvement in reduction in neointima versus ZoMaxx™ zotarolimus-polymer coated, Cypher® sirolimus-polymer coated, and Taxus® paclitaxel-polymer coated stents.

Table 17 summarizes the improvements obtained with ZoMaxx™ polymer-coated and zotarolimus/dexamethasone combination drug stents versus TriMaxx® stents as a control.

TABLE 17

Improvements in morphometric measurements versus TriMaxx non-drug-eluting stent controls.

| Stent | Neointimal Area (mm²) | Neointimal Thickness (μm) | % Area Stenosis | Average |
|---|---|---|---|---|
| ZoMaxx ™ | 34.7% | 36.0% | 32.7% | 34.5% |
| Zot/Dex 10/10 | 48.6% | 50.7% | 48.5% | 49.3% |

Each of the state-of-the-art single drug stents, ZoMaxx™, Cypher®, and Taxus®, showed dramatic reductions in neointimal formation versus the TriMaxx® control stents. For example, the average reduction in neointima for ZoMaxx™ stents was 34.5% versus control. The stents with the 10 mcg/mm zotarolimus/10 mcg/mm dexamethasone combination ("Zot/Dex 10/10") yielded even further reductions in neointimal formation over the already impressive results seen with the best single drug stents available commercially and in clinical trials. The zotarolimus/dexamethasone combination drug-eluting stent gave an average reduction in neointimal formation of 49.3% when compared to TriMaxx® non-drug eluting stents. Compared with ZoMaxx™, Cypher®, and Taxus® drug-eluting stents, the additional dramatic reduction in neointimal hyperplasia was 22.6, 25.4, and 25.2%, respectively (Table 18).

TABLE 18

Improvements in neointimal hyperplasia for 10 mcg/mm zotarolimus/10 mcg/mm dexamethasone combination drug-eluting stents compared with ZoMaxx ™, Cypher ®, and Taxus ® stents.

| Comparator | Neointimal Area | Neointimal Thickness | % Area Stenosis | Average |
|---|---|---|---|---|
| ZoMaxx ™ stent | 21.2% | 23.0% | 23.5% | 22.6% |
| Cypher ® stent | 27.3% | 25.3% | 23.6% | 25.4% |
| Taxus ® stent | 28.5% | 26.5% | 20.7% | 25.2% |

Based on previously published data from literature (Suziki, T, et al., Stent-based delivery of sirolimus reduces neointimal formation in a porcine coronary model. *Circulation*. 2001; 104:1188-1193) and a patent application (Falotico R., U.S. Patent Application 2003/0216699; Table 6.0), one skilled in the art would conclude that combination of 'rolimus drugs and dexamethasone lacked any anti-proliferative benefit over either drug alone. In fact, Table 6.0 explicitly described this effect. In contrast we have unexpectedly demonstrated that our combination zotarolimus/dexamethasone stent is highly efficacious, offering improved reductions in neointimal hyperplasia in the widely utilized porcine coronary overstretch model. In an embodiment, the therapeutic amount of a 'rolimus drug includes zotarolimus or everolimus and is at least 1 μg/mm stent. In another embodiment, the second drug is dexamethasone and the therapeutic amount is at least 0.5 μg/mm stent.

FIGS. 21 through 24 demonstrate the remarkable difference between our results with zotarolimus and dexamethasone and previously published results with sirolimus and dexamethasone. (Suziki, T, et al., Stent-based delivery of sirolimus reduces neointimal formation in a porcine coronary model. *Circulation*. 2001; 104:1188-1193, Falotico R., U.S. Patent Application 2003/0216699; Table 6.0) The previous study showed no benefit between the combination stents and the single drug-eluting stents. Even with the dramatic improvement in the control TriMaxx® stents in comparison to the previously published data of the BX Velocity® stents, in the porcine model with the same overstretch ratio, our zotarolimus/dexamethasone combination product was both substantially better than control and substantially and statistically significantly better than the single drug eluting stent, ZoMaxx™.

Example 12

Clinical Example

The introduction and subsequent widespread use of stents that deliver single anti-proliferative agents has reduced the restenosis rate to less than 10% in the general clinical population. However, a clear rationale exists for the delivery of appropriate drug combinations from stents to treat patients both in the general clinical population and from a variety of cardiovascular disease subsets to reduce restenosis rates and adverse clinical events still further. For example, it is well accepted that the rate of restenosis is significantly increased in stented diabetic patients when compared to those without the disease, and that an inflammatory response to stenting exists in both diabetic and non-diabetic patients (Aggarwal et al., Am. J. Cardiol. 92: 924-929, 2003). In addition, inflammation is a hallmark in patients with acute coronary syndrome (ACS), a term which defines a range of acute myocardial ischemic conditions, including unstable angina, non-ST segment elevation myocardial infarction, as well as infarction associated with persistent ST-segment elevation. These patients are often prime candidates for stent deployment, and relative to the general patient population undergoing percutaneous intervention PCI), have significantly higher rates of recurrent ischemia, reinfarction and subsequent need for repeat PCI procedures. Finally, obesity is often associated with a pro-inflammatory state and endothelial dysfunction. Both conditions are known to be independent predictors of early restenosis after coronary stent placement. In fact, a case has been made for an association between obesity, interleukin-6 (IL-6) production by adipocytes and coronary artery disease, suggesting a link between elevations of this inflammatory cytokine and the development of CAD in this sub-set of patients (Yudkin et al., Atherosclerosis 148: 209-214, 2000).

Diabetic patients are known to exhibit higher levels of the inflammatory marker, c-reactive protein (CRP) than non-diabetic patients (Aggarwal et al., Dandona and Aljada, Am. J. Cardiol. 90 (suppl): 27G-33 G, 2002). This protein has been clearly identified as a key inflammatory mediator in patients with coronary artery disease, and is a predictor of adverse events in patients with severe unstable angina (Biondi-Zoccai et al, J. Am. Coll. Cardiol. 41: 1071-1077, 2003). CRP is known to stimulate the production of monocyte chemoattractant protein (MCP-1) by human endothelial cells. The release of this mediator is accompanied by the influx of monocytes, resulting in a marked inflammatory state as these cells are activated and move into the sub-endothelial space, where they form foam cells containing oxidized low-density lipoprotein (LDL). Plasma IL-6 and tumor necrosis factor-alpha (TNF-α) are inflammatory cytokines that are also elevated in the obese patient, and in type 2 diabetics. In fact, elevation of high-sensitivity CRP, IL-6 or serum vascular cell adhesion molecule-1 (VCAM-1) have been associated with increased mortality in patients with coronary artery diseases Roffi and Topol, Eur. Heart J. 25: 190-198, 2004). Since it has been shown that neointimal formation, a hallmark of the restenotic process, is accentuated by inflammation, the use of stents which deliver anti-inflammatory agents to the local vessel environment would be expected to have clear utility in diabetic patients.

Disruption of an atheromatous plaque is central to the initiation of an acute coronary syndrome (Grech and Ramsdale, Br. Med. J., 326: 1259-1260, 2003). Plaque rupture may be induced by increased concentrations of matrix metalloproteinases secreted by foam cells, leading to plaque instability and ultimate rupture of the thin fibrous cap which overlies the developing lesion. In addition, tissue factor, which is expressed on the surface of foam cells, activates coagulation factor VII, which leads to the formation of thrombin. Generation of this protein leads to platelet activation and aggregation, as well as the conversion of fibrinogen to fibrin, and the clear formation of thrombus. Initial concern regarding the deployment of stents in this setting appears unfounded, since improvements in stent deployment and technique have shown that stented patients have less recurrent ischemia, reinfarction and need for repeat angioplasty (Grech and Ramsdale, 2003). The close relationship between inflammation and the development of coronary artery lesions make the delivery of anti-inflammatory and anti-proliferative agents an attractive approach to treating such patients.

Data has been published which clearly describe the utility of anti-inflammatory drugs in patients with coronary disease. In the IMPRESS study, event free survival was significantly enhanced in patients who received long-term oral therapy with the anti-inflammatory drug prednisone (Versaci et al., J. Am. Coll. Cardiol. 40: 1935-1942, 2002). Furthermore, patients implanted with stents which elute the anti-inflammatory agent dexamethasone (Patti et al., Am. J. Cardiol. 95: 502-505, 2005) displayed significant reductions in CRP levels within 48 hours of implantation. This effect was especially noted in patients with CRP values $\geqq 3$ mg/dT, and persisted for prolonged periods.

Dexamethasone-eluting stents have also shown clear benefit in patients with unstable versus stable angina, as reported in the STRIDE trial (Liu et al., 4: 265, 2002). Our findings which illustrate the anti-proliferative effect of dexamethasone on vascular smooth muscle cells, coupled with the well-known anti-inflammatory effect of this drug suggest that a stent which contains both the potent antiproliferative zotarolimus, and dexamethasone, will have utility in further reducing the rate of restenosis, as suggested by the results of the swine studies reported here.

The stents described herein will be deployed in patients who are diagnosed with ischemic heart disease due to stenotic lesions in coronary arteries and in subsets of the clinical population at higher risk for recurrent coronary disease and other adverse clinical events. Other targets for intervention include peripheral vascular diseases including stenosis in the superficial femoral arteries, renal arteries, iliacs, and vessels below the knee. Target vessels for interventional procedures will be reached using percutaneous vascular access via either the femoral or radial artery, and a guiding catheter will be inserted into the vessel. The target lesion will then be crossed with a guidewire, and the balloon catheter will be inserted either over the wire or using a rapid exchange system. The physician will determine the appropriate size of the stent to be implanted by online quantitative coronary angiography (QCA) or by visual estimate. The stent will be deployed using appropriate pressure as indicated by the compliance of the stent, and a post-procedure angiogram can then be obtained. When the procedure is completed, the patient will be regularly monitored for angina status and for the existence of any adverse events. The need for repeat procedures will also be assessed.

In embodiments, antiproliferative activity of the first drug reduces formation of neointima by at least 25% versus a non-drug eluting stent in a porcine coronary injury model with 30% overstretch. In other embodiments, the antiproliferative effect of the first drug complements the antiproliferative effect of the second drug and reduces formation of neointima by at least 30% versus non-drug eluting stents in a porcine injury model with 30% overstretch.

In embodiments of the system, the drugs have a combination index less than or equal to 10. In other embodiments, the system further includes a ratio of the therapeutic amount of the first drug to the therapeutic amount of the second drug of 1:10 to 10:1 ratio. In still yet other embodiments, the pharmaceutical composition for reducing neointimal hyperplasia is administered locally, and includes zotarolimus or everolimus and dexamethasone, wherein the zotarolimus or everolimus and the dexamethasone are in a ratio of between about 10:1 to about 1:10. Still yet in other embodiments, the pharmaceutical composition for reducing neointimal hyperplasia is administered locally, and includes at least one olimus drug and at least one glucocorticosteriod, and wherein the olimus drug(s) and the glucocorticosteriod(s) are in a ratio of between about 10:1 to about 1:10. Furthermore, endothelialization is accelerated relative to a single drug eluting stent.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

REFERENCES

Aggarwal, A., D. J. Schneider, B. E. Sobel, and H. L. Dauerman. 2003. Comparison of inflammatory markers in patients with diabetes mellitus versus those without before and after coronary arterial stenting. *Am J Cardiol.* 92:924-9.

Baker, H., A. Sidorowicz, S. N. Sehgal, and C. Vezina. 1978. Rapamycin (AY-22,989), a new antifungal antibiotic. III. In vitro and in vivo evaluation. *J Antibiot (Tokyo).* 31:539-45.

Bierer, B. E., S. L. Schreiber, and S. J. Burakoff. 1991. The effect of the immunosuppressant FK-506 on alternate pathways of T cell activation. *Eur J Immunol.* 21:439-45.

Biondi-Zoccai, G. G., A. Abbate, G. Liuzzo, and L. M. Biasucci. 2003. Atherothrombosis, inflammation, and diabetes. *J Am Coll Cardiol.* 41:1071-7.

Brown, E. J., M. W. Albers, T. B. Shin, K. Ichikawa, C. T. Keith, W. S. Lane, and S. L. Schreiber. 1994. A mammalian protein targeted by G1-arresting rapamycin-receptor complex. *Nature.* 369:756-8.

Bunchman, T. E., and C. A. Brookshire. 1991. Smooth muscle cell proliferation by conditioned media from cyclosporine-treated endothelial cells: a role of endothelin. *Transplant Proc.* 23:967-8.

Caufield. U.S. Pat. No. 5,023,262. 1991. Hydrogenated Rapamycin Derivatives.

Caufield. WO 92/05179. 1992. Carboxylic Acid Esters of Rapamycin.

Chou, T. C., and P. Talalay. 1984. Quantitative analysis of dose-effect relationships: the combined effects of multiple drugs or enzyme inhibitors. *Adv Enzyme Regul.* 22:27-55.

Dandona, P., and A. Aljada. 2002. A rational approach to pathogenesis and treatment of type 2 diabetes mellitus, insulin resistance, inflammation, and atherosclerosis. *Am J Cardiol.* 90:27 G-33G.

Dumont, F. J., M. R. Melino, M. J. Staruch, S. L. Koprak, P. A. Fischer, and N. H. Sigal. 1990. The immunosuppressive macrolides FK-506 and rapamycin act as reciprocal antagonists in murine T cells. *J. Immunol.* 144:1418-24.

Eng. U.S. Pat. No. 4,401,653. 1983. Combination of Rapamycin and Picibanil for the Treatment of Tumors.

Failli. EPO 467606. 1992a. Rapamycin Derivatives.

Failli. U.S. Pat. No. 5,120,842. 1992b. Silyl Ethers of Rapamycin.

Failli. U.S. Pat. No. 5,177,203. 1993. Rapamycin 42-Sulfonates and 42-(N-Carboalkoxy) Sulfamates Useful as Immunosuppressie Agents.

Falotico, R. Publication No. US 2003/0216699. 2003. Coated medical devices for the prevention and treatment of vascular disease.

Fretz, H., M. Albers, A. Gala, R. Standaert, W. Lane, S. Burakoff, B. Bierer, and S. Schreiber. 1991. Rapamycin and FK506 binding proteins (immunophilins). *J. Am. Chem. Soc.* 113:1409-1411.

Grech, E. D., and D. R. Ramsdale. 2003. Acute coronary syndrome: unstable angina and non-ST segment elevation myocardial infarction. *Bmj.* 326:1259-61.

Harding, M. W., A. Galat, D. E. Uehling, and S. L. Schreiber. 1989. A receptor for the immunosuppressant FK506 is a cis-trans peptidyl-prolyl isomerase. *Nature.* 341:758-60.

Hayward, C., D. Yohannes, and S. Danishefsky. 1993. Total synthesis of rapamycin via a novel titanium-mediated aldol macrocyclization reaction. *J. Am. Chem. Soc.* 115:9345-9346.

Higuchi, T., and V. Stella. 1987. Pro-drugs as Novel Delivery systems.

Igaki, K. U.S. Pat. No. 6,413,272. 2002. Stent for vessel.

Ji, Q., M. Reimer, and T. El-Shourbagy. 2004. 96-Well liquid-liquid extraction liquid chromatography-tandem mass spectrometry method for the quantitative determination of ABT-578 in human blood samples. *Journal of Chromatography B.* 805:67-75.

Kao. U.S. Pat. No. 5,120,725. 1992a. Bicyclic Rapamycins.

Kao. U.S. Pat. No. 5,120,727. 1992b. Rapamycin Dimers.

Kino, T., N. Inamura, F. Sakai, K. Nakahara, T. Goto, M. Okuhara, M. Kohsaka, H. Aoki, and T. Ochiai. 1987. Effect of FK-506 on human mixed lymphocyte reaction in vitro. *Transplant Proc.* 19:36-9.

Lafont, A., and P. Libby. 1998. The smooth muscle cell: sinner or saint in restenosis and the acute coronary syndromes? *J Am Coll Cardiol.* 32:283-5.

Luly. 1995. Macrocyclic Immunomodulators.

Martel, R. R., J. Klicius, and S. Galet. 1977. Inhibition of the immune response by rapamycin, a new antifungal antibiotic. *Can J Physiol Pharmacol.* 55:48-51.

Marx, S. O., T. Jayaraman, L. O. Go, and A. R. Marks. 1995. Rapamycin-FKBP inhibits cell cycle regulators of proliferation in vascular smooth muscle cells. *Circ Res.* 76:412-7.

Miller, M. L., and I. Ojima. 2001. Chemistry and chemical biology of taxane anticancer agents. *Chem. Rec.* 1:195-211.

Morris, R. 1992. Rapamycins: antifungal, antitumor, antiproliferative, and immunosuppressive macrolides. *Transplant. Rev.* 6:39-87.

Morris, R., and B. Meiser. 1989. Identification of a new pharmacologic action for an old compound. *Med. Sci. Res.* 17:609.

Nicolaou, K., T. Chakraborty, A. Piscopio, N. Minowa, and P. Bertinato. 1993. Total synthesis of rapamycin. *J. Am. Chem. Soc.* 115:4419-4420.

Okuhara, M., T. Hirokazu, G. Toshio, K. Tohru, and H. Hiroshi. EP Patent No. 0184162. 1986. Tricyclo compounds, a process for their production and a pharmaceutical composition containing the same.

Or, Y., J. Luly, and R. Wagner. U.S. Pat. No. 5,527,907. 1996. Macrolide immunomodulators.

Paiva, N. L., A. L. Demain, and M. F. Roberts. 1991. Incorporation of acetate, propionate, and methionine into rapamycin by *Streptomyces hygroscopicus*. *J Nat Prod.* 54:167-77.

Prescott, D. M. e. 1976 In Methods in cell biology. Vol. XIV. Academic Press., San Diego [etc.]. 33 et seq.

Rakhit. U.S. Pat. No. 4,316,885. 1982. Acyl Derivatives of Rapamycin.

Roche, E. 1987. Bioreversible Carriers in Drug Design. American Pharmaceutical Association and Pergamon Press.

Roffi, M., and E. J. Topol. 2004. Percutaneous coronary intervention in diabetic patients with non-ST-segment elevation acute coronary syndromes. *Eur Heart J.* 25:190-8.

Romo, D., S. Meyer, D. Johnson, and S. Schrieber. 1993. Total synthesis of (−)-rapamycin using an Evans-Tishchenko fragment coupling. *J. Am. Chem. Soc.* 115:7906-7907.

Sabatini, D. M., H. Erdjument-Bromage, M. Lui, P. Tempst, and S. H. Snyder. 1994. RAFT1: a mammalian protein that binds to FKBP12 in a rapamycin-dependent fashion and is homologous to yeast TORs. *Cell.* 78:35-43.

Schiff, P. B., and S. B. Horwitz. 1980. Taxol stabilizes microtubules in mouse fibroblast cells. *Proc Natl Acad Sci USA.* 77:1561-5.

Schwartz, R. 1992. Restenosis and the proportional neointimal response to coronary artery injury: results in a porcine model. *J Am Coll Cardiol.* 19:267-274.

Sehgal, S. N. U.S. Pat. No. 3,929,992. 1975. Rapamycin and Process of Preparation.

Sehgal, S. N. U.S. Pat. No. 3,993,749. 1976. Rapamycin and Process of Preparation.

Sehgal, S. N. 1998. Rapamune (RAPA, rapamycin, sirolimus): mechanism of action immunosuppressive effect results from blockade of signal transduction and inhibition of cell cycle progression. *Clin Biochem.* 31:335-40.

Sehgal, S. N. 2003. Sirolimus: its discovery, biological properties, and mechanism of action. *Transplant Proc.* 35:7 S-14S.

Sehgal, S. N., H. Baker, C. P. Eng, K. Singh, and C. Vezina. 1983. Demethoxyrapamycin (AY-24,668), a new antifungal antibiotic. *J Antibiot (Tokyo).* 36:351-4.

Sehgal, S. N., H. Baker, and C. Vezina. 1975. Rapamycin (AY-22,989), a new antifungal antibiotic. II. Fermentation, isolation and characterization. *J Antibiot (Tokyo).* 28:727-32.

Shichiri, M., Y. Hirata, T. Nakajima, K. Ando, T. Imai, M. Yanagisawa, T. Masaki, and F. Marumo. 1991. Endothelin-1 is an autocrine/paracrine growth factor for human cancer cell lines. *J Clin Invest.* 87:1867-71.

Siekierka, J. J., S. H. Hung, M. Poe, C. S. Lin, and N. H. Sigal. 1989. A cytosolic binding protein for the immunosuppressant FK506 has peptidyl-prolyl isomerase activity but is distinct from cyclophilin. *Nature.* 341:755-7.

Stack, R., H. Clark, W. Wlaker, and J. McElhaney. U.S. Pat. No. 5,527,337. 1996. Bioabsorbable stent and method of making the same.

Stella. U.S. Pat. No. 4,650,803. 1987. Prodrugs of Rapamycin.

Surendra. U.S. Pat. No. 4,885,171. 1989. Use of Rapamycin in Treatment of Certain Tumors.

Suzuki, T., G. Kopia, S. Hayashi, L. R. Bailey, G. Llanos, R. Wilensky, B. D. Klugherz, G. Papandreou, P. Narayan, M. B. Leon, A. C. Yeung, F. Tio, P. S. Tsao, R. Falotico, and A. J. Carter. 2001. Stent-based delivery of sirolimus reduces neointimal formation in a porcine coronary model. *Circulation.* 104:1188-93.

Tallarida, R. J., F. Porreca, and A. Cowan. 1989. Statistical analysis of drug-drug and site-site interactions with isobolograms. *Life Sci.* 45:947-61.

Vezina, C., A. Kudelski, and S. N. Sehgal. 1975. Rapamycin (AY-22,989), a new antifungal antibiotic. I. Taxonomy of the producing streptomycete and isolation of the active principle. *J Antibiot (Tokyo).* 28:721-6.

Yamagishi, S., C. C. Hsu, K. Kobayashi, and H. Yamamoto. 1993. Endothelin 1 mediates endothelial cell-dependent proliferation of vascular pericytes. *Biochem Biophys Res Commun.* 191:840-6.

Yudkin, J. S., M. Jumari, S. E. Humphries, and V. Mohamed-Ali. 2000. Inflammation, obesity, stress and coronary heart disease: is interleukin-6 the link? *Atherosclerosis.* 148: 209-14.

What is claimed is:

1. An implantable medical device for providing controlled release delivery of drugs comprising:
    a composition including a therapeutic amount of a first drug and a therapeutic amount of a second drug for treatment or inhibition of neointimal hyperplasia in a blood vessel lumen;
    wherein said first drug is zotarolimus or a salt thereof;
    wherein said second drug is dexamethasone or a salt thereof;
    wherein said therapeutic amount of said second drug improves the effect of said therapeutic amount of said first drug with respect to one effect selected from the group consisting of neointimal area, neointimal thickness, percentage area stenosis, inflammation score, and a combination thereof; and
    wherein the implantable medical device is a stent or an angioplasty balloon.

2. The implantable medical device according to claim 1, wherein said stent further comprises a coating on at least a portion of the surface of said stent.

3. The implantable medical device according to claim 2, wherein said composition is included in the coating.

4. The implantable medical device according to claim 3, wherein said coating comprises a polymer.

5. The implantable medical device according to claim 4, wherein said polymer comprises a phosphorylcholine polymer.

6. The implantable medical device according to claim 4, wherein said polymer is selected from the group consisting of fluoropolymers, poly(acrylates), silicones, resins, nylons, and poly(amides).

7. The implantable medical device according to claim 3, wherein said therapeutic amount of said first drug is at least 1 μg/mm of stent length on a 3.0×15.0 stent.

8. The implantable medical device according to claim 1, wherein said therapeutic amount of said second drug is at least 0.5 μg/mm of stent length on a 3.0×15.0 stent.

9. The implantable medical device according to claim 1, further comprising a third therapeutic drug.

10. The implantable medical device according to claim 9, wherein said third therapeutic drug is selected from the group consisting of anti-proliferative agents, anti-platelet agents, anti-inflammatory agents, anti-lipidemic agents, anti-thrombotic agents, thrombolytic agents, their salts and prodrugs, and combinations thereof.

11. The implantable medical device according to claim 9, wherein said third therapeutic drug is a glucocorticosteroid selected from the group consisting of methylprednisolone, prednisolone, prednisone, triamcinolone, dexamethasone, mometasone, beclomethasone, ciclesonide, bedesonide, triamcinolone, clobetasol, flunisolide, loteprednol, budesonide, fluticasone, their salts and prodrugs, and combinations thereof.

12. The implantable medical device according to claim 9, wherein said third therapeutic drug is a steroid hormone selected from the group consisting of estradiol, its salts and prodrugs, and combinations thereof.

13. The implantable medical device according to claim 9, wherein said third therapeutic drug comprises an agent selected from the group consisting of adalimumab, anti-Monocyte Chemoattractant Protein—(MCP-1) antibodies, C-C chemokine receptor type 2 (CCR2) receptor antagonists, anti-Granulocyte-macrophage colony-stimulating factor (GM-CSF) antibodies, anti-Tumor Necrosis Factor (TNF) antibodies, anti-Interleukin 1 (IL-1) antibodies, anti-Interleukin 2 (IL-2) antibodies, anti-Interleukin 3 (IL-3) antibodies, anti-Interleukin 4 (IL-4) antibodies, anti-Interleukin 8 (IL-8) antibodies, anti-Interleukin 15 (IL-15) antibodies, anti-Interleukin 18 (IL-18) antibodies, their salts and prodrugs, and combinations thereof.

14. The implantable medical device according to claim 9, wherein said third therapeutic drug comprises an anti-proliferative agent selected from the group consisting of alkylating agents, tauromustine, bofumustime, fotemustine, cyclophosphamide, chlorambucil, busulfan, carmustine, lomustine, methotrexate, fluorouracil, 5-bromodeoxyuridine, 6-azacytidine, cytarabine, mercaptopurine, pentostatin, vinca alkaloids vinblastine, vincristine, paclitaxel, nocodazole, indirubin, anthracycline, daunorubicin, daunomycin, plicamycin, antibiotics, doxorubicin, bleomycin, mitomycin, cisplatin, procarbazine, etoposide, teniposide, their salts and prodrugs, and combinations thereof.

15. The implantable medical device according to claim 9, wherein said third therapeutic drug comprises an anti-platelet agent selected from the group consisting of glycoprotein IIB/IIA inhibitors, abciximab, eptifibatide, tirofiban, adenosine reuptake inhibitors, dipyridamole, Adenosine diphosphate (ADP) receptor inhibitors, clopidogrel, ticlopidine, cyclooxygenase inhibitors, acetylsalicylic acid, phosphodiesterase inhibitors, cilostazol, their salts and prodrugs, and combinations thereof.

16. The implantable medical device according to claim 9, wherein said third therapeutic drug comprises an anti-inflammatory agent selected from the group consisting of steroids, dexamethasone, hydrocortisone, fluticasone, clobetasol, mometasone, estradiol, non-steroidal anti-inflammatory agents, acetaminophen, ibuprofen, naproxen, sulindac, piroxicam, mefanamic acid, anti-IL-1 antibodies, anti-IL-2 antibodies, anti-IL-8 antibodies, anti-IL-15 antibodies, anti-IL-18 antibodies, anti-TNF antibodies, their salts and prodrugs, and combinations thereof.

17. The implantable medical device according to claim 8, wherein said third therapeutic drug comprises an anti-thrombotic agent selected from the group consisting of heparins, heparin sulfate, unfractionated heparins, clivarin, dalteparin, enoxaparin, nadroparin, tinzaparin, direct thrombin inhibitors, argatroban, hirudin, hirulog, hirugen, their salts and prodrugs, and combinations thereof.

18. The implantable medical device according to claim 8, wherein said third therapeutic drug comprises an anti-lipidemic agent selected from the group consisting of Hydroxy-Methyl-Glutaryl-Coenzyme A (HMG CoA) reductase inhibitors, mevastatin, lovastatin, simvastatin, pravastatin, fluvastatin, fibric acid derivatives, fenofibrate, clofibrate, gemfibrozil, lipid-lowering agents, nicotinic acid, probucol, their salts and prodrugs, and combinations thereof.

19. The implantable medical device according to claim 9, wherein said third therapeutic drug comprises thrombolytic agents selected from the group consisting of streptokinase, urokinase, pro-urokinase, tissue plasminogen activators, alteplase, reteplase, tenectaplase, their salts and prodrugs, and combinations thereof.

20. The implantable medical device according to claim 1, wherein said therapeutic amount of said second drug is at least 1 μg/mm of stent length on a 3.0×15.0 stent.

21. The implantable medical device according to claim 1, wherein said first drug reduces formation of neointima by at least 25% versus a non-drug eluting stent in a porcine coronary injury model with 30% overstretch.

22. The implantable medical device according to claim 1, further comprising a ratio of said therapeutic amount of said first drug to said therapeutic amount of said second drug of 1:10 to 10:1.

23. The implantable medical device according to claim 22, wherein said ratio of said therapeutic amount of said first drug to said therapeutic amount of said second drug is about 1:1.

\* \* \* \* \*